(12) United States Patent
Rigatti et al.

(10) Patent No.: US 8,753,816 B2
(45) Date of Patent: Jun. 17, 2014

(54) SEQUENCING METHODS

(75) Inventors: Roberto Rigatti, Essex (GB); Jonathan Mark Boutell, Essex (GB); Jason Richard Betley, Essex (GB); Niall Anthony Gormley, Essex (GB); Mostafa Ronaghi, San Diego, CA (US); Dirk Evers, Essex (GB)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 13/881,320

(22) PCT Filed: Oct. 26, 2011

(86) PCT No.: PCT/EP2011/068790
§ 371 (c)(1),
(2), (4) Date: Apr. 24, 2013

(87) PCT Pub. No.: WO2012/055929
PCT Pub. Date: May 3, 2012

(65) Prior Publication Data
US 2013/0281306 A1    Oct. 24, 2013

Related U.S. Application Data

(60) Provisional application No. 61/406,928, filed on Oct. 26, 2010.

(51) Int. Cl.
*C12Q 1/68*   (2006.01)
*C12P 19/34*  (2006.01)

(52) U.S. Cl.
USPC ............................................ 435/6.1; 435/91.2

(58) Field of Classification Search
USPC .................................................. 435/6.1, 91.2
See application file for complete search history.

(56) References Cited

U.S. PATENT DOCUMENTS

| | | | |
|---|---|---|---|
| 5,635,400 A | 6/1997 | Brenner | |
| 2005/0186576 A1 | 8/2005 | Chan et al. | |
| 2006/0183145 A1 | 8/2006 | Turner | |
| 2009/0088327 A1* | 4/2009 | Rigatti et al. | 506/4 |
| 2010/0111768 A1* | 5/2010 | Banerjee et al. | 422/82.08 |
| 2010/0143900 A1 | 6/2010 | Peluso et al. | |

FOREIGN PATENT DOCUMENTS

| | | |
|---|---|---|
| DE | 10200025696 | 2/2006 |
| EP | 2233582 | 9/2010 |
| WO | 92/10587 | 6/1992 |
| WO | 02/02813 | 1/2002 |

* cited by examiner

*Primary Examiner* — Cynthia B Wilder
(74) *Attorney, Agent, or Firm* — Brent C. Moore; Illumina, Inc.

(57) ABSTRACT

The present technology relates to molecular sciences, such as genomics. More particularly, the present technology relates to nucleic acid sequencing.

30 Claims, 19 Drawing Sheets

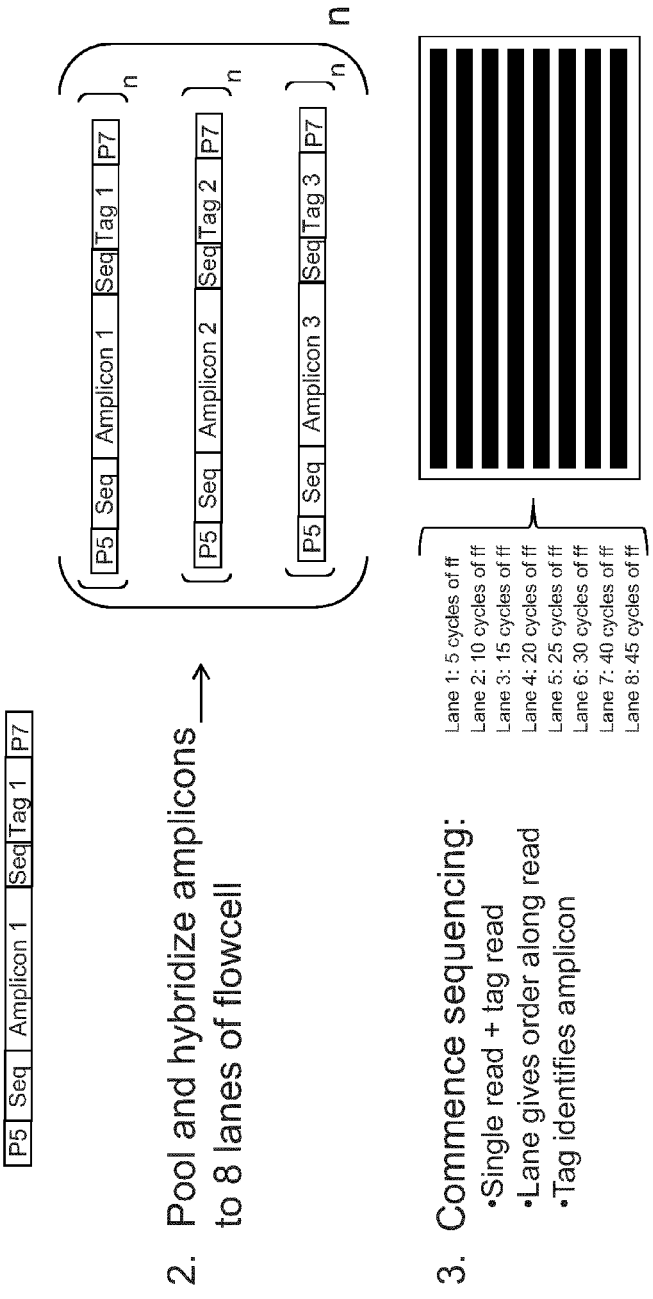

SEQUENCING METHODS

SEQUENCE LISTING

A sequence listing is attached hereto as Annex A.

FIELD OF THE INVENTION

The present technology relates to molecular sciences, such as genomics. More particularly, the present technology relates to nucleic acid sequencing.

BACKGROUND

The detection of specific nucleic acid sequences present in a biological sample has been used, for example, as a method for identifying and classifying microorganisms, diagnosing infectious diseases, detecting and characterizing genetic abnormalities, identifying genetic changes associated with cancer, studying genetic susceptibility to disease, and measuring response to various types of treatment. A common technique for detecting specific nucleic acid sequences in a biological sample is nucleic acid sequencing.

Nucleic acid sequencing methodology has evolved significantly from the chemical degradation methods used by Maxam and Gilbert and the strand elongation methods used by Sanger. Today several sequencing methodologies are in use which allow for the parallel processing of thousands of nucleic acids all in a single sequencing run. As such, the information generated from a single sequencing run can be enormous.

SUMMARY

Embodiments of the present invention relate to methods for obtaining nucleic acid sequence information. Some such methods include the steps of (a) providing a first sequencing reagent to a target nucleic acid in the presence of a polymerase, the first sequencing reagent including one or more nucleotide monomers, wherein the one or more nucleotide monomers pair with no more than three nucleotide types in the target, thereby forming a polynucleotide complementary to at least a portion of the target, and (b) providing a second sequencing reagent to the target nucleic acid, the second sequencing reagent including at least one nucleotide monomer, wherein the at least one nucleotide monomer of the second sequencing reagent includes a reversibly terminating moiety and wherein the second sequencing reagent is provided subsequent to providing the first sequencing reagent, whereby sequence information for at least a portion of the target nucleic acid is obtained.

Some embodiments of the above-described methods also include a step of identifying a homopolymer sequence of nucleotides in said target.

In some embodiments of the above-described methods, the one or more nucleotide monomers pair with at least two different nucleotide types in said target.

In some embodiments of the above-described methods, the first sequencing regent includes at least two different nucleotide monomers.

In some embodiments of the above-described methods, the one or more nucleotide monomers lack a reversibly terminating moiety.

Some embodiments of the above-described methods include removing unincorporated second sequencing reagent. Other embodiments include removing the reversibly terminating moiety.

Some embodiments of the above-described methods include providing a third sequencing reagent comprising at least one nucleotide monomer comprising a reversibly terminating moiety.

Some embodiments of the above-described methods include removing unincorporated first sequencing reagent prior to removing the reversibly terminating moiety.

Some embodiments of the above-described methods include providing a third sequencing reagent comprising at least one nucleotide monomer comprising a reversibly terminating moiety.

Additional embodiments of the above-described methods include repeating step (a) at least once prior to repeating step (b).

Some embodiments of the above-described methods include detecting incorporation of the at least one nucleotide monomer of the second sequencing reagent into said polynucleotide.

In some embodiments of the above-described methods, the detecting includes detecting a label. In other embodiments of the above-described methods, the detecting includes detecting pyrophosphate. In some such embodiments, detecting pyrophosphate can include, but is not limited to, detecting a signal that is produced in the presence of, by the incorporation of or by the degradation of pyrophosphate.

In some embodiments of the above-described methods, the at least one nucleotide monomer of the second sequencing reagent includes a label. In some such methods, the label is selected from the group consisting of fluorescent moieties, chromophores, antigens, dyes, phosphorescent groups, radioactive materials, chemiluminescent moieties, scattering or fluorescent nanoparticles, Raman signal generating moieties, and electrochemical detection moieties. Some embodiments, where the at least one nucleotide monomer of the second sequencing reagent includes a label, also include cleaving the label from the at least one nucleotide monomer of the second sequencing reagent.

In some embodiments of the above-described methods, the first sequencing reagent and the second sequencing reagent include nucleotide monomers selected from the group consisting of deoxyribonucleotides, modified deoxyribonucleotides, ribonucleotides, modified ribonucleotides, peptide nucleotides, modified peptide nucleotides, modified phosphate sugar backbone nucleotides and mixtures thereof.

In some embodiments of the above-described methods, the first sequencing reagent is provided to a single target nucleic acid.

In some embodiments of the above-described methods, the first sequencing reagent is provided simultaneously to a plurality of target nucleic acids. In some such methods, the plurality of target nucleic acids includes target nucleic acids having different nucleotide sequences.

In some embodiments of the above-described methods, the first sequencing reagent is provided in parallel to a plurality of target nucleic acids at separate features of an array. In some such embodiments, the plurality of target nucleic acids includes target nucleic acids having different nucleotide sequences.

In some embodiments of the above-described methods, the polymerase includes a polymerase selected from the group consisting of a DNA polymerase, an RNA polymerase, a reverse transcriptase, and mixtures thereof. In some such methods, the polymerase comprises a thermostable polymerase or a thermodegradable polymerase.

Additional methods for obtaining nucleic acid sequence information include the steps of (a) providing a first sequencing reagent to a target nucleic acid in the presence of a polymerase, the first sequencing reagent including a plurality of different nucleotide monomers, wherein at least one nucleotide monomer of the plurality of nucleotide monomers includes a reversibly terminating moiety, thereby forming a polynucleotide complementary to at least a portion of the target, (b) removing the reversibly terminating moiety of the at least one nucleotide monomer of the first sequencing reagent, and (c) providing a second sequencing reagent to the target nucleic acid, the second sequencing reagent including at least one nucleotide monomer, the at least one nucleotide monomer of said second sequencing reagent including a reversibly terminating moiety, wherein the second sequencing reagent is provided subsequent to providing the first sequencing reagent, whereby sequence information for at least a portion of the target nucleic acid is obtained.

Some embodiments of the above-described methods also include a step of identifying a homopolymer sequence of nucleotides in said target.

In some embodiments of the above-described methods, the one or more nucleotide monomers pair with at least two different nucleotides in said target.

In some embodiments of the above-described methods, the first sequencing regent includes at least two different nucleotide monomers.

In some embodiments of the above-described methods, the one or more nucleotide monomers lack a reversibly terminating moiety.

Some embodiments of the above-described methods include removing unincorporated first sequencing reagent. Other embodiments of the above-described methods include removing unincorporated second sequencing reagent.

Some embodiments of the above-described methods include removing the reversibly terminating moiety of the at least one nucleotide monomer of the second sequencing reagent.

Some embodiments of the above-described methods include providing a third sequencing reagent comprising at least one nucleotide monomer, the at least one nucleotide monomer of the third sequencing reagent comprising a reversibly terminating moiety.

Additional embodiments of the above-described methods include repeating steps (a)-(c).

Some embodiments of the above-described methods also include detecting incorporation of the at least one nucleotide monomer of the second sequencing reagent into the polynucleotide.

In some embodiments of the above-described methods, the detecting includes detecting a label. In other embodiments of the above-described methods, the detecting includes detecting pyrophosphate. In some such embodiments, detecting pyrophosphate can include, but is not limited to, detecting a signal that is produced in the presence of, by the incorporation of or by the degradation of pyrophosphate.

In some embodiments of the above-described methods, the at least one nucleotide monomer of said second sequencing reagent includes a label. In some such methods, the label is selected from the group consisting of fluorescent moieties, chromophores, antigens, dyes, phosphorescent groups, radioactive materials, chemiluminescent moieties, scattering or fluorescent nanoparticles, Raman signal generating moieties, and electrochemical detection moieties. Some embodiments, where the at least one nucleotide monomer of the second sequencing reagent includes a label, also include cleaving the label from the at least one nucleotide monomer of the second sequencing reagent.

In some embodiments of the above-described methods, the first sequencing reagent and the second sequencing reagent include nucleotide monomers selected from the group consisting of deoxyribonucleotides, modified deoxyribonucleotides, ribonucleotides, modified ribonucleotides, peptide nucleotides, modified peptide nucleotides, modified phosphate sugar backbone nucleotides and mixtures thereof.

In some embodiments of the above-described methods, the first sequencing reagent is provided to a single target nucleic acid.

In some embodiments of the above-described methods, the first sequencing reagent is provided simultaneously to a plurality of target nucleic acids. In some such methods, the plurality of target nucleic acids include target nucleic acids having different nucleotide sequences.

In some embodiments of the above-described methods, the first sequencing reagent is provided in parallel to a plurality of target nucleic acids at separate features of an array. In some such methods, the plurality of target nucleic acids include target nucleic acids having different nucleotide sequences.

In some embodiments of the above-described methods, the polymerase includes a polymerase selected from the group consisting of a DNA polymerase, an RNA polymerase, a reverse transcriptase, and mixtures thereof. In some such methods, the polymerase includes a thermostable polymerase or a thermodegradable polymerase.

Additional methods for obtaining nucleic acid sequence information include the steps of (a) providing a first sequencing reagent to a target nucleic acid in the presence of a ligase, wherein the first sequencing reagent includes at least one oligonucleotide, wherein the oligonucleotide includes a reversibly terminating moiety, (b) removing the reversibly terminating moiety of the at least one oligonucleotide of the first sequencing reagent, and (c) providing a second sequencing reagent to the target nucleic acid in the presence of a polymerase wherein the second sequencing reagent includes at least one nucleotide monomer, wherein the nucleotide monomer includes a reversibly terminating moiety, and wherein the second sequencing reagent is provided subsequent to providing the first sequencing reagent, whereby sequence information for at least a portion of the target nucleic acid is obtained.

Some embodiments of the above-described methods include removing unincorporated second sequencing reagent. Other embodiments of the above-described methods include removing the reversibly terminating moiety.

Some embodiments of the above-described methods include providing a third sequencing reagent comprising at least one nucleotide monomer comprising a reversibly terminating moiety.

Some embodiments of the above-described methods include removing unincorporated first sequencing reagent prior to removing the reversibly terminating moiety.

Some embodiments of the above-described methods include providing a third sequencing reagent comprising at least one nucleotide monomer comprising a reversibly terminating moiety.

Additional embodiments of the above-described methods include repeating step (a) at least once prior to repeating step (b).

Some embodiments of the above-described methods include detecting incorporation of the at least one nucleotide monomer of the second sequencing reagent into a polynucleotide complementary to the target nucleic acid.

In some embodiments of the above-described methods, the detecting includes detecting a label. In other embodiments of the above-described methods, the detecting includes detecting pyrophosphate. In some such embodiments, detecting pyrophosphate can include, but is not limited to, detecting a signal that is produced in the presence of, by the incorporation of or by the degradation of pyrophosphate.

In some embodiments of the above-described methods, the at least one nucleotide monomer of the second sequencing reagent includes a label. In some such methods, the label is selected from the group consisting of fluorescent moieties, chromophores, antigens, dyes, phosphorescent groups, radioactive materials, chemiluminescent moieties, scattering or fluorescent nanoparticles, Raman signal generating moieties, and electrochemical detection moieties. Some embodiments, where the at least one nucleotide monomer of the second sequencing reagent includes a label, also include cleaving the label from the at least one nucleotide monomer of the second sequencing reagent.

In some embodiments of the above-described methods, the second sequencing reagent includes nucleotide monomers selected from the group consisting of deoxyribonucleotides, modified deoxyribonucleotides, ribonucleotides, modified ribonucleotides, peptide nucleotides, modified peptide nucleotides, modified phosphate sugar backbone nucleotides and mixtures thereof.

In some embodiments of the above-described methods, the first sequencing reagent is provided to a single target nucleic acid.

In some embodiments of the above-described methods, the first sequencing reagent is provided simultaneously to a plurality of target nucleic acids. In some such methods, the plurality of target nucleic acids includes target nucleic acids having different nucleotide sequences.

In some embodiments of the above-described methods, the first sequencing reagent is provided in parallel to a plurality of target nucleic acids at individual features of an array. In some such methods, the plurality of target nucleic acids includes target nucleic acids having different nucleotide sequences.

In some embodiments of the above-described methods, the polymerase includes a polymerase selected from the group consisting of a DNA polymerase, an RNA polymerase, a reverse transcriptase, and mixtures thereof. In some such methods, the polymerase includes a thermostable polymerase or a thermodegradable polymerase.

Additional methods for obtaining nucleic acid sequence information include the steps of (a) providing a first sequencing reagent to a target nucleic acid in the presence of a polymerase, the first sequencing reagent including one or more nucleotide monomers, wherein the one or more nucleotide monomers pair with no more than three nucleotide types in the target, thereby forming a polynucleotide complementary to at least a portion of the target; and (b) providing a second sequencing reagent to the target nucleic acid, the second sequencing reagent including at least one nucleotide monomer, wherein the at least one nucleotide monomer pairs with no more than three nucleotide types in the target, wherein the second sequencing reagent is provided subsequent to providing the first sequencing reagent, and wherein a signal that indicates the incorporation of the at least one nucleotide monomer into the polynucleotide is generated, whereby sequence information for at least a portion of the target nucleic acid is obtained.

Some embodiments of the above-described methods also include a step of identifying a homopolymer sequence of nucleotides in said target.

In some embodiments of the above-described methods, the one or more nucleotide monomers pair with at least two different nucleotides in said target.

In some embodiments of the above-described methods, the first sequencing regent includes at least two different nucleotide monomers.

Some embodiments of the above-described methods include removing unincorporated second sequencing reagent.

Some embodiments of the above-described methods include providing a third sequencing reagent comprising at least one nucleotide monomer.

Some embodiments of the above-described methods include providing a third sequencing reagent comprising at least one nucleotide monomer, wherein the at least one nucleotide monomer is a nucleotide monomer not present in the second sequencing reagent.

Some embodiments of the above-described methods include removing the first sequencing reagent prior to the addition of the second sequencing regent.

Additional embodiments of the above-described methods include repeating step (a) at least once prior to repeating step (b).

In some embodiments of the above-described methods, the at least one nucleotide monomer of the second sequencing reagent includes no more than one nucleotide monomer. In other embodiments of the above-described methods, the at least one nucleotide monomer of the second sequencing reagent comprises no more than two different nucleotide monomers. In still other embodiments of the above-described methods, the at least one nucleotide monomer of the second sequencing reagent includes no more than three different nucleotide monomers.

In some embodiments of the above-described methods, the no more than two different nucleotide monomers of the second sequencing reagent are separately provided to said target nucleic acid.

Some embodiments of the above-described methods include detecting the signal. In some embodiments, the signal is produced by one or more labels, and thus, detection of the signal comprises detecting a label. In other embodiments, the signal is produced by or subsequent to the production or release of pyrophosphate. In such embodiments, the detecting includes detecting pyrophosphate or a signal that is produced in the presence of or by the consumption of pyrophosphate. For example, detecting pyrophosphate can include, but is not limited to, detecting a signal that is produced in the presence of, by the incorporation of or by the degradation of pyrophosphate.

In some embodiments of the above-described methods, the at least one nucleotide monomer of the second sequencing reagent includes a label. In some such methods, the label is selected from the group consisting of fluorescent moieties, chromophores, antigens, dyes, phosphorescent groups, radioactive materials, chemiluminescent moieties, scattering or fluorescent nanoparticles, Raman signal generating moieties, and electrochemical detection moieties. Some embodiments, where the at least one nucleotide monomer of the second sequencing reagent includes a label, also include cleaving the label from said at least one nucleotide monomer of said second sequencing reagent.

In some embodiments of the above-described methods, the first sequencing reagent and the second sequencing reagent include nucleotide monomers selected from the group consisting of deoxyribonucleotides, modified deoxyribonucleotides, ribonucleotides, modified ribonucleotides, peptide nucleotides, modified peptide nucleotides, modified phosphate sugar backbone nucleotides and mixtures thereof.

In some embodiments of the above-described methods, the first sequencing reagent is provided to a single target nucleic acid.

In some embodiments of the above-described methods, the first sequencing reagent is provided simultaneously to a plurality of target nucleic acids. In some such methods, the plurality of target nucleic acids can include target nucleic acids having different nucleotide sequences.

In some embodiments of the above-described methods, the first sequencing reagent is provided in parallel to a plurality of target nucleic acids at separate features of an array. In some such embodiments, the plurality of target nucleic acids includes target nucleic acids having different nucleotide sequences.

In some of the above-described methods, the polymerase includes a polymerase selected from the group consisting of a DNA polymerase, an RNA polymerase, a reverse transcriptase, and mixtures thereof. In some such methods, the polymerase includes a thermostable polymerase or a thermodegradable polymerase.

More methods for obtaining nucleic acid sequence information can include the steps of (a) providing a first low resolution sequence representation for a target nucleic acid, wherein the first low resolution sequence representation comprises an ordered series of determined regions and dark regions, wherein the determined regions comprise a sequence of at least two discrete nucleotides, wherein the dark regions are indicative of degenerate sequence composition, and wherein the dark regions intervene between said determined regions, (b) providing a second low resolution sequence representation for the target nucleic acid, wherein the second low resolution sequence representation comprises an ordered series of determined regions and dark regions, wherein the determined regions comprise a sequence of at least two discrete nucleotides, wherein the dark regions are indicative of degenerate sequence composition, and wherein the dark regions intervene between the determined regions and wherein the sequence of at least two discrete nucleotides in the first low resolution sequence representation is different from the sequence of at least two discrete nucleotides in the second low resolution sequence representation; and (c) comparing the first low resolution sequence representation and the second low resolution sequence representation to determine a sequence representation having a resolution higher than either the first low resolution sequences representation or second low resolution sequence representation alone.

In some embodiments of the above-described methods, the sequence representation having a resolution higher than either the first low resolution sequences representation or second low resolution sequence representation comprises the sequence of said target nucleic acid at single nucleotide resolution.

In some embodiments of the above-described methods, the dark regions are indicative of variable sequence length.

In some embodiments of the above-described methods, the sequence of at least two discrete nucleotides in the first low resolution sequence representation is no longer than two nucleotides.

In some embodiments of the above-described methods, the sequence of at least two discrete nucleotides in the second low resolution sequence representation is no longer than two nucleotides.

In some embodiments of the above-described methods, the sequence of at least two discrete nucleotides in the first low resolution sequence representation is three nucleotides.

In some embodiments of the above-described methods, the sequence of at least two discrete nucleotides in the second low resolution sequence representation is three nucleotides.

In some embodiments of the above-described methods, the dark region in the first low resolution sequence representation is degenerate with respect to a pair of nucleotide types.

In some embodiments of the above-described methods, the dark region in the second low resolution sequence representation is degenerate with respect to a pair of nucleotide types.

In some embodiments of the above-described methods, the dark region in the first low resolution sequence representation is degenerate with respect to a triplet of nucleotide types.

In some embodiments of the above-described methods, the dark region in the second low resolution sequence representation is degenerate with respect to a triplet of nucleotide types.

In some embodiments of the above-described methods, the determined regions comprise a sequence of at least two discrete nucleotides from the target nucleic acid.

In some embodiments of the above-described methods, the determined regions comprise a sequence of at least two discrete nucleotides that are complementary to nucleotides from the target nucleic acid.

In some embodiments of the above-described methods, pattern recognition methods are used to determine said actual sequence of the target nucleic acid at single nucleotide resolution.

In some embodiments of the above-described methods, the comparing is carried out by alignment of the first low resolution sequence representation and the second low resolution sequence to reference sequences in a database, wherein the reference sequences comprise the actual sequence of the target nucleic acid.

More embodiments include methods for determining the presence or absence of a target nucleic acid. Such methods can include the steps of: (a) providing a first low resolution sequence representation for a target nucleic acid, wherein the target nucleic acid is obtained from a first sample, wherein the first low resolution sequence representation comprises an ordered series of determined regions and dark regions, wherein the determined regions comprise a sequence of at least two discrete nucleotides, wherein the dark regions are indicative of degenerate sequence composition, and wherein the dark regions intervene between said determined regions, (b) providing a second low resolution sequence representation for a second target nucleic acid, wherein the second target nucleic acid is obtained from a reference sample and has the expected sequence as the target nucleic acid, wherein the second low resolution sequence representation comprises an ordered series of determined regions and dark regions, wherein the determined regions comprise a sequence of at least two discrete nucleotides, wherein the dark regions are indicative of degenerate sequence composition, and wherein the dark regions intervene between the determined regions and wherein the sequence of at least two discrete nucleotides in the first low resolution sequence representation is different from the sequence of at least two discrete nucleotides in the second low resolution sequence representation; and (c) comparing the first low resolution sequence representation and the second low resolution sequence representation to determine the presence or absence of the target nucleic acid in the target sample.

In some embodiments of the above-described methods, the sequence of at least two discrete nucleotides in the first low resolution sequence is the same as the sequence of at least two discrete nucleotides in the second low resolution sequence.

In some embodiments of the above-described methods, a first plurality of low resolution sequence representations for a plurality of nucleic acids in the target sample are provided and a second plurality of low resolution sequence representations for a plurality of second nucleic acids in said reference sample are provided.

In some embodiments of the above-described methods, the first low resolution sequence representation for the target nucleic acid and the second low resolution sequence representation for the second target nucleic acid are distinguished from low resolution sequence representations in the first plurality and in the second plurality.

Some embodiments of the above-described methods further comprise quantifying the amount of the target nucleic acid in the target sample relative to the amount of the target nucleic acid in the reference sample.

In some embodiments of the above-described methods, the target nucleic acid is an mRNA and the amount is indicative of an expression level for the mRNA.

In some embodiments of the above-described methods, the first and second low resolution sequence representations have a known correlation with the actual sequence of the target nucleic acid at single nucleotide resolution.

In some embodiments of the above-described methods, the first low resolution sequence representation and the second low resolution sequence representation are the same.

In some embodiments of the above-described methods, the target nucleic acid has been bisulfite converted to replace cytosines with uracils.

In some embodiments of the above-described methods, the step (c) further comprises comparing the first low resolution sequence representation and the second low resolution sequence representation to determine the presence of the target nucleic acid in the target sample and to identify the location of a methylated cytosine in the target nucleic acid.

Some embodiments of the present invention include methods for determining the presence of a target nucleic acid in a sample. Some embodiments of such methods include the steps of: (a) providing a barcode sequence from a target nucleic acid, wherein said target nucleic acid is obtained from said sample; and (b) comparing said barcode sequence with a reference sequence, wherein the target nucleic acid is present in said sample if said reference sequence comprises a region corresponding to each determined region of the bar code sequence.

Some embodiments of the above-described methods further comprise comparing the order of said determined regions of the bar code sequence with the order of corresponding regions in said reference sequence.

Some embodiments of the above-described methods further comprise comparing the average distance between said determined regions of the bar code sequence with the average distance between corresponding regions in said reference sequence.

In some embodiments of the above-described methods, the barcode sequence comprises a low resolution nucleic acid sequence representation.

In some embodiments of the above-described methods, the low resolution nucleic acid sequence representation comprises an ordered series of determined regions.

In some embodiments of the above-described methods, the low resolution nucleic acid sequence representation further comprises dark regions, wherein said dark regions are indicative of degenerate sequence composition, and wherein said dark regions intervene between said determined regions.

In some embodiments of the above-described methods, the sample is a metagenomic sample.

In some embodiments of the above-described methods, the reference sequence comprises a nucleic acid sequence.

In some embodiments of the above-described methods, the reference sequence is present in a database of reference sequences.

In some embodiments of the above-described methods, the reference sequences in said database are indexed by association with one or more groups of organisms.

Several embodiments of the present invention relate to methods for obtaining nucleic acid sequence information or otherwise sequencing nucleic acids. Some aspects of such methods relate to a method of generating overlapping sequencing reads. In some aspects the methods comprise providing a substrate having a surface, the surface comprising a site having a plurality of polynucleotides attached thereto and performing sequencing runs on the plurality of polynucleotides, the sequencing runs being initiated at different times such that the sequencing runs proceed for different durations, thereby generating a set of overlapping sequencing reads.

In some embodiments of the methods described herein, performing a sequencing run comprises: (a) providing a first sequencing reagent to a target nucleic acid in the presence of a polymerase, said first sequencing reagent comprising one or more nucleotide monomers, wherein said one or more nucleotide monomers pair with no more than three nucleotide types in said target, thereby forming a polynucleotide complementary to at least a portion of said target; and (b) providing a second sequencing reagent to said target nucleic acid, said second sequencing reagent comprising at least one nucleotide monomer, said at least one nucleotide monomer of said second sequencing reagent comprising a reversibly terminating moiety, wherein said second sequencing reagent is provided subsequent to providing said first sequencing reagent, whereby sequence information for at least a portion of said target nucleic acid is obtained.

In other embodiments of the methods described herein, performing a sequencing run comprises: (a) providing a first sequencing reagent to a target nucleic acid in the presence of a polymerase, said first sequencing reagent comprising a plurality of different nucleotide monomers, wherein at least one nucleotide monomer of said plurality of nucleotide monomers comprises a reversibly terminating moiety, thereby forming a polynucleotide complementary to at least a portion of said target; (b) removing the reversibly terminating moiety of said at least one nucleotide monomer of said first sequencing reagent; and (c) providing a second sequencing reagent to said target nucleic acid, said second sequencing reagent comprising at least one nucleotide monomer, said at least one nucleotide monomer of said second sequencing reagent comprising a reversibly terminating moiety, wherein said second sequencing reagent is provided subsequent to providing said first sequencing reagent, whereby sequence information for at least a portion of said target nucleic acid is obtained.

In still other embodiments of the methods described herein, performing a sequencing run comprises: (a) providing a first sequencing reagent to a target nucleic acid in the presence of a ligase, wherein the first sequencing reagent comprises at least one oligonucleotide, wherein said oligonucleotide comprises a reversibly terminating moiety; (b) removing the reversibly terminating moiety of said at least one oligonucleotide of said first sequencing reagent; and (c) providing a second sequencing reagent to said target nucleic acid in the presence of a polymerase wherein said second sequencing reagent comprises at least one nucleotide monomer, wherein said nucleotide monomer comprises a reversibly terminating moiety, and wherein said second sequencing reagent is provided subsequent to providing said first sequencing reagent, whereby sequence information for at least a portion of said target nucleic acid is obtained.

In yet other embodiments of the methods described herein, performing a sequencing run comprises: (a) providing a first sequencing reagent to a target nucleic acid in the presence of a polymerase, said first sequencing reagent comprising one or more nucleotide monomers, wherein said one or more nucleotide monomers pair with no more than three nucleotide types in said target, thereby forming a polynucleotide complementary to at least a portion of said target; and (b) providing a second sequencing reagent to said target nucleic acid, said second sequencing reagent comprising at least one nucleotide monomer, wherein said at least one nucleotide monomer pairs with no more than three nucleotide types in said target, wherein said second sequencing reagent is provided subsequent to providing said first sequencing reagent, and wherein a signal that indicates the incorporation of said at least one nucleotide monomer into the polynucleotide is generated, whereby sequence information for at least a portion of said target nucleic acid is obtained.

In some aspects, the methods further include assembling sequencing reads from the set of overlapping sequencing reads to obtain a contiguous nucleotide sequence of a nucleic acid of interest.

In some aspects of the sequencing methods described herein, providing the substrate includes hybridizing a plurality of template nucleic acids to a plurality of capture probes attached to the site and extending the capture probes, thereby producing a plurality of polynucleotides at the site. In some such embodiments, each template nucleic acid includes an adaptor that is complementary to a capture probe attached to the site. In other embodiments, initiating sequencing runs includes extending a sequencing primer, thereby producing extended strands.

In some embodiments of the sequencing methods described herein, the plurality of polynucleotides includes copies of the same fragment of a nucleic acid of interest. In certain aspects, the copies include oligonucleotide adaptors at each end. In one aspect, each copy further includes a different sequencing primer site. In another aspect, the copies further include an index tag, wherein copies having the same index tag are copies of the same fragment of the nucleic acid of interest.

In some of the nucleic acid sequencing methods described herein, initiating sequencing runs includes providing, at different times, sequencing primers that are complementary to the different sequencing primer sites. In some aspects of such methods, the index tag identifies sequencing reads derived from the same fragment of the nucleic acid of interest.

In certain embodiments, the plurality of polynucleotides further includes copies of different fragments of the nucleic acid of interest. In some aspects, the copies of different fragments include different index tags. In such aspects, the copies of different fragments are identified by the sequence of the different index tags.

Additional aspects of the present methods described herein relate to generating overlapping sequencing reads wherein the methods comprise providing a substrate having a surface, the surface comprising a first site and a second site, the first and second sites having a plurality of polynucleotides attached thereto and the first and second sites being spatially segregated from each other; and performing a sequencing run on the plurality of polynucleotides no as to produce an extended strand at the first and second spatially segregated sites, wherein the length of the extended strand produced at the first site is different from the length of the extended strand produced at the second site, thereby generating a set of overlapping sequencing reads.

In some embodiments of the methods described herein, performing a sequencing run comprises: (a) providing a first sequencing reagent to a target nucleic acid in the presence of a polymerase, said first sequencing reagent comprising one or more nucleotide monomers, wherein said one or more nucleotide monomers pair with no more than three nucleotide types in said target, thereby forming a polynucleotide complementary to at least a portion of said target; and (b) providing a second sequencing reagent to said target nucleic acid, said second sequencing reagent comprising at least one nucleotide monomer, said at least one nucleotide monomer of said second sequencing reagent comprising a reversibly terminating moiety, wherein said second sequencing reagent is provided subsequent to providing said first sequencing reagent, whereby sequence information for at least a portion of said target nucleic acid is obtained.

In some embodiments of the methods described herein, performing a sequencing run comprises: (a) providing a first sequencing reagent to a target nucleic acid in the presence of a polymerase, said first sequencing reagent comprising a plurality of different nucleotide monomers, wherein at least one nucleotide monomer of said plurality of nucleotide monomers comprises a reversibly terminating moiety, thereby forming a polynucleotide complementary to at least a portion of said target; (b) removing the reversibly terminating moiety of said at least one nucleotide monomer of said first sequencing reagent; and (c) providing a second sequencing reagent to said target nucleic acid, said second sequencing reagent comprising at least one nucleotide monomer, said at least one nucleotide monomer of said second sequencing reagent comprising a reversibly terminating moiety, wherein said second sequencing reagent is provided subsequent to providing said first sequencing reagent, whereby sequence information for at least a portion of said target nucleic acid is obtained.

In still some embodiments of the methods described herein, performing a sequencing run comprises: (a) providing a first sequencing reagent to a target nucleic acid in the presence of a ligase, wherein the first sequencing reagent comprises at least one oligonucleotide, wherein said oligonucleotide comprises a reversibly terminating moiety; (b) removing the reversibly terminating moiety of said at least one oligonucleotide of said first sequencing reagent; and (c) providing a second sequencing reagent to said target nucleic acid in the presence of a polymerase wherein said second sequencing reagent comprises at least one nucleotide monomer, wherein said nucleotide monomer comprises a reversibly terminating moiety, and wherein said second sequencing reagent is provided subsequent to providing said first sequencing reagent, whereby sequence information for at least a portion of said target nucleic acid is obtained.

In still other embodiments of the methods described herein, performing a sequencing run comprises: (a) providing a first sequencing reagent to a target nucleic acid in the presence of a polymerase, said first sequencing reagent comprising one or more nucleotide monomers, wherein said one or more nucleotide monomers pair with no more than three nucleotide types in said target, thereby forming a polynucleotide complementary to at least a portion of said target; and (b) providing a second sequencing reagent to said target nucleic acid, said second sequencing reagent comprising at least one nucleotide monomer, wherein said at least one nucleotide monomer pairs with no more than three nucleotide types in said target, wherein said second sequencing reagent is provided subsequent to providing said first sequencing reagent, and wherein a signal that indicates the incorporation of said at least one nucleotide monomer into the polynucleotide is generated, whereby sequence information for at least a portion of said target nucleic acid is obtained.

In some aspects, the methods further include assembling sequencing reads from the set of overlapping sequencing reads to obtain a contiguous nucleotide sequence of a nucleic acid of interest.

In some aspects, providing the substrate includes hybridizing a plurality of template nucleic acids to a plurality of capture probes attached to the site and extending the capture probes, thereby producing a plurality of polynucleotides at the site. In some such embodiments, each template nucleic acid includes an adaptor that is complementary to a capture probe attached to the site. In other embodiments, initiating sequencing runs includes extending a sequencing primer, thereby producing extended strands.

In some embodiments, the plurality of polynucleotides includes copies of the same fragment of a nucleic acid of interest. In certain aspects, the copies include oligonucleotide adaptors at each end. In one aspect, each copy further includes the same sequencing primer site. In another aspect, the copies further include an index tag, wherein copies having the same index tag are copies of the same fragment of the nucleic acid of interest.

In several embodiments, initiating sequencing runs includes providing a sequencing primer that is complementary to the sequencing primer site to the first and second spatially segregated sites. In one aspect, the sequencing primer is provided to the first and second spatially segregated sites at the same time. In another aspect, the sequencing primer is provided to the first and second spatially segregated sites at different times. In certain aspects, the plurality of polynucleotides further includes copies of different fragments of the nucleic acid of interest. The copies of different fragments can include different index tags and the copies of different fragments can be identified by the sequence of the different index tags.

Additional embodiments of the sequencing methods described herein relate to provision of a substrate having a surface. In some embodiments, the substrate includes a flow chamber. In some embodiments, the surface of the substrate is planer. In other embodiments, the surface of the substrate is patterned. In still other embodiments, the surface includes a channel in a flow chamber.

Further embodiments of the sequencing methods described herein relate to provision of a substrate having a surface comprising sites. In some embodiments, a site can include a well. In some embodiments, sites can include a bead in a well.

Additional aspects of generating overlapping sequencing reads can be found in U.S. Provisional Patent Application No. 61/387,900, entitled COMPOSITIONS AND METHOD FOR SEQUENCING NUCLEIC ACIDS, filed Sep. 29, 2010, which is incorporated herein by reference in its entirety.

BRIEF DESCRIPTION OF THE DRAWINGS

FIG. 12 is a schematic illustration showing a method of generating overlapping sequencing reads and obtaining a contiguous nucleotide sequence of a nucleic acid of interest by performing limited extensions (fast forwarding) from different sequencing primers.

FIG. 13 is a schematic illustration showing a method of generating overlapping sequence reads and obtaining a contiguous nucleotide sequence of a nucleic acid of interest by fast forward sequencing from the same sequencing primer initiated at different locations (lanes) on a surface of a substrate.

DETAILED DESCRIPTION

Figure 1A:
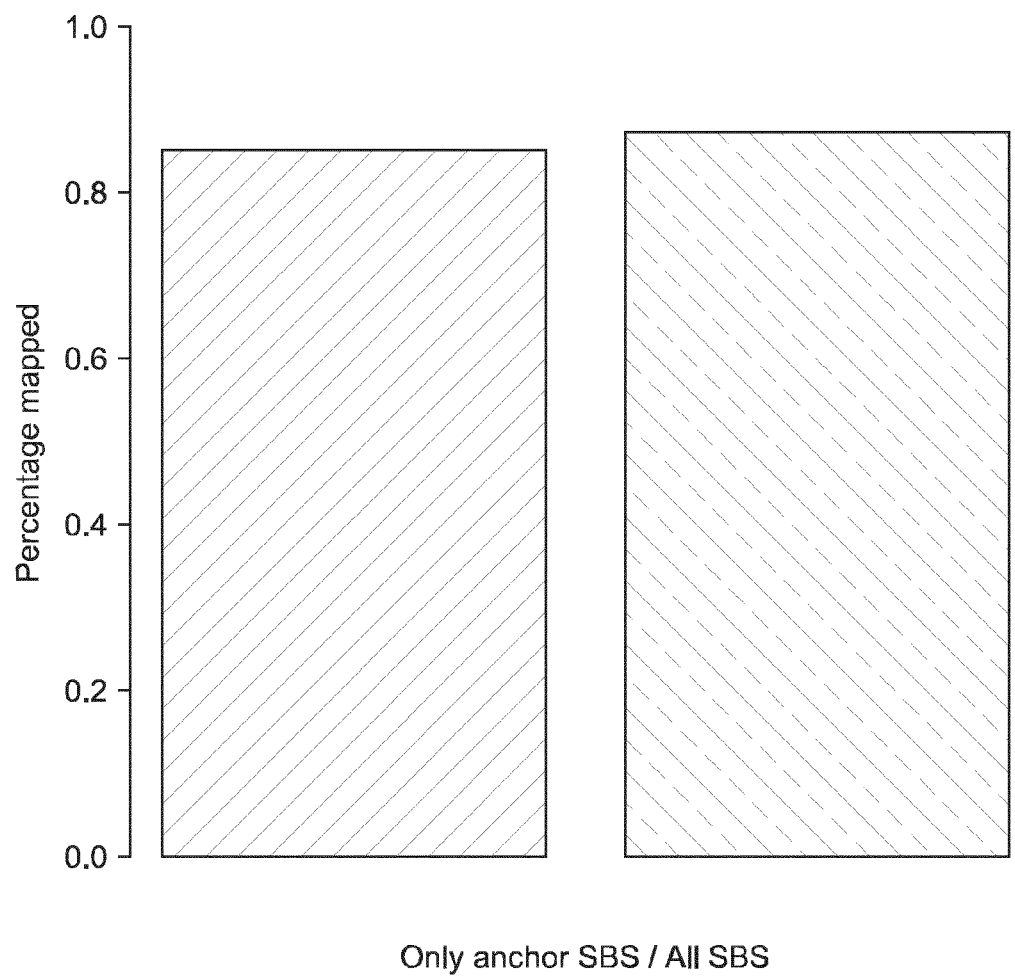
FIG. 1A shows a graph of the percentage of sequences that were obtained using computer simulations for limited extension sequencing methods and that were mapped to specific locations in the *Arabidopsis* genome. Sequences were obtained from: (1) the first interval of twenty-five SBS cycles (anchor only); or (2) all intervals of SBS cycles (all SBS). Y-axis shows 100% as 1.0.

Aspects of the present invention relate to methods for obtaining nucleic acid sequence information of a target nucleic acid. Some of the methods described herein relate to obtaining a molecular signature of a target nucleic acid, where the molecular signature includes a low resolution representation of the target nucleic acid sequence. Some embodiments of these methods can be employed with nucleotide monomers while others utilize oligonucleotides. When oligonucleotides are used, one or more of the oligonucleotides can include a reversibly terminating moiety. In embodiments where nucleotide monomers are used, one or more of the nucleotide monomers can include a reversibly terminating moiety. For example, an embodiment which utilizes nucleotide monomers can include the steps of (a) providing a first sequencing reagent to a target nucleic acid in the presence of a polymerase, the first sequencing reagent including one or more nucleotide monomers, wherein the one or more nucleotide monomers pair with no more than three nucleotide types in the target, thereby forming a polynucleotide complementary to at least a portion of the target, and (b) providing a second sequencing reagent to the target nucleic acid, the second sequencing reagent including at least one nucleotide monomer, wherein the at least one nucleotide monomer of the second sequencing reagent includes a reversibly terminating moiety, wherein the second sequencing reagent is provided subsequent to providing the first sequencing reagent, whereby sequence information for at least a portion of the target nucleic acid is obtained.

While the methods described herein can be used for the de novo sequencing of a target nucleic acid, in preferred embodiments, the methods can produce a molecular signature that may be compared with other signatures and predicted signatures. In some embodiments, the signature need not provide a nucleotide sequence at single nucleotide resolution. Rather, the signature can provide a unique identification of a nucleic acid based on a low resolution sequence of the nucleic acid. The low resolution sequence can be, for example, degenerate with respect to the identity of the nucleotide type at one or more position in the nucleotide sequence of the nucleic acid. Accordingly, the sequence information that can be obtained using the methods described herein can be used in applications involved in genotyping, expression profiling, capturing alternative splicing, genome mapping, amplicon sequencing, methylation detection and metagenomics.

DEFINITIONS

As used herein, "oligonucleotide" and/or "nucleic acid" and/or grammatical equivalents thereof can refer to at least two nucleotide monomers linked together. A nucleic acid can generally contain phosphodiester bonds, however, in some embodiments, nucleic acid analogs may have other types of backbones, comprising, for example, phosphoramide (Beaucage, et al., Tetrahedron, 49:1925 (1993); Letsinger, J. Org. Chem., 35:3800 (1970); Sprinzl, et al., Eur. J. Biochem., 81:579 (1977); Letsinger, et al., Nucl. Acids Res., 14:3487 (1986); Sawai, et al., Chem. Lett., 805 (1984), Letsinger, et al., J. Am. Chem. Soc., 110:4470 (1988); and Pauwels, et al., Chemica Scripta, 26:141 (1986), incorporated by reference in their entireties), phosphorothioate (Mag, et al., Nucleic Acids Res., 19:1437 (1991); and U.S. Pat. No. 5,644,048), phosphorodithioate (Briu, et al., J. Am. Chem. Soc., 111:2321 (1989), incorporated by reference in its entirety), O-methylphosphoroamidite linkages (see Eckstein, Oligonucleotides and Analogues: A Practical Approach, Oxford University Press, incorporated by reference in its entirety), and peptide nucleic acid backbones and linkages (see Egholm, J. Am. Chem. Soc., 114:1895 (1992); Meier, et al., Chem. Int. Ed. Engl., 31:1008 (1992); Nielsen, Nature, 365:566 (1993); Carlsson, et al., Nature, 380:207 (1996), incorporated by reference in their entireties).

Other analog nucleic acids include those with positive backbones (Denpcy, et al., Proc. Natl. Acad. Sci. USA, 92:6097 (1995), incorporated by reference in its entirety); non-ionic backbones (U.S. Pat. Nos. 5,386,023; 5,637,684; 5,602,240; 5,216,141; and 4,469,863; Kiedrowshi, et al., Angew. Chem. Intl. Ed. English, 30:423 (1991); Letsinger, et al., J. Am. Chem. Soc., 110:4470 (1988); Letsinger, et al., Nucleosides & Nucleotides, 13:1597 (1994); Chapters 2 and 3, ASC Symposium Series 580, "Carbohydrate Modifications in Antisense Research", Ed. Y. S. Sanghui and P. Dan Cook; Mesmaeker, et al., Bioorganic & Medicinal Chem. Lett., 4:395 (1994); Jeffs, et al., J. Biomolecular NMR, 34:17 (1994); Tetrahedron Lett., 37:743 (1996), incorporated by reference in their entireties) and non-ribose (U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Coo, incorporated by reference in their entireties). Nucleic acids may also contain one or more carbocyclic sugars (see Jenkins, et al., Chem. Soc. Rev., (1995) pp. 169 176).

Modifications of the ribose-phosphate backbone may be done to facilitate the addition of additional moieties such as labels, or to increase the stability of such molecules under certain conditions. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, for example, genomic or cDNA, RNA or a hybrid. A nucleic acid can contain any combination of deoxyribo- and ribo-nucleotides, and any combination of bases, including uracil, adenine, thymine, cytosine, guanine, inosine, xanthanine, hypoxanthanine, isocytosine, isoguanine, and base analogs such as nitropyrrole (including 3-nitropyrrole) and nitroindole (including 5-nitroindole), etc.

In some embodiments, a nucleic acid can include at least one promiscuous base. Promiscuous bases can base-pair with more than one different type of base. In some embodiments, a promiscuous base can base-pair with at least two different types of bases and no more than three different types of bases. An example of a promiscuous base includes inosine that may pair with adenine, thymine, or cytosine. Other examples include hypoxanthine, 5-nitroindole, acylic 5-nitroindole, 4-nitropyrazole, 4-nitroimidazole and 3-nitropyrrole (Loakes et al., Nucleic Acid Res. 22:4039 (1994); Van Aerschot et al., Nucleic Acid Res. 23:4363 (1995); Nichols et al., Nature 369:492 (1994); Berstrom et al., Nucleic Acid Res. 25:1935 (1997); Loakes et al., Nucleic Acid Res. 23:2361 (1995); Loakes et al., J. Mol. Biol. 270:426 (1997); and Fotin et al., Nucleic Acid Res. 26:1515 (1998), incorporated by reference in their entireties). Promiscuous bases that can base-pair with at least three, four or more types of bases can also be used.

As used herein, "nucleotide monomer" and/or grammatical equivalents thereof can refer to a nucleotide or nucleotide analog that can become incorporated into a polynucleotide. In the methods described herein, the nucleotide monomers are separate non-linked nucleotides. That is, the nucleotide monomers are not present as dimers, trimers, etc. Such nucleotide monomers may be substrates for an enzyme that may extend a polynucleotide strand. Nucleotide monomers may or may not become incorporated into a nascent polynucleotide in a flow step. Nucleotide monomers may or may not contain label moieties and/or terminator moieties. Terminator moieties include reversibly terminating moieties. Incorporation of a nucleotide monomer comprising a reversibly terminating moieties can inhibit extension of the polynucleotide, however, the moiety can be removed and the polynucleotide may be extended further. Such reversibly terminating moieties are well known in the art. Examples of nucleotide monomers include deoxyribonucleotides, modified deoxyribonucleotides, ribonucleotides, modified ribonucleotides, peptide nucleotides, modified peptide nucleotides, modified phosphate sugar backbone nucleotides and mixtures thereof. Nucleotide analogs which include a modified nucleobase can also be used in the methods described herein. Examples of bases are described herein, including promiscuous bases. As is known in the art, certain nucleotide analogues cannot become incorporated into a polynucleotide, for example, nucleotide analogues such as adenosine 5' phosphosulfate. A nucleotide monomer may comprise a label moiety and/or a terminator moiety.

As used herein, "sequencing reagent" and grammatical equivalents thereof can refer to a composition, such as a solution, comprising one or more precursors of a polymer such as nucleotide monomers. In some embodiments, a sequencing reagent includes one or more nucleotide monomers having a label moiety, a terminator moiety, or both. Such moieties are chemical groups that are not naturally occurring moieties of nucleic acids, being introduced by synthetic means to alter the natural characteristics of the nucleotide monomers with regard to detectability under particular conditions or enzymatic reactivity under particular conditions. Alternatively, a sequencing reagent comprises one or more nucleotide monomers that lack a label moiety and/or a terminator moiety. In some embodiments, the sequencing reagent consists of or consists essentially of one nucleotide monomer type, two different nucleotide monomer types, three different nucleotide monomer types or four different nucleotide monomer types. "Different" nucleotide monomer types are nucleotide monomers that have different base moieties. Two or more nucleotide monomer types can have other moieties, such as those set forth above, that are the same as each other or different from each other.

For ease of illustration, various methods and compositions are described herein with respect to multiple nucleotide monomers. It will be understood that the multiple nucleotide monomers of these methods or compositions can be of the same or different types unless explicitly indicated otherwise. It should be understood that when providing a sequencing reagent comprising multiple nucleotide monomers to a target nucleic acid, the nucleotide monomers do not necessarily have to be provided at the same time. However, in preferred embodiments of the methods described herein, multiple nucleotide monomers are provided together (at the same time) to the target nucleic acid. Irrespective of whether the multiple nucleotide monomers are provided to the target nucleic acid separately or together, the result is that the sequencing reagent, including the nucleotide monomers contained therein, are simultaneously in the presence of the target nucleic acid. For example, two nucleotide monomers can be delivered, either together or separately, to a target nucleic acid. In such embodiments, a sequencing reagent comprising two nucleotide monomers will have been provided to the target nucleic acid. In some embodiments, zero, one or two of the nucleotide monomers will be incorporated into a polynucleotide that is complementary to the target nucleic acid. In some embodiments, a sequencing reagent may comprise an oligonucleotide that may be incorporated into a polymer. The oligonucleotide may comprise a terminator moiety and/or a label moiety.

As used herein, "complementary polynucleotides" includes polynucleotide strands that are not necessarily complementary to the full length of the target sequence. That is, a complementary polynucleotide can be complementary to only a portion of the target nucleic acid. As more nucleotide monomers are incorporated into the complementary polynucleotide, the complementary polynucleotide becomes complementary to a greater portion of the target nucleic acid. Typically, the complementary portion is a contiguous portion of the target nucleic acid.

As used herein, "a round of sequencing" or "a sequencing run" and/or grammatical variants thereof refers to a repetitive process of physical or chemical steps that is carried out to obtain signals indicative of the order of monomers in a polymer. The signals can be indicative of an order of monomers at single monomer resolution or lower resolution. In particular embodiments, the steps can be initiated on a nucleic acid target and carried out to obtain signals indicative of the order of bases in the nucleic acid target. The process can be carried out to its typical completion, which is usually defined by the point at which signals from the process can no longer distinguish bases of the target with a reasonable level of certainty. If desired, completion can occur earlier, for example, once a desired amount of sequence information has been obtained. A sequencing run can be carried out on a single target nucleic acid molecule or simultaneously on a population of target nucleic acid molecules having the same sequence, or simultaneously on a population of target nucleic acids having different sequences. In some embodiments, a sequencing run is terminated when signals are no longer obtained from one or more target nucleic acid molecules from which signal acquisition was initiated. For example, a sequencing run can be initiated for one or more target nucleic acid molecules that are present on a solid phase substrate and terminated upon removal of the one or more target nucleic acid molecules from the substrate. Sequencing can be terminated by otherwise ceasing detection of the target nucleic acids that were present on the substrate when the sequencing run was initiated.

As used herein, "cycle" and/or grammatical variants thereof refers to the portion of a sequencing run that is repeated to indicate the presence of at least one monomer in a polymer. Typically, a cycle includes several steps such as steps for delivery of reagents, washing away unreacted reagents and detection of signals indicative of changes occurring in response to added reagents. For example, a cycle of a sequencing-by-synthesis (SBS) reaction can include delivery of a sequencing reagent that includes one or more type of nucleotide, washing to remove unreacted nucleotides, and detection to detect one or more nucleotides that are incorporated in an extended nucleic acid. In addition, "cycle" and/or grammatical variants thereof can refer to the portion of a sequencing run that is repeated to extend a polynucleotide complementary to a target nucleic acid. For example, a cycle can include several steps such as the delivery of first reagent, washing away unreacted agents, and delivery of a second reagent. Typically, such delivery steps can be for limited extension of a polynucleotide complementary to a target nucleic acid. In such embodiments, the polynucleotide strand may be extended in each delivery step by at least 0, 1, 2, 3, 4, 5, 6, 7, 8, 9, 10, 15, 20, 25, 30, 35, 40, 45, 50, 60, 70, 80, 90, 100, 150, 200, 250, 300, 350, 400, 450, 500, 600, 700, 800, 900, 1000, 1500, 2000, 2500, 3000, 3500, 4000, 4500, 5000, 6000, 7000, 8000, 9000, 10,000 or more than 10,000 nucleotides.

As used herein, "flow step" and/or "delivery" and/or grammatical equivalents thereof can refer to providing a sequencing reagent to a target polymer such as a target nucleic acid. In some embodiments, the sequencing reagent contains one or more nucleotide monomers. Flow steps or deliveries can be repeated in multiple cycles in a round of sequencing.

As used herein, "a portion" and "at least a portion" and grammatical equivalents thereof refers to any fraction of a whole amount. In some embodiments, "at least a portion" can refer to at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99%, 99.9% or 100% of a whole amount.

As used herein, "sequence representation" and/or grammatical equivalents thereof, when used in reference to a polymer, refers to information that signifies the order and type of monomeric units in the polymer. For example, the information can indicate the order and type of nucleotides in a nucleic acid. The information can be in any of a variety of formats including, for example, a depiction, image, electronic medium, series of symbols, series of numbers, series of letters, series of colors, etc. The information can be at single monomer resolution or at lower resolution, as set forth in further detail below. An exemplary polymer is a nucleic acid, such as DNA or RNA, having nucleotide units. A series of "A," "T," "G," and "C" letters is a well known sequence representation for DNA that can be correlated, at single nucleotide resolution, with the actual sequence of a DNA molecule. Other exemplary polymers are proteins having amino acid units and polysaccharides having saccharide units.

As used herein, "low resolution" and grammatical equivalents thereof, when used in reference to a sequence representation, means providing less information on the order and type of monomers in a polymer than provided by a single monomer resolution sequence representation of the same polymer. The term can refer to a resolution at which at least one type of monomeric unit in a polymer can be distinguished from at least a first other type of monomeric unit in the polymer, but cannot necessarily be distinguished from a second other type of monomeric unit in the polymer. For example, "low resolution" when used in reference to a sequence representation of a nucleic acid means that two or three of four possible nucleotide types can be indicated as candidate residents at any particular position in the sequence while the two or three nucleotide types cannot necessarily be distinguished from each other in any and all of the sequence representation or in a portion of the sequence representation. The portion can be a contiguous portion representing at least 0, 1, 2, 3, 4, 5, 6, 7, 8, 9, 10, 15, 20, 25, 30, 35, 40, 45, 50, 60, 70, 80, 90, 100, 150, 200, 250, 300, 350, 400, 450, 500, 600, 700, 800, 900, 1000, 1500, 2000, 2500, 3000, 3500, 4000, 4500, 5000, 6000, 7000, 8000, 9000, 10,000 or more than 10,000 nucleotides of the nucleic acid. In particular embodiments, two different monomeric units from an actual polymer sequence can be assigned a common label or identifier in a low resolution sequence representation. In some embodiments, three different monomeric units from an actual polymer sequence can be assigned a common label or identifier in a low resolution sequence representation. Typically, the diversity of different characters in a low resolution sequence representation will be fewer than the diversity of different types of monomers in the polymer represented by the low resolution sequence representation. For example, a low resolution representation of a nucleic acid can include a string of symbols and the number of different symbol types in the string can be less than the number of different nucleotide types in the actual sequence of the nucleic acid. In some examples, a low resolution sequence representation can include regions where the identity and/or number of monomeric units is unknown. For example, a sequence representation can include a sequence of distinguishable monomeric units interspersed with symbols representing regions of unknown length and content.

As used herein "position" and grammatical equivalents thereof, when used in reference to a sequence of units, refers to the location of a unit in the sequence. The location can be identified using information that is independent of the type of unit that occupies the location. The location can be identified, for example, relative to other locations in the same sequence. Alternatively or additionally, the location can be identified with reference to another sequence or series. Although one or more characteristic of the unit may be known, any such characteristics need not be considered in identifying position.

As used herein the term "type," when used in reference to a monomer, nucleotide or other unit of a polymer, is intended to refer to the species of monomer, nucleotide or other unit. The type of monomer, nucleotide or other unit can be identified independent of their positions in the polymer. Similarly, when used in reference to a symbol or other identifier in a sequence representation, the term is intended to refer to the species of symbol or identifier and can be independent of their positions in the sequence representation. Exemplary types of nucleotide monomers are those having either adenine (A), cytosine (C), guanine ((3), thymine (T), or uracil (U). Among the nucleotide monomers having cytosine are included those that are methylated at the 5-position, such as 5-methyl cytosine or 5-hydroxymethyl cytosine, and those that are not methylated at the 5-position.

As used herein, "degenerate" and/or grammatical equivalents thereof means having more than one state or more than one identification. The term can be used to refer to one way ambiguity in which an identifier is correlated to two or more states but any particular state is correlated to only one identifier. Alternatively or additionally, the term can be used to refer to two way ambiguity in which an identifier is correlated to two or more states and at least one of those states is correlated to more than one identifier. When used in reference to a nucleic acid representation, the term refers to a position in the nucleic acid representation for which two or more nucleotide types are identified as candidate occupants in the corresponding position of the actual nucleic acid sequence. A degenerate position in a nucleic acid can have, for example, 2, 3 or 4 nucleotide types as candidate occupants. In particular embodiments, the number of different nucleotide types at a degenerate position in a sequence representation can be greater than one and less than three, namely, two. In other embodiments, the number of different nucleotide types at a degenerate position in a sequence representation can be greater than one and less than four, namely, two or three. Typically, the number of different nucleotide types at a degenerate position in a sequence representation can be less than the number of different nucleotide types present in the actual nucleic acid sequence that is represented. A sequence representation that is degenerate can have one way ambiguity such that a particular symbol present in a sequence representation for a nucleic acid is correlated to two or more candidate nucleotide types in the nucleic acid but any particular nucleotide type is correlated to only one type of symbol in the sequence representation. Alternatively or additionally, a sequence representation can have two way ambiguity in which a particular symbol type is correlated to two or more nucleotide types and at least one of those nucleotide types is correlated to more than one type of symbol.

As used herein, "limited extension" and/or grammatical equivalents thereof can refer to the incorporation of nucleotide monomers into a polynucleotide complementary to a target nucleic acid of at least 0, 1, 2, 3, 4, 5, 6, 7, 8, 9, 10, 15, 20, 25, 30, 35, 40, 45, 50, 60, 70, 80, 90, 100, 150, 200, 250, 300, 350, 400, 450, 500, 600, 700, 800, 900, 1000, 1500, 2000, 2500, 3000, 3500, 4000, 4500, 5000, 6000, 7000, 8000, 9000, 10,000 or more than 10,000 nucleotide monomers. In some embodiments, "limited extension" can refer to the incorporation of a number of nucleotide monomers into a polynucleotide equivalent to at least the number of nucleotides in a target nucleic acid complementary to the target nucleic acid. In some embodiments, performing a limited extension can include delivering a sequencing reagent to a target nucleic acid in the presence of a polymerase, where the sequencing reagent includes at least one nucleotide monomer comprising a terminator moiety. In preferred embodiments the terminator moiety can be a reversibly terminating moiety. In some embodiments, performing a limited extension can include delivering a sequencing reagent to a target nucleic acid in the presence of a polymerase, where the sequencing reagent lacks at least one type of nucleotide monomer. In some embodiments, performing a limited extension can include delivering a sequencing reagent to a target nucleic acid in the presence of a ligase, where the sequencing reagent includes at least one oligonucleotide comprising a terminator moiety, where the at least one oligonucleotide can be ligated to a polynucleotide complementary to a target nucleic acid to extend the polynucleotide complementary to a target nucleic acid. In preferred embodiments, the terminator moiety can be a reversibly terminating moiety.

As used herein, "limited dark extension" and/or grammatical equivalents thereof can refer to a limited extension step, where the identity of nucleotide monomers that may be incorporated at specific positions into a polynucleotide complementary to a target nucleic acid may not known. In some embodiments, a limited dark extension can include performing a limited extension, where incorporation of nucleotide monomers may not be measured. For example, limited dark extension can proceed under conditions in which one or more types of nucleotide monomers are incorporated without being detected, two or more types of nucleotide monomers are incorporated without being detected, three or more types of nucleotide monomers are incorporated without being detected, or four or more types of nucleotide monomers are incorporated without being detected. Alternatively or additionally, limited dark extension can proceed under conditions in which four or fewer types of nucleotide monomers are incorporated without being detected, three or fewer types of nucleotide monomers are incorporated without being detected, two or fewer types of nucleotide monomers are incorporated without being detected, or no more than type of nucleotide monomer is incorporated without being detected.

As used herein, "limited read extension" and/or grammatical equivalents thereof can refer to a limited extension step, where the identity of nucleotide monomers that may be incorporated at specific positions into a polynucleotide complementary to a target nucleic acid may be known. In some embodiments, the identity of incorporated nucleotide monomers may be known at low resolution. For example, the identity of an incorporated nucleotide may be distinguished from at least one other type of nucleotide. In some embodiments, performing a limited read extension can include performing a limited extension, and measuring the incorporation of nucleotide monomers into a polynucleotide strand complementary to a target nucleic acid. For example, limited read extension can proceed under conditions in which the identity of 4 or fewer nucleotide monomer types at any given position are distinguished, the identity of 3 or fewer nucleotide monomer types at any given position are distinguished, the identity of 2 or fewer nucleotide monomer types at any given position are distinguished, or the identity of 1 nucleotide monomer type at any given position is distinguished. Alternatively or additionally, limited read extension can proceed under conditions in which one or more nucleotide monomer types at any given position are distinguished, two or more nucleotide monomer types at any given position are distinguished, three or more nucleotide monomer types at any given position are distinguished, or four or more nucleotide monomer types at any given position are distinguished.

As used herein, "fast forwarding," "fast forward sequencing," and/or grammatical equivalents thereof refers to sequencing which includes a number of limited polynucleotide extensions as described further herein.

Some of the methods described herein for obtaining nucleic acid sequencing of a target nucleic acid can include performing iterations of at least one limited dark extension step and at least one limited read extension step. It will be understood that the at least one limited dark extension step and at least one limited read extension can be performed in any order, that is, at least one limited dark extension step may occur before or after at least one limited read extension step. Sequence information obtained using iterations of at least one limited dark extension step and at least one limited read extension step can produce a molecular signature for a target nucleic acid that is predictable and informative. Methods for limited dark extension and limited read extension include methods for limited extension of a polynucleotide as described herein.

Methods for Limited Extension of a Polynucleotide
Lack of at Least One Nucleotide Monomer Disclosed herein are methods that can be used for limited extension of a polynucleotide complementary to a target nucleic acid. In some embodiments, performing a limited extension can include delivering a sequencing reagent to a target nucleic acid in the presence of a polymerase, where the sequencing reagent lacks at least one type of nucleotide monomer that can base-pair with at least one nucleotide in a target nucleic acid. In some embodiments, the sequencing reagent may contain at least one type of nucleotide monomer, but no more than three types of nucleotide monomer. In preferred embodiments, the sequencing reagent may contain at least one type of nucleotide monomer, but pair with no more than three types of nucleotides in a target nucleic acid having four different types of nucleotides.

In one example, a sequencing reagent can be delivered to a target nucleic acid in the presence of polymerase containing three different nucleotide monomers (A, C, G). In this example, a polynucleotide complementary to the target nucleic acid may be extended until the polymerase reaches an 'A'; here extension will be limited because of the lack of 'T' in the sequencing reagent. Such embodiments may be referred to as dark extension since one purpose of this process is to extend down a target nucleic acid without necessarily reading the sequence of the target nucleic acid.

In some embodiments, the dark cycle can be followed by a cycle in which a single nucleotide monomer is incorporated under conditions in which the type of nucleotide monomer can be identified. For example, a mixture of four terminator nucleotides can be added, wherein each nucleotide type has a different label. Alternatively, each of the four different terminator nucleotides can be added individually followed by detection to determine which is incorporated. Accordingly, the combined results of the dark extension step and subsequent single nucleotide extension step can be evaluated to identify two juxtaposed nucleotides. This can be illustrated by continuing with the example above in which dark extension is known to terminate at an A position in the template. If the results of the subsequent single nucleotide incorporation step indicate that a C was added, then it is apparent that the A in the template is next to a G. Repetition of the dark extension step followed by a single nucleotide incorporation step can be used to determine a low resolution sequence representation for the template constituting the sequence of AN dinucleotides in the template nucleic acid, wherein N represents any one of the four possible nucleotides and wherein the exact sequence of nucleotides between the AN dinucleotides in the template is unknown. Such repetition is possible if the terminating groups that are on the nucleotide monomers added in the single nucleotide extension step are reversible terminators. Further details for various embodiments are set forth in the Examples below.

In certain embodiments, the sequencing reagent can lack at least one, two, or three types of nucleotide monomer that may base-pair with at least one type of nucleotide in a target nucleic acid. In preferred embodiments, the sequencing reagent can lack at least one, two, or three different types of nucleotide monomer. It is also contemplated that in some embodiments, a sequencing reagent may contain a promiscuous nucleotide monomer such as a universal nucleotide monomer or semi-universal nucleotide monomer, that may base-pair with more than one type of nucleotide in a target nucleic acid. By "universal nucleotide monomer" is meant a nucleotide monomer that pairs with the entire complement of nucleotides present in the target nucleic acid. By "semi-universal nucleotide monomer" is meant, a nucleotide monomer that pairs with more than one but less than the entire complement of nucleotides present in the target nucleic acid. In such embodiments, the sequencing reagent can lack at least one type of nucleotide that may base-pair with at least one nucleotide in the target.

In some embodiments, limited extension of a polynucleotide can be repeated at least once. In such embodiments, a sequencing reagent delivered in a subsequent delivery step will be different from the sequencing reagent delivered in the prior delivery step. The difference in the sequencing reagents can include a lack of at least one different nucleotide monomer that may base-pair with a target nucleic acid. For example, a first sequencing reagent may contain A, C, G (Lack: T), a second sequencing reagent may contain A, C, T (Lack: G). In preferred embodiments, unincorporated nucleotide monomers can be removed before delivering a subsequent sequencing reagent. Further methods that may be used in limited dark extension steps and/or limited read extension steps, including doublet and triplet deliveries are described further herein.

In some embodiments, the nucleotide monomers present or absent from a sequencing reagent lacking at least one nucleotide monomer can be determined according to the sequence of a target nucleic acid. For example, the sequence of a target nucleic acid may be predicted, determined concurrently in real-time or previously known. Additionally, in performing a series of limited dark extension steps, it may be desirable to minimize the number of repeated limited dark extension steps in a homopolymer sequence (e.g. poly-A). In this example, a sequencing reagent containing at least one type of nucleotide monomer including 'T' could be utilized.

Nucleotide Monomer with Terminating Moiety

Additional methods that can be used for limited extension of a polynucleotide complementary to a target nucleic acid include delivering a sequencing reagent to a target nucleic acid in the presence of a polymerase, where the sequencing reagent includes at least one type of nucleotide monomer comprising a terminating moiety. In some embodiments, the nucleotide monomer may base-pair with at least one nucleotide that may be present in a target nucleic acid. In preferred embodiments, the terminating moiety is reversibly terminating.

In one example, a sequencing reagent containing A, C, G, $T^T$ (where the superscript "T" represents a nucleotide monomer comprising a terminating moiety) is delivered to a target nucleic acid in the presence of polymerase. In this example, a polynucleotide complementary to the target nucleic acid is extended until an 'A' is reached by the polymerase and $T^T$ is incorporated into the polynucleotide, limiting further extension.

In some embodiments, a sequencing reagent can contain at least one, two, three, or four different nucleotide monomers comprising a terminating moiety, where the nucleotide monomer may base-pair with at least one nucleotide that may be present in a target nucleic acid.

In some embodiments, limited extension of a polynucleotide using nucleotides with terminating moieties can be repeated at least once. In such embodiments, reversibly terminating moieties can be used to facilitate subsequent extensions. Furthermore, sequencing reagents in subsequent steps of limited extension can contain nucleotide monomers comprising terminating moieties that are the same or different.

In preferred embodiments, the reversibly terminating moiety of an incorporated nucleotide monomer can be removed prior to a subsequent limited extension step, such as a limited dark extension step, or a limited read extension step. In certain embodiments, unincorporated nucleotide monomers can be removed prior to delivering a subsequent sequencing reagent.

Oligonucleotide with Terminator Moiety

Additional methods that can be used for limited extension of a polynucleotide complementary to a target nucleic acid include delivering a sequencing reagent to a target nucleic acid in the presence of a ligase, where the sequencing reagent includes at least one oligonucleotide. In some embodiments, the oligonucleotide comprises a terminating moiety. In preferred embodiments, the terminating moiety is a reversibly terminating moiety. The oligonucleotide can be complementary to the target nucleic acid such that the oligonucleotide can be ligated to a polynucleotide complementary to at least a portion of the target nucleic acid, thus extending the polynucleotide complementary to the target nucleic acid. An oligonucleotide can comprise at least two linked nucleotide monomers. In some embodiments, the oligonucleotide can be at least a 2-mer, 3-mer, 4-mer, 5-mer, 6-mer, 7-mer, 8-mer, 9-mer, or 10-mer. In some embodiments, the length of the oligonucleotide may exceed 10 linked nucleotides. It will be appreciated that oligonucleotides of any length can be designed in order to facilitate accurate and/or rapid limited extensions. It will also be appreciated that the limited extensions can be dark extensions, however, as with the above examples of limited extension, there is no requirement that these limited extensions are dark extensions.

In certain embodiments, the sequencing reagent for limited extension can include a plurality of oligonucleotides. In some embodiments, the plurality of oligonucleotides can include different oligonucleotides. In particular embodiments, the plurality of oligonucleotides can include degenerate oligonucleotides or oligonucleotides comprising promiscuous bases. In preferred embodiments, the plurality of oligonucleotides includes at least one oligonucleotide that is complementary to the target nucleic acid such that the oligonucleotide can be ligated to a polynucleotide complementary to at least a portion of the target nucleic acid, thus extending the polynucleotide complementary to the target nucleic acid.

In one example, a sequencing reagent can be delivered to a target nucleic acid in the presence of ligase, where the sequencing reagent contains a plurality of oligonucleotides comprising reversibly terminating moieties. Some of the oligonucleotides may hybridize to various nucleotide sequences of the target nucleic acid, including a sequence where the hybridizing oligonucleotide can be ligated to a polynucleotide complementary to at least a portion of the target nucleic acid, thus extending the polynucleotide complementary to the target nucleic acid. However, the extension of the polynucleotide is limited because the reversibly terminating moiety of the ligated oligonucleotide can prevent further extension of the polynucleotide.

In certain embodiments, the reversibly terminating moiety can be removed prior to a subsequent delivery step, such as a subsequent limited dark extension step or limited read extension step. In certain embodiments, a limited extension step including oligonucleotides comprising terminating moieties can be repeated at least once. In certain embodiments, the sequencing reagent for limited extension can be removed prior to a subsequent delivery step.

Methods of Limited Read Extension

A variety of methods can be used for determining the identity of at least one nucleotide monomer incorporated into a polynucleotide complementary to a target nucleic acid. Such methods can include methods for limited extension of a polynucleotide complementary to a target nucleic acid as described herein. In a preferred embodiment, one or more nucleotide monomers comprising reversibly terminating moieties are provided to the target nucleic acid in the presence of a polymerase. When a nucleotide monomer having a terminating moiety is incorporated by the polymerase, polymerization of the polynucleotide complementary to the target nucleic acid is halted. Next, the terminated nucleotide monomer is detected. Some of the methods described herein can include direct and/or indirect detection of the incorporation of nucleotide monomers into a polynucleotide complementary to a target nucleic acid. In some embodiments, detecting incorporation of a nucleotide monomer into a polynucleotide also provides the identity of the nucleotide monomer that is incorporated since the user knows the identity of the sequencing reagent being provided. After the first read step, the reversibly terminating moiety can be removed and further rounds of reading or limited extension can be conducted. In some embodiments described herein, limited read steps can be conducted without using nucleotide monomers comprising a reversibly terminating moiety.

It will also be understood that methods for performing limited read extension can include reading one or more base pairs at high resolution or at low resolution. Some methods for reading sequences at low resolution are described in U.S. Provisional Patent Application No. 61/140,566 entitled "MULTIBASE DELIVERY FOR LONG READS 1N SEQUENCING BY SYNTHESIS PROTOCOLS" filed on Dec. 23, 2008, hereby incorporated by reference in its entirety. In an example embodiment, a doublet delivery method can be used. In such an embodiment, a sequencing reagent comprising two types of nucleotide monomer, for example, A and C, can be provided in a first delivery to a target nucleic acid in the presence of polymerase. In the subsequent delivery, a sequencing reagent comprising two types of nucleotide monomers different from the nucleotide monomers of the previous delivery, for example, G and T can be provided to the target nucleic acid. The deliveries can be repeated and sequence information of the target nucleic acid can be obtained.

In some doublet delivery methods, there can be three doublet delivery combinations that can be used, for example, A/C+G/T; A/G+C/T; and A/T+C/G ([First delivery nucleotide monomers]+[Second delivery nucleotide monomers]).

In some embodiments, a target nucleic acid may undergo at least two rounds of sequencing. For example, a first round may use one doublet delivery combination, and a second round may use a different doublet delivery combination. On combining the sequence data obtained from each round of sequencing, such embodiments can provide sequence information of a target nucleic acid at single-base resolution. Doublet delivery methods are also contemplated where a target nucleic acid can undergo three rounds of sequencing in which each doublet delivery combination is used. On combining the sequence data obtained from each round of sequencing, sequence information of the target nucleic acid can be obtained at single-base resolution with additional error checking.

In addition to doublet delivery methods, triplet delivery methods are also contemplated. Using such methods, a round of sequencing can be performed in which three different nucleotide monomers can be provided to a target nucleic acid in a delivery. In the next delivery, a nucleotide monomer which is different from the three nucleotide monomers of the previous delivery can be provided to the target nucleic acid. The combination of deliveries can be repeated for a round of sequencing and sequence information of the target nucleic acid can be obtained.

In another embodiment of triplet delivery methods, a round of sequencing can be performed in which three different nucleotide monomers can be provided to a target nucleic acid in a delivery. In the next delivery, a plurality of nucleotide monomers, wherein at least one of the nucleotide monomers is different from each of the nucleotide monomers of the prior delivery can be provided to the target nucleic acid. This combination of deliveries can be repeated for a round of sequencing and sequence information of the target nucleic acid can be obtained. As discussed herein, triplet delivery methods followed by delivery of a single nucleotide monomer that is different from each of the previously provided nucleotide monomers can produce sequence information relating to the position of a particular nucleotide monomer.

It will be appreciated that other combinations of nucleotide deliveries using nucleotide monomers can be used provided that the nucleotide monomers permit extension of a polynucleotide complementary to the target nucleic acid so as to obtain sequencing data. For example, the methods can employ a combination of several triplet deliveries, a combination of doublet and triplet deliveries, or a combination of singlet, doublet and triplet deliveries.

Identification of Sequencing Reagents

As will be understood, the extension of a polynucleotide complementary to a target nucleic acid using the methods described herein may be determined by the sequence of the target nucleic acid and the composition of the sequencing reagents. In some applications of the methods described herein, the sequence of at least a portion of a target nucleic acid may be known, predicted and/or determined in real-time. Accordingly, the composition of any sequencing reagent in any delivery may be determined to optimize the efficiency of obtaining sequence information. In one example, it may be desirable to minimize the number of repeated limited dark extension steps in a target nucleic acid containing a homopolymeric region (e.g. poly-A sequence). In this example, a sequencing reagent can contain 'T' nucleotide monomers so that extension is not limited within the poly-A sequence. In another example, the singlet, doublet and/or triplet delivery of nucleotide monomers in sequencing reagents can be modulated in a series of limited read extension step to maximize the resolution of the sequence representation obtained from a particular target nucleic acid.

Detection of Incorporated Nucleotide Monomers

Some of the methods described herein include detecting the incorporation of nucleotide monomers into a polynucleotide. Nucleotide monomers may be incorporated into at least a portion of a polynucleotide complementary to the target nucleic acid. In certain embodiments, at least a portion of the sequencing reagent, which comprises unincorporated nucleotide monomers, may be removed from the site of incorporation/detection prior to detecting incorporated nucleotide monomers.

A variety of methods can be used to detect the incorporation of nucleotide monomers into a polynucleotide. In some embodiments, incorporation of nucleotide monomers can be detected using nucleotide monomers comprising labels. Labels can include chromophores, enzymes, antigens, heavy metals, magnetic probes, dyes, phosphorescent groups, radioactive materials, chemiluminescent moieties, scattering or fluorescent nanoparticles, Raman signal generating moieties, and electrochemical detecting moieties. Such labels are known in the art some of which are exemplified previously herein or are disclosed, for example, in U.S. Pat. No. 7,052, 839; Prober, et. al., Science 238: 336-41 (1997); Connell et. al., BioTechniques 5(4)-342-84 (1987); Ansorge, et. al., Nucleic Acids Res. 15(11): 4593-602 (1987); and Smith et. al., Nature 321:674 (1986), the disclosures of which are hereby incorporated by reference in their entireties. In some embodiments, a label can be a fluorophore. Example embodiments include U.S. Pat. No. 7,033,764, U.S. Pat. No. 5,302, 509, U.S. Pat. No. 7,416,844, and Seo et al. "Four color DNA sequencing by synthesis on a chip using photocleavable fluorescent nucleotides," Proc. Natl. Acad. Sci. USA 102: 5926-5931 (2005), which are herein incorporated by reference in their entireties.

Labels can be attached to the $\alpha$, $\beta$, or $\gamma$ phosphate, base, or sugar moiety, of a nucleotide monomer (U.S. Pat. No. 7,361, 466; Zhu et al., "Directly Labeled DNA Probes Using Fluorescent Nucleotides with Different Length Linkers," Nucleic Acids Res. 22: 3418-3422 (1994), and Doublie et al., "Crystal Structure of a Bacteriophage T7 DNA Replication Complex at 2.2 Å Resolution," Nature 391:251-258 (1998), which are hereby incorporated by reference in their entireties). Attachment can be with or without a cleavable linker between the label and the nucleotide.

In some embodiments, a label can be detected while it is attached to an incorporated nucleotide monomer. In such embodiments, unincorporated labeled nucleotide monomers can be removed from the site of incorporation and/or the site of detection prior to detecting the label.

Alternatively, a label can be detected subsequent to release from an incorporated nucleotide monomer. Release can be through cleavage of a cleavable linker, or on incorporation of the nucleotide monomer into a polynucleotide where the label is linked to the $\beta$ or $\gamma$ phosphate of the nucleotide monomer, namely, where released pyrophosphate is labeled.

In some embodiments, at least a portion of unincorporated labeled nucleotide monomers can be removed from the site of incorporation and/or detection. In some embodiments, at least a portion of unincorporated labeled nucleotide monomers can be removed prior to detecting the incorporated labeled nucleotide. In some embodiments, at least about 5%, 10%, 20%, 25%, 30%, 40%, 50%, 60%, 70%, 80%, 90%, 95%, 96%, 97%, 98%, 99% or greater than 99% of unincorporated labeled nucleotide monomers can be removed prior to detecting the incorporated labeled nucleotide. In some embodiments, a label can be removed subsequent to a detection step and prior to a delivery. For example, a fluorescent label linked to an incorporated nucleotide monomer can be removed by cleaving the label from the nucleotide, or photobleaching the dye.

In some methods for detecting the incorporation of nucleotide monomers, pyrophosphate released on incorporation of a nucleotide monomer into a polynucleotide complementary to at least a portion of the target nucleic acid can be detected using pyrosequencing techniques. As described herein, pyrosequencing detects the release of pyrophosphate as particular nucleotides are incorporated into a nascent polynucleotide (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363, the disclosures of which are incorporated herein by reference in their entireties).

In some embodiments, at least a portion of the ATP and non-incorporated nucleotides can be removed from the site of incorporation and/or detection. In some embodiments, the ATP and non-incorporated nucleotides can be removed subsequent to a detection step and prior to a delivery. Removing the ATP and non-incorporated nucleotides can include, for example, a washing step and/or a degrading step using an enzyme such as apyrase (Ronaghi M, Karamohamed S, Pettersson B, Uhlen M, Nyren P. "Real-time DNA sequencing using detection of pyrophosphate release." Analytical Biochemistry. (1996) 242:84-89; Ronaghi M, Uhlen M, Nyren P. "A sequencing method based on real-time pyrophosphate." Science (1998) 281:363, the disclosures of which are hereby incorporated by reference in their entireties).

In some embodiments, at least a portion of released pyrophosphate can be removed from the site of incorporation and/or detection. In some embodiments, the released pyrophosphate can be removed subsequent to a detection step and prior to a delivery. In more embodiments, the released pyrophosphate can be removed prior to a delivery.

Example embodiments of methods for detecting released labeled pyrophosphate include using nanochannels, using flowcells to separate and detect labeled pyrophosphate from unincorporated nucleotide monomers, and using mass spectroscopy (U.S. Pat. No. 7,361,466; U.S. Pat. No. 6,869,764; and U.S. Pat. No. 7,052,839, which are hereby incorporated by reference in their entireties). Released pyrophosphate may also be detected directly, for example, using sensors such as nanotubes (U.S. Patent Application Publication No. 2006/0,199,193, which is hereby incorporated by reference in its entirety). In some embodiments, at least a portion of released pyrophosphate is removed from the site of incorporation and/or detection subsequent to the detection step and prior to a delivery. In more embodiments, at least about 5%, 10%, 20%, 25%, 30%, 40%, 50%, 60%, 70%, 80%, 90%, 95%, 96%, 97%, 98%, 99% or greater than 99% of released pyrophosphate is removed from the site of incorporation and/or detection subsequent to the detection step and prior to a delivery.

In some embodiments described herein, detection of a signal, such as light emitted from conversion of ATP and luciferin, or light emitted form a fluorescent label, is detected using a charge coupled device (CCD) camera. In other embodiments, a CMOS detector is used. Detection can occur on a CMOS array as described, for example, in Agah et al., "A High-Resolution Low-Power Oversampling ADC with Extended-Range for Bio-Sensor Arrays", IEEE Symposium 244-245 (2007) and Eltoukhy et al., "A 0.18 µm CMOS bioluminescence detection lab-on-chip", IEEE Journal of Solid-State Circuits 41: 651-662 (2006), the disclosures of which are incorporated herein by reference in their entireties. In addition, it will be appreciated that other signal detecting devices as known in the art can be used to detect signals produced as a result of nucleotide monomer incorporation into a polynucleotide complementary to a target nucleic acid.

Target Nucleic Acids

A target nucleic acid can include any nucleic acid of interest. Target nucleic acids can include, but are not limited to, DNA, RNA, peptide nucleic acid, morpholino nucleic acid, locked nucleic acid, glycol nucleic acid, threose nucleic acid, mixtures thereof, and hybrids thereof. In a preferred embodiment, genomic DNA fragments or amplified copies thereof are used as the target nucleic acid. In another preferred embodiment, mitochondrial or chloroplast DNA is used.

A target nucleic acid can comprise any nucleotide sequence. In some embodiment, the target nucleic acid comprises homopolymer sequences. A target nucleic acid can also include repeat sequences. Repeat sequences can be any of a variety of lengths including, for example, 2, 5, 10, 20, 30, 40, 50, 100, 250, 500, 1000 nucleotides or more. Repeat sequences can be repeated, either contiguously or non-contiguously, any of a variety of times including, for example, 2, 3, 4, 5, 6, 7, 8, 9, 10, 15, 20 times or more.

Some embodiments can utilize a single target nucleic acid. Other embodiments can utilize a plurality of target nucleic acids. In such embodiments, a plurality of target nucleic acids can include a plurality of the same target nucleic acids, a plurality of different target nucleic acids where some target nucleic acids are the same, or a plurality of target nucleic acids where all target nucleic acids are different. Embodiments that utilize a plurality of target nucleic acids can be carried out in multiplex formats such that reagents are delivered simultaneously to the target nucleic acids, for example, in a single chamber or on an array surface. In preferred embodiments, target nucleic acids can be amplified as described in more detail herein. In some embodiments, the plurality of target nucleic acids can include substantially all of a particular organism's genome. The plurality of target nucleic acids can include at least a portion of a particular organism's genome including, for example, at least about 1%, 5%, 10%, 25%, 50%, 75%, 80%, 85%, 90%, 95%, or 99% of the genome. In particular embodiments the portion can have an upper limit that is at most about 1%, 5%, 10%, 25%, 50%, 75%, 80%, 85%, 90%, 95%, or 99% of the genome Target nucleic acids can be obtained from any source. For example, target nucleic acids may be prepared from nucleic acid molecules obtained from a single organism or from populations of nucleic acid molecules obtained from natural sources that include one or more organisms. Sources of nucleic acid molecules include, but are not limited to, organelles, cells, tissues, organs, or organisms. Cells that may be used as sources of target nucleic acid molecules may be prokaryotic (bacterial cells, for example, *Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium,* and *Streptomyces* genera); archeaon, such as crenarchaeota, nanoarchaeota or euryarchaeotia; or eukaryotic such as fungi, (for example, yeasts), plants, protozoans and other parasites, and animals (including insects (for example, *Drosophila* spp.), nematodes (for example, *Caenorhabditis elegans*), and mammals (for example, rat, mouse, monkey, non-human primate and human)).

Target and Template Nucleic Acid Preparation

In several embodiments, target and template nucleic acids can be processed by standard molecular biology techniques for downstream applications. In some embodiments, target and template nucleic acids are identical. In other embodiments, a target nucleic acid is only a portion of a template nucleic acid. Accordingly, processes and compositions described herein that relate to target nucleic acids also apply to template nucleic acids and processes and composition described herein that relate to template nucleic acids also apply to target nucleic acids.

In particular embodiments, target nucleic acids can be prepared from fragmented polynucleotides. The fragments are subsequently attached to an adaptor polynucleotide sequence. In some embodiments, the adaptor polynucleotide sequence is double-stranded. In some embodiments, the fragments are end repaired prior to attaching to the adaptor polynucleotide sequences. Adaptor polynucleotides can be attached to one or both ends of the fragmented nucleotide sequences. It will be appreciated that the same or different adaptor can be bound to each end of the fragment, thereby producing an "adaptor-fragment-adaptor" construct. It will also be appreciated that a plurality of the same or different adaptor can be bound to each end of the fragment. In preferred embodiments, different adaptors are attached to each end of the fragment when adaptors are attached to both ends of the fragment. Methods of attaching nucleic acid adaptors to a nucleic acid of interest are well known in the art. Particularly, ligation methods are known in the art using standard molecular cloning techniques (Sambrook and Russell, Molecular Cloning, A Laboratory Manual, 3$^{rd}$ edition Cold Spring Harbor Laboratory Press (2001), herein incorporated by reference).

In some embodiments, the adaptor constructs may contain a mismatched region on one or both of the strands that does not hybridize with a sequence on the other strand of the adaptor. In some such embodiments, these regions can act as amplification priming sites. Additionally, adaptor-fragment-adaptor constructs can be amplified by standard amplification reactions generally involving forward and reverse oligonucleotide primers that can anneal to at least a portion of the adaptors. Forward and reverse amplification primers may also extend beyond the adaptors. It will be appreciated by one of ordinary skill in the art that forward and reverse primer sequences do not need to be perfectly complementary to their primer-binding sequence of the template. Primers can be designed having a suitable number of mismatched bases against the template and still exhibit an appropriate level of specific annealing to the template. In various embodiments, a target nucleic acid having one or two duplex adaptors attached to its end(s) is amplified prior to hybridization to a substrate.

In some embodiments, an oligonucleotide complementary to a sequencing primer can be incorporated with adaptors attached to a target nucleic acid. For analysis of multiple samples, different oligonucleotide tags complementary to separate sequencing primers can be incorporated with adaptors attached to a target nucleic acid.

In some embodiments, an oligonucleotide index tag can be incorporated with adaptors attached to a target nucleic acid. In various embodiments, copies of the same fragment of a nucleic acid of interest will have the same oligonucleotide index tag such that the index tag identifies sequencing reads derived from the same fragment of the nucleic acid of interest. Different fragments (and copies thereof) of the nucleic acid of interest will have different oligonucleotide index tags such that copies of different fragments can be identified by the sequence of the different index tags. Oligonucleotide index tags may range in length from about 5, 10, 15, 20, 25, 30, 35, 40, 45, 50, 75, to 100 nucleotides or basepairs, or any length in between. In some embodiments, the index tags can be greater than 100 nucleotides or basepairs in length. Furthermore, it will be appreciated that oligonucleotide index tags can be supplied independently from adaptors.

Converting Double-Stranded Nucleic Acids to Single-Stranded Nucleic Acids

Some embodiments of the present invention relate to converting double-stranded nucleic acids to single-stranded nucleic acids. In a variety of embodiments, methods of obtaining a contiguous nucleotide sequence of a nucleic acid of interest are provided. Single-stranded nucleic acids can be generated corresponding to the nucleic acid of interest. As used herein, "nucleic acid" includes both DNA and RNA. In some embodiments, the term "nucleic acid" includes DNA and RNA comprising one or more modified nucleobases or nucleobase analogs. Modified nucleic acids are nucleic acids having nucleotides or structures which may or may not occur in nature. For example, methylation of DNA bases are modifications that often occur in nature, whereas aminations of nucleobases typically do not. Double-stranded nucleic acids can include double-stranded DNA, double-stranded RNA and double-stranded DNA/RNA hybrid molecules. Double-stranded nucleic acids can be denatured or converted to single-stranded nucleic acids by a variety of methods. These methods can include chemical methods, for example, by the addition of chaotropic agents, such as urea, to induce double-stranded nucleic acids to separate into single-stranded molecules. Other methods include physical means, such as heating to a temperature sufficient to disrupt the hydrogen bonding between the two strands of the double-stranded nucleic acids. Still other methods include employing one or more enzymes, such as nucleases, to preferentially digest one of the strands of the double-stranded nucleic acid, thereby leaving an undigested single strand. Furthermore, double-stranded nucleic acid can be converted to a single-stranded nucleic acid by treatment with an enzyme or other reagent that degrades one strand. Enzymatic or chemical treatment can occur under conditions that are not sufficient to disrupt the hydrogen bonding between the two strands of the double-stranded nucleic acids when not in the presence of the degrading reagent or enzyme. For example, the temperature can be sufficiently low that the double-stranded nucleic acid remains hybridized absent the degrading reagent or enzyme. Also, the chemical conditions can be such that the hybrid is not substantially disrupted absent the degrading reagent or enzyme.

The methods exemplified herein for converting double-stranded nucleic acids to single-stranded nucleic acids are also applicable to converting a double-stranded nucleic acid region to a region that is single-stranded. Thus, the methods can be used to produce a nucleic acid having a single-stranded region that is of sufficient length to hybridize to a capture probe or other nucleic acid. In other words, a double-stranded nucleic acid region can be retained in a nucleic acid that is converted to have a single-stranded region in a method of the invention. For example, a nuclease can digest a portion of one strand in a double-stranded nucleic acid such that the product has both a double-stranded region and a single-stranded region. Such molecules can be referred to as partial duplexes.

There are a variety of nucleases that can be used to digest one strand of a double-stranded nucleic acid, so as to form a single-stranded nucleic acid. Examples of such nucleases include, but are not limited to, lambda exonuclease, exonuclease III, and T7 exonuclease.

In preferred embodiments, a double-stranded nucleic acid can be converted to a single-stranded nucleic acid using lambda exonuclease. Lambda exonuclease is a highly processive exodeoxyribonuclease that selectively digests the 5'-phosphorylated strand of double-stranded DNA in a 5' to 3' direction. The enzyme exhibits greatly reduced activity on single-stranded DNA and non-phosphorylated DNA, and has no activity at nicks and limited activity at gaps in DNA (Little, J. W., An exonuclease induced by bacteriophage lambda: II, Nature of the enzymatic reaction, J. Biol. Chem., 242, 679-686, 1967; Mitsis, P. G., Kwagh, J. G., Characterization of the interaction of lambda exonuclease with the ends of DNA, Nucleic Acids Res., 27, 3057-3063, 1999).

Additional nucleases for converting a double-stranded nucleic acid to a single-stranded nucleic acid include exonuclease III. Exonuclease III catalyzes the stepwise removal of mononucleotides from 3'-hydroxyl termini of duplex DNA (Rogers, G. S. and Weiss, B. (1980) L. Grossman and K. Moldave (Eds.), *Methods Enzymol.,* 65, pp. 201-211. New York: Academic Press). During each binding event, only a limited number of nucleotides are removed, resulting in coordinated progressive deletions within the population of DNA molecules (Sambrook, J., Fritsch, E. F. and Maniatis, T. (1989) *Molecular Cloning: A Laboratoty Manual (2nd Ed.),* 5.84-5.85). Although the enzyme also acts at nicks in duplex DNA to produce single-strand gaps, the preferred substrates are blunt or recessed 3'-termini. The enzyme is not active on single-stranded DNA, and thus 3'-protruding termini are resistant to cleavage. The degree of resistance depends on the length of the extension, with extensions 4 bases or longer being essentially resistant to cleavage. Temperature, salt concentration and the ratio of enzyme to DNA can affect enzyme activity, thus reaction conditions can be tailored to specific applications. Exonuclease III may also have RNase H, 3'-phosphatase and AP-endonuclease activities (Rogers, G. S.

and Weiss, B. (1980) L. Grossman and K. Moldave (Eds.), *Methods Enzymol.*, 65, pp. 201-211. New York: Academic Press).

Still other nucleases for converting a double-stranded nucleic acid to a single-stranded nucleic acid include T7 exonuclease. T7 Exonuclease acts in the 5' to 3' direction, catalyzing the removal of 5' mononucleotides from duplex DNA. T7 Exonuclease initiates nucleotide removal from the 5' termini or at gaps and nicks of double-stranded DNA (Kerr, C. and Sadowski, P. D. (1972) *J. Biol. Chem.*, 247, 305-318). It will degrade both 5' phosphorylated or 5' dephosphorylated DNA. The enzyme may also degrade RNA and DNA from RNA/DNA hybrids in the 5' to 3' direction (Shinozaki, K. and Okazaki, T. (1978) *Nucl. Acids Res.*, 5, 4245-4261).

Nucleases that specifically recognize RNA/DNA hybrids can also be used to promote strand conversion. For example, RNase H is a nuclease that specifically recognizes RNA/DNA hybrids and specifically degrades the RNA. Because RNase H does not degrade DNA it can be used to convert double-stranded DNA/RNA hybrids to single-stranded DNA molecules. RNase H is often used to destroy the RNA template after first-strand cDNA synthesis and in nuclease protection assays. RNase H can also be used to degrade specific RNA strands when a DNA oligonucleotide is hybridized, such as in the removal of the poly(A) tail from mRNA hybridized to oligo(dT) or the destruction of specific RNA molecules inside or outside the living cell.

Hybridization

Some embodiments of the present invention relate to hybridization between single-stranded nucleic acids and capture probes. In some embodiments, the capture probes are primers that are attached to the surface of an array substrate. In some embodiments, the capture probes are attached to the surface of the array substrate and can serve as primers in addition to functioning as a capture probe. As described further herein, capture probes can be short nucleic acids or oligonucleotides. Short nucleic acids typically have a length of 1000 nucleotide or less. In a preferred embodiment, the length of a capture probe ranges from about 10 nucleotides to about 100 nucleotides. In a more preferred embodiment, the length of a capture probe can be less than 50 nucleotides. In an even more preferred embodiment, the length of a capture probe range from about 20 to 40 nucleotides. Other embodiments of the present invention relate to hybridization between single-stranded nucleic acids and other nucleic acid molecules having a length greater than 1000 base pairs. Several useful properties of single-stranded nucleic acids are exemplified below. It will be understood that a single-stranded region of a nucleic acid can have similar useful properties even if the nucleic acid also has a double-stranded region. As such, it will be appreciated that in some embodiments, hybridization can occur between partial two or more partial duplex molecules.

Hybridization occurs when hydrogen bonds form between complementary nucleotide bases, for example, T-A, C-G, and A-U. Complementary nucleic acids comprise complementary bases with the capacity for precise pairing between two nucleotides, for example, if a nucleotide at a certain position in the sequence of nucleotides of an single-stranded nucleic acid is capable of hydrogen bonding with a nucleotide at the same position in the sequence of nucleotides of a capture probe, then the single-stranded nucleic acid and capture probe are considered to be complementary to each other at that position. The single-stranded nucleic acid and the capture probe are complementary to each other when a sufficient number of corresponding positions in each molecule are occupied by nucleotides which can hydrogen bond with each other. Accordingly, complementary does not necessarily mean that two hybridizing nucleic acid stranded have 100% nucleotide complementarity in the hybridizing region. For example, in some embodiments, hybridizing nucleic acids can have less than 100% complementarity, less than 99% complementarity, less than 98% complementarity, less than 97% complementarity, less than 96% complementarity, less than 95% complementarity, less than 94% complementarity, less than 93% complementarity, less than 92% complementarity, less than 91% complementarity, less than 90% complementarity, less than 89% complementarity, less than 88% complementarity, less than 87% complementarity, less than 86% complementarity, less than 85% complementarity, less than 84% complementarity, less than 83% complementarity, less than 82% complementarity, less than 81% complementarity, less than 80% complementarity, 79% complementarity, less than 78% complementarity, less than 77% complementarity, less than 76% complementarity, less than 75% complementarity, less than 74% complementarity, less than 73% complementarity, less than 72% complementarity, less than 71% complementarity or less than 70% complementarity in the hybridizing region provided that the complementarity is sufficient to promote hybridization under the conditions used. In preferred embodiments, the hybridization occurs between specific complementary sequences and not between non-complementary sequences.

The ability of a single-stranded nucleic acid and a capture probe to hybridize to one another can be affected by the number of complementary nucleotides and the relative positions of those complementary nucleotides in the single-stranded nucleic acid and capture probe. For example, a single-stranded nucleic acid containing a greater number of complementary nucleotides in a contiguous sequence can have a higher degree of complementarity than a single-stranded nucleic acid contains a lower number of complementary nucleotides with non-complementary nucleotides dispersed therein. In addition, as indicated above, the ability of a single-stranded nucleic acid and capture probe to hybridize to one another can be modulated by varying the conditions in which the hybridization occurs.

In some embodiments of the methods and compositions described herein, a single-stranded nucleic acid can contain at least one sequence that can hybridize to a sequence contained in a capture probe. Such sequences that can hybridize include complementary nucleotides. In certain embodiments, a sequence that can hybridize can contain a contiguous sequence of complementary nucleotides. For example, a single-stranded nucleic acid can contain at least one contiguous sequence complementary to at least one sequence in capture probe. In such embodiments, the at least one contiguous sequence of complementary nucleotides contained in the capture probe and/or single-stranded nucleic acid can have a length of at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides, at least 22 nucleotides, at least 23 nucleotides, at least 24 nucleotides, at least 25 nucleotides, at least 26 nucleotides, at least 27 nucleotides, at least 28 nucleotides, at least 29 nucleotides, at least 30 nucleotides, at least 31 nucleotides, at least 32 nucleotides, at least 33 nucleotide, at least 34 nucleotides, at least 35 nucleotides, at least 36 nucleotides, at least 37 nucleotides, at least 38 nucleotides, at least 39 nucleotides, at least 40 nucleotides, at least 41 nucleotides, at least 42 nucleotides, at least 43 nucleotides, at least 44 nucleotides, at least 45 nucleotides, at least 46 nucleotides, at least 47 nucleotides, at least 48 nucleotides, at least 49 nucleotides, at least 50 nucleotides, at least 51 nucleotides, at least 52 nucleotides, at least 53 nucleotides, at least 54 nucleotides, at least 55 nucleotides, at least 56 nucleotides, at least 57 nucleotides, at least 58 nucleotides, at least 59 nucleotides, at least 60 nucleotides, at least 61 nucleotides, at least 62 nucleotides. at least 63 nucleotides, at least 64 nucleotides, at least 65 nucleotides, at least 66 nucleotides, at least 67 nucleotides, at least 68 nucleotides, at least 69 nucleotides, at least 70 nucleotides, at least 71 nucleotides, at least 72 nucleotides, at least 73 nucleotides, at least 74 nucleotides or at least 75 nucleotides.

In other embodiments, the sequence that can hybridize to another sequence can contain non-complementary nucleotides. In such embodiments, a sequence that can hybridize can contain 1 non-complementary nucleotide, 2 non-complementary nucleotides, 3 non-complementary nucleotides, 4 non-complementary nucleotides, 5 non-complementary nucleotides, 6 non-complementary nucleotides, 7 non-complementary nucleotides, 8 non-complementary nucleotides, 9 non-complementary nucleotides, 10 non-complementary nucleotides, 11 non-complementary nucleotides, 12 non-complementary nucleotides, 13 non-complementary nucleotides, 14 non-complementary nucleotides, 15 non-complementary nucleotides, 16 non-complementary nucleotides, 17 non-complementary nucleotides, 18 non-complementary nucleotides, 19 non-complementary nucleotides, 20 non-complementary nucleotides, 25 non-complementary nucleotides, 30 non-complementary nucleotides, 35 non-complementary nucleotides, 40 non-complementary nucleotides, 45 non-complementary nucleotides, or 50 non-complementary nucleotides.

As is known in the art, the ability of a single-stranded nucleic acid and capture probe to hybridize to one another can be modulated by varying the conditions in which the hybridization occurs. Such conditions are well known in the art and can include, for example, pH, temperature, concentration of salts, and the presence of particular molecules in the hybridization reaction. Under conditions of low stringency, a capture probe and single-stranded nucleic acid with a low degree of complementarity may be able to hybridize to one another. Conversely, under more highly stringent conditions, only capture probes and single-stranded nucleic acids with a high degree of complementarity are likely to hybridize to one another.

In certain embodiments, hybridization of the single-stranded nucleic acid and capture probe can be made to occur under conditions with high stringency. One condition that greatly affects stringency is temperature. In general, increasing the temperature at which the hybridization is performed increases the stringency. As such, the hybridization reactions described herein can be performed at a different temperature depending on the desired stringency of hybridization. For example, hybridization can be performed at a temperature ranging from 15° C. to 95° C. In some embodiments, the hybridization is performed at a temperature of about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., or about 95° C. In other embodiments, the stringency of the hybridization can further altered by the addition or removal of components of the buffered solution.

In particular embodiments, a probe, such as a capture probe, can be resistant to exonuclease degradation. For example the probe can have a non natural backbone that can not be cleaved by a particular exonuclease such as a protein nucleic acid backbone. A probe can include a blocking group that prevents or inhibits exonuclease degradation. For example, a blocking group can present at the 3' end of a probe or at the 5' end of the probe. A blocking group at the 3' end can prevent degradation of the probe by exonuclease III. A blocking group at the 5' end can prevent degradation of the probe by lambda exonuclease or T7 exonuclease.

Preparation of Amplified Polynucleotides

In some embodiments of the methods described herein, an amplification step is performed. In some embodiments, target nucleic acids may be amplified prior to providing them to the array. In other embodiments, polynucleotides, such as template nucleic acids, attached to the array, for example by hybridization with a capture probe, can be amplified prior to processing the polynucleotides to produce a set of overlapping regions to be sequenced. Additionally or alternatively, amplification may occur subsequent to processing the polynucleotides to produce a set of overlapping regions to be sequenced.

In a particular embodiment, clustered arrays of nucleic acid colonies can be prepared as described in U.S. Pat. No. 7,115,400; US Published Patent Application No. 2005/0100900 A1; PCT Publication No. WO 00/18957 or PCT Publication No. WO 98/44151, the contents of which are herein incorporated by reference in their entireties. Such methods are known as bridge amplification or solid-phase amplification and are particularly useful for sequencing applications. In some embodiments, a target nucleic acid can be amplified for use with the methods described herein. Such embodiments include preparing amplified libraries of target nucleic acids. Library preparation can be accomplished by random fragmentation of DNA, followed by in vitro ligation of common adaptor sequences.

Various protocols can be used to generate an array of millions of spatially immobilized PCR colonies, sometimes referred to as polonies, on a substrate. For example, such clonally clustered amplicons of target nucleic acids can be generated by in situ polonies, emulsion PCR, or bridge PCR (Mitra, R. D. & Church, G. M. "In situ localized amplification and contact replication of many individual DNA molecules." *Nucleic Acids Res.* 27, e34 (1999); Dressman, D., Yan, H., Traverso, G., Kinzler, K. W. & Vogelstein, B. "Transforming single DNA molecules into fluorescent magnetic particles for detection and enumeration of genetic variations." *Proc. Natl. Acad Sci. USA* 100, 8817-8822 (2003); Adessi, C. et al. "Solid phase DNA amplification: characterization of primer attachment and amplification mechanisms." *Nucleic Acids Res.* 28, e87 (2000); Fedurco, M., Romieu, A., Williams, S., Lawrence, I. & Turcatti, G. "BTA, a novel reagent for DNA attachment on glass and efficient generation of solid-phase amplified DNA colonies." *Nucleic Acids Res.* 34, e22 (2006), each of which is incorporated by reference herein in their entireties).

In embodiments using emulsion PCR, an in vitro-constructed adaptor flanked shotgun library can be PCR amplified in a water-in-oil emulsion. The PCR is multi-template PCR, because only a single primer pair is used. One of the PCR primers is tethered to the surface (5'-attached) of micron-scale beads that are also included in the reaction. A low template concentration results in most bead-containing compartments having either zero or one template molecule present. In productive emulsion compartments (where both a bead and template molecule is present), PCR amplicons can be captured to the surface of the bead. After breaking the emulsion, beads bearing amplification products can be selectively enriched. Each clonally amplified bead will bear on its surface PCR products corresponding to amplification of a single molecule from the template library. Various embodiments of emulsion PCR methods that are useful are set forth in U.S. Patent Application Publication No. 2005/0042648; U.S. Patent Application Publication No. 2005/0079510; U.S. Patent Application Publication No. 2005/0130173 and WO 05/010145, each of which is incorporated herein by reference.

In some embodiments, clustered amplicons that can serve as sequencing features are generated by emulsion PCR on a surface of a substrate. In some embodiments, clustered amplicons are attached to the surface of a bead, preferably micron-scale or sub-micron-scale beads adapted to be immobilized to a planar substrate for sequencing. In other embodiments, amplicon-bearing beads can be placed into wells of an array. For example, microfabricated arrays can be designed to have picoliter-sized wells that accommodate a single bead per well. Features attached to beads can be sequenced by any method, including but not limited to sequencing-by-synthesis (driven by DNA polymerase or DNA ligase), pyrosequencing, and sequencing by hybridization. In some embodiments, amplification methods other than emulsion PCR can be used to produce amplicons.

In embodiments using bridge PCR, also known as cluster PCR, an in vitro-constructed adaptor-flanked shotgun library can be PCR amplified using primers coated densely on the surface of a substrate. The primers are attached at their 5' ends by a flexible linker. Amplification products originating from any given member of the template library remain locally tethered near the point of origin. At the conclusion of the PCR, each clonal cluster contains ~1,000 copies of a single member of the template library. Accurate measurement of the concentration of the template library can be used to optimize the cluster density while simultaneously avoiding overcrowding. Various embodiments of bridge PCR methods that are useful are set forth in U.S. Patent Application Publication No. 2007/0128624, WO 07/010,251, U.S. Pat. No. 6,090,592 and U.S. Pat. No. 5,641,658, each of which is incorporated herein by reference. Generally, in bridge amplification (e.g. bridge PCR), also known as cluster amplification, both forward and reverse primers are attached to a substrate typically at their 5' ends by a flexible linker. Amplicons originating from a template library or template of interest remain attached to the substrate and clustered at a site on the substrate. Thus, bridge PCR amplifies clonal sequencing features. A plurality of clusters can be amplified to sites on a flow-cell. Amplicons are linearized to single strands and a sequencing primer is hybridized to a universal sequence flanking the nucleotide region of interest. Sequencing can be performed by any methodology described herein, preferably by sequencing-by-synthesis (SBS) involving reversible terminator nucleotides having a cleavable moiety at the 3' end and a cleavable fluorescent label.

Such embodiments, can generate PCR amplicons derived from library molecules at sites or features on a planar substrate (in situ polonies, bridge PCR), or to the surface of micron-scale heads, which can be recovered and arrayed (emulsion PCR).

Polymerases and Ligases

The methods described herein can utilize polymerases. Polymerases can include, but are not limited to, DNA polymerases, RNA polymerases, reverse transcriptases, and mixtures thereof. Ligases can include, but are not limited to, DNA ligases, RNA ligases, and mixtures thereof. The polymerase can be a thermostable polymerase or a thermodegradable polymerase. Examples of thermostable polymerases include polymerases isolated from *Thermus aquaticus*, *Thermus thermophilus*, *Pyrococcus woesei*, *Pyrococcus furiosus*, *Thermococcus litoralis*, *Bacillus stearothermophilus*, and *Thermotoga maritima*. Examples of thermodegradable polymerases include *E. coli* DNA polymerase, the Klenow fragment of *E. coli* DNA polymerase, T4 DNA polymerase, and T7 DNA polymerase. More examples of polymerases that can be used with the methods described herein include *E. coli*, T7, T3, and SP6 RNA polymerases, and AMV, M-MLV, and HIV reverse transcriptases. Examples of ligases include *E. coli* DNA ligase, T4 DNA ligase, Taq DNA ligase, 9° N DNA ligase, Pfu DNA ligase, T4 RNA ligase 1, and T4 RNA ligase 2. In some embodiments, the polymerase can have proofreading activity or other enzymic activities. Polymerases can also be engineered for example, to enhance or modify reactivity with various nucleotide analogs or to reduce an activity such as proofreading or exonuclease activity. Exemplary engineered polymerases that can be used are described in US 2006/0240439 A1 and US 2006/0281109 A1.

Removing Nucleotide Monomers and/or Pyrophosphate

Some of the methods described herein include a step of removing a substance from a site. A site can include a site of nucleotide monomer incorporation and/or a site of detection of monomer incorporation. A substance can include, for example, any constituent of a sequencing reagent, any product of incorporating one or more nucleotide monomers into a polynucleotide complementary to a target nucleic acid, such as pyrophosphate, a target nucleic acid, a polymerase, a cleaved label, a polynucleotide complementary to a target nucleic acid, an oligonucleotide. In a preferred embodiment, one or more nucleotide monomers are removed from a site. In another preferred embodiment, pyrophosphate is removed from a site. In even more preferred embodiments, both nucleotide monomers and pyrophosphate are removed from a site. Removing a substance can include a variety of methods, for example, washing a substance from a site, diluting a substance from a site, sequestering a substance from a site, degrading a substance, inactivating a substance and denaturing a substance.

In certain embodiments of the methods described herein, any portion of a substance can be removed from a site. In particular embodiments, at least about 1%, 2%, 3%, 4%, 5%, 10%, 20%, 25%, 30%, 40%, 50%, 60%, 70%, 80%, 90%, 95%, 96%, 97%, 98%, 99% or greater than 99% of a substance can be removed from a site. In preferred embodiments, approximately 100% of a substance can be removed from a site.

In particular embodiments of the methods described herein, a portion of a sequencing reagent can be removed from a site of nucleotide monomer incorporation and/or a site of detection of monomer incorporation. A sequencing reagent can be removed from a site subsequent to providing the sequencing reagent to a target nucleic acid in the presence of polymerase. In preferred embodiments, a sequencing reagent can be removed from a site before providing a subsequent sequencing reagent to a target nucleic acid in the presence of polymerase. In any of the above-described embodiments, the sequencing reagent can be the first, second, third, fourth, fifth or any subsequent sequencing reagent that is provided.

In some embodiments, an unincorporated nucleotide monomer can be removed from a site. In certain embodiments, an unincorporated nucleotide monomer can be removed from a site of nucleotide monomer incorporation and/or detection after providing the nucleotide monomer to a target nucleic acid. In more embodiments, an unincorporated nucleotide monomer can be removed from a site before providing a subsequent sequencing reagent to a target nucleic acid.

In some embodiments of the methods described herein, pyrophosphate can be removed from a site. In certain embodiments, pyrophosphate can be removed from a site of nucleotide monomer incorporation and/or detection after detecting incorporation one or more nucleotide monomers into a polynucleotide. In other embodiments, pyrophosphate can be removed from a site of nucleotide monomer incorporation and/or detection before providing a subsequent sequencing reagent to a target nucleic acid.

In some embodiments, a polynucleotide complementary to a target nucleic acid can be removed from a site. In certain embodiments, a polynucleotide complementary to a target nucleic acid can be removed from the target nucleic acid subsequent to performing a first run of sequencing on the target nucleic acid. In particular embodiments, a polynucleotide complementary to a target nucleic acid can be removed from the target nucleic acid before performing a second, third, or any subsequent run of sequencing on the target nucleic acid.

It will be understood that, in some embodiments, a substance can be removed from a site at any time before, during or subsequent to a round of sequencing.

Sequencing Methods

The methods described herein can be used in conjunction with a variety of sequencing techniques. In some embodiments, the process to determine the nucleotide sequence of a target nucleic acid can be an automated process.

Some embodiments include Sequencing by synthesis (SBS) techniques. SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in some of the methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides. In methods using nucleotide monomers lacking terminators, the number of different nucleotides added in each cycle can be dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.). In preferred methods a terminator moiety can be reversibly terminating.

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.). However, it is also possible to use the same label for the two or more different nucleotides present in a sequencing reagent or to use detection optics that do not necessarily distinguish the different labels. Thus, in a doublet sequencing reagent having a mixture of A/C both the A and C can be labeled with the same fluorophore. Furthermore, when doublet delivery methods are used all of the different nucleotide monomers can have the same label or different labels can be used, for example, to distinguish one mixture of different nucleotide monomers from a second mixture of nucleotide monomers. For example, using the [First delivery nucleotide monomers]+[Second delivery nucleotide monomers] nomenclature set forth above and taking an example of A/C+G/T, the A and C monomers can have the same first label and the G and T monomers can have the same second label, wherein the first label is different from the second label. Alternatively, the first label can be the same as the second label and incorporation events of the first delivery can be distinguished from incorporation events of the second delivery based on the temporal separation of cycles in an SBS protocol. Accordingly, a low resolution sequence representation obtained from such mixtures will be degenerate for two pairs of nucleotides (T/G, which is complementary to A and C, respectively; and C/A which is complementary to G/T, respectively).

Some embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." *Analytical Biochemistry* 242(1), 84-9; Ronaghi, M. (2001) "Pyrosequencing sheds light on DNA sequencing." *Genome Res.* 11(1), 3-11; Ronaghi, M., Uhlen, M. and Nyren, P. (1998) "A sequencing method based on real-time pyrophosphate." *Science* 281(5375), 363; U.S. Pat. No. 6,210,891; U.S. Pat. No. 6,258,568 and U.S. Pat. No. 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons.

In another example type of SBS, cycle sequencing is accomplished by stepwise addition of reversible terminator nucleotides containing, for example, a cleavable or photobleachable dye label as described, for example, in U.S. Pat. No. 7,427,67, U.S. Pat. No. 7,414,1163 and U.S. Pat. No. 7,057,026, the disclosures of which are incorporated herein by reference. This approach is being commercialized by Solexa (now Illumina Inc.), and is also described in WO 91/06678 and WO 07/123,744 (filed in the United States patent and trademark Office as U.S. Ser. No. 12/295,337), each of which is incorporated herein by reference in their entireties. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

In accordance with the methods set forth herein, the two or more different nucleotide monomers that are present in a sequencing reagent or delivered to a template nucleic acid in the same cycle of a sequencing run need not have a terminator moiety. Rather, as is the case with pyrosequencing, several of the nucleotide monomers can be added to a primer in a template directed fashion without the need for an intermediate deblocking step. The nucleotide monomers can contain labels for detection, such as fluorescent labels, and can be used in methods and instruments similar to those commercialized by Solexa (now Illumina Inc.). Preferably in such embodiments, the labels do not substantially inhibit extension under SBS reaction conditions. However, the detection labels can be removable, for example, by cleavage or degradation. Removal of the labels after they have been detected in a particular cycle and prior to a subsequent cycle can provide the advantage of reducing background signal and crosstalk between cycles. Examples of useful labels and removal methods are set forth herein.

In particular embodiments some or all of the nucleotide monomers can include reversible terminators. In such embodiments, reversible terminators/cleavable fluors can include fluor linked to the ribose moiety via a 3' ester linkage (Metzker, *Genome Res.* 15:1767-1776 (2005), which is incorporated herein by reference). Other approaches have separated the terminator chemistry from the cleavage of the fluorescence label (Ruparel et al., *Proc Natl Acad Sci USA* 102: 5932-7 (2005), which is incorporated herein by reference in its entirety). Ruparel et al described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination. Examples of modified nucleotides are also described in U.S. Pat. No. 7,427,673, and U.S. Pat. No. 7,057,026, the disclosures of which are incorporated herein by reference in their entireties.

Additional example SBS systems and methods which can be utilized with the methods and systems described herein are described in U.S. Patent Application Publication No. 2007/0166705, U.S. Patent Application Publication No. 2006/0188901, U.S. Pat. No. 7,057,026, U.S. Patent Application Publication No. 2006/0240439, U.S. Patent Application Publication No. 2006/0281109, PCT Publication No. WO 05/065814, U.S. Patent Application Publication No. 2005/0100900, PCT Publication No. WO 06/064199 and PCT Publication No. WO 07/010,251, the disclosures of which are incorporated herein by reference in their entireties.

Some embodiments can utilize sequencing by ligation techniques. Such techniques utilize DNA ligase to incorporate nucleotides and identify the incorporation of such nucleotides. Example SBS systems and methods which can be utilized with the methods and systems described herein are described in U.S. Pat. No. 6,969,488, U.S. Pat. No. 6,172,218, and U.S. Pat. No. 6,306,597, the disclosures of which are incorporated herein by reference in their entireties.

Some embodiments can include techniques that may not be associated with traditional SBS methodologies. One example can include nanopore sequencing techniques (Deamer, D. W. & Akeson, M. "Nanopores and nucleic acids: prospects for ultrarapid sequencing." *Trends Biotechnol.* 18, 147-151 (2000); Deamer, D. and D. Branton, "Characterization of nucleic acids by nanopore analysis". *Acc. Chem. Res.* 35:817-825 (2002); Li, J., M. Gershow, D. Stein, E. Brandin, and J. A. Golovchenko, "DNA molecules and configurations in a solid-state nanopore microscope" *Nat. Mater.* 2:611-615 (2003), the disclosures of which are incorporated herein by reference in their entireties). In such embodiments, the target nucleic acid passes through a nanopore. The nanopore can be a synthetic pore or biological membrane protein, such as α-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." *Clin. Chem.* 53, 1996-2001 (2007); Healy, K. "Nanopore-based single-molecule DNA analysis." *Nanomed.* 2, 459-481 (2007); Cockroft, S. L., Chu, J., Amorin, M. & Ghadiri, M R. "A single-molecule nanopore device detects DNA polymerase activity with single-nucleotide resolution." *J. Am. Chem. Soc.* 130, 818-820 (2008), the disclosures of which are incorporated herein by reference in their entireties). In some such embodiments, nanopore sequencing techniques can be useful to confirm sequence information generated by the methods described herein.

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. No. 7,329,492 and U.S. Pat. No. 7,211,414 (each of which is incorporated herein by reference in their entireties) or nucleotide incorporations can be detected with zero-mode waveguides as described, for example, in U.S. Pat. No. 7,315,019 (which is incorporated herein by reference in its entirety) and using fluorescent nucleotide analogs and engineered polymerases as described, for example, in U.S. Pat. No. 7,405,281 and U.S. Patent Application Publication No. 2008/0108082 (each of which is incorporated herein by reference in their entireties). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." *Science* 299, 682-686 (2003); Lundquist, P. M. et al. "Parallel confocal detection of single molecules in real time." *Opt. Lett.* 33, 1026-1028 (2008); Korlach, J. et al. "Selective aluminum passivation for targeted immobilization of single DNA polymerase molecules in zero-mode waveguide nanostructures." *Proc. Natl. Acad. Sci. USA* 105, 1176-1181 (2008), the disclosures of which are incorporated herein by reference in their entireties). In one example single molecule, real-time (SMRT) DNA sequencing technology provided by Pacific Biosciences Inc can be utilized with the methods described herein. In some embodiments, a SMRT chip or the like may be utilized (U.S. Pat. Nos. 7,181,122, 7,302,146, 7,313,308, incorporated by reference in their entireties). A SMRT chip comprises a plurality of zero-mode waveguides (ZMW). Each ZMW comprises a cylindrical hole tens of nanometers in diameter perforating a thin metal film supported by a transparent substrate. When the ZMW is illuminated through the transparent substrate, attenuated light may penetrate the lower 20-30 nm of each ZMW creating a detection volume of about $1\times10^{-21}$ L. Smaller detection volumes increase the sensitivity of detecting fluorescent signals by reducing the amount of background that can be observed.

SMRT chips and similar technology can be used in association with nucleotide monomers fluorescently labeled on the terminal phosphate of the nucleotide (Korlach J. et al., "Long, processive enzymatic DNA synthesis using 100% dye-labeled terminal phosphate-linked nucleotides." *Nucleo-* sides, Nucleotides and Nucleic Acids, 27:1072-1083, 2008; incorporated by reference in its entirety). The label is cleaved from the nucleotide monomer on incorporation of the nucleotide into the polynucleotide. Accordingly, the label is not incorporated into the polynucleotide, increasing the signal: background ratio. Moreover, the need for conditions to cleave a label from a labeled nucleotide monomers is reduced.

An additional example of a sequencing platform that may be used in association with some of the embodiments described herein is provided by Helicos Biosciences Corp. In some embodiments, TRUE SINGLE MOLECULE SEQUENCING can be utilized (Harris T. D. et al., "Single Molecule DNA Sequencing of a viral Genome" Science 320: 106-109 (2008), incorporated by reference in its entirety). In one embodiment, a library of target nucleic acids can be prepared by the addition of a 3' poly(A) tail to each target nucleic acid. The poly(A) tail hybridizes to poly(T) oligonucleotides anchored on a glass cover slip. The poly(T) oligonucleotide can be used as a primer for the extension of a polynucleotide complementary to the target nucleic acid. In one embodiment, fluorescently-labeled nucleotide monomer, namely, A, C, G, or T, are delivered one at a time to the target nucleic acid in the presence DNA polymerase. Incorporation of a labeled nucleotide into the polynucleotide complementary to the target nucleic acid is detected, and the position of the fluorescent signal on the glass cover slip indicates the molecule that has been extended. The fluorescent label is removed before the next nucleotide is added to continue the sequencing cycle. Tracking nucleotide incorporation in each polynucleotide strand can provide sequence information for each individual target nucleic acid.

An additional example of a sequencing platform that can be used in association with the methods described herein is provided by Complete Genomics Inc. Libraries of target nucleic acids can be prepared where target nucleic acid sequences are interspersed approximately every 20 bp with adaptor sequences. The target nucleic acids can be amplified using rolling circle replication, and the amplified target nucleic acids can be used to prepare an array of target nucleic acids. Methods of sequencing such arrays include sequencing by ligation, in particular, sequencing by combinatorial probe-anchor ligation (cPAL).

In some embodiments using cPAL, about 10 contiguous bases adjacent to an adaptor may be determined. A pool of probes that includes four distinct labels for each base (A, C, T, G) is used to read the positions adjacent to each adaptor. A separate pool is used to read each position. A pool of probes and an anchor specific to a particular adaptor is delivered to the target nucleic acid in the presence of ligase. The anchor hybridizes to the adaptor, and a probe hybridizes to the target nucleic acid adjacent to the adaptor. The anchor and probe are ligated to one another. The hybridization is detected and the anchor-probe complex is removed. A different anchor and pool of probes is delivered to the target nucleic acid in the presence of ligase.

The sequencing methods described herein can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail below.

It will be appreciated that any of the above-described sequencing processes can be incorporated into the methods described herein. For example, the methods can utilize sequencing reagents having mixtures of one or more nucleotide monomers or can otherwise be carried out under conditions where one or more nucleotide monomers contact a target nucleic acid in a single sequencing cycle. In addition, the methods can utilize sequencing reagents having mixtures of oligonucleotides and ligase. Furthermore, it will be appreciated that other known sequencing processes can be easily by implemented for use with the methods and/or systems described herein.

Arrays and Sequencing Substrates

In some embodiments, an array refers to a substrate, such as a solid support, comprising a plurality of polynucleotides at distinguishable locations. Arrays can have one or more surfaces on which capture probes are distributed. In some embodiments, all of the capture probes distributed on an array surface are identical to each other. In other embodiments, some of the capture probes distributed on the array surface are identical to each other but different from one or more other capture probes distributed on the array surface. In still other embodiments, most or all of the capture probes distributed on an array surface are different from each other.

In embodiments where capture probes are distributed on an array surface, the capture probes can be distributed at sites. In some embodiments, a site is a feature having a plurality of copies of a particular capture probe. Thus, an array can comprise a plurality of sites or features. In some embodiments, a space separates each site from another such that the sites are noncontiguous. In other embodiments, the sites are contiguous. For some of the arrays described herein, sites can be present on the array surface at a density of greater than 10 sites per square millimeter. For other arrays, sites can be present on the array surface at a density of greater than 100 sites per square millimeter, greater than 1000 sites per square millimeter, greater than 10,000 sites per square millimeter, greater than 100,000 sites per square millimeter, greater than 1,000, 000 sites per square millimeter, greater than 10,000,000 sites per square millimeter, greater than 100,000,000 sites per square millimeter or greater than 1,000,000,000 sites per square millimeter.

In some embodiments, a site is surrounded by a border. In some embodiments, the border is a physical structure. In some embodiments, the border is a virtual structure that is produced during the imaging of the array surface. A border that surrounds a site will typically not intervene between two or more zones of the site.

In some embodiments, a site includes less area than the area of an array surface where nucleic acids are attached. In certain embodiments, a site includes less than 90%, less than 80%, less than 70%, less than 60%, less than 50%, less than 40%, less than 30%, less than 20%, less than 10%, less than 5%, less than 4%, less than 3%, less than 2%, less than 1%, less than 0.5%, less than 0.1%, less than 0.01%, less than 0.001%, less than 0.0001%, or less than 0.00001% of the totality of the area of an array surface where nucleic acids are attached. In certain embodiments, a site includes less than 90%, less than 80%, less than 70%, less than 60%, less than 50%, less than 40%, less than 30%, less than 20%, less than 10%, less than 5%, less than 4%, less than 3%, less than 2%, less than 1%, less than 0.5%, less than 0.1%, less than 0.01%, less than 0.001%, less than 0.0001%, or less than 0.00001% of the totality of a demarcated area on an array substrate, whether physically or virtually demarcated, where nucleic acids are attached.

In some embodiments, a site includes the entire area of an array surface where nucleic acids are attached. In certain embodiments, a site includes 100% of the totality of a demarcated area on an array substrate, whether physically or virtually demarcated, where nucleic acids are attached.

In various embodiments, a site includes the entire surface of an array (e.g. the entire surface of a substrate). In embodiments featuring copies of different fragments of a nucleic acid of interest that include distinguishable oligonucleotide index tags, a site can include the entire surface of a substrate.

In various embodiments, a site is a feature in the micron range, which can accommodate a plurality of polynucleotides detectable and/or resolvable by current imaging devices such as scanners. In some embodiments, the site is a feature of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4 s, 5, 6 square microns, 7, 8, 9, 10, 11, 12, 13, 14, 15, 20, 25, 30, 35, 40, 45, to about 50 square microns, or any size in between any of the foregoing values.

In other embodiments, a site is a feature in the sub-micron range that accommodates a plurality of polynucleotides detectable and/or resolvable by current imaging devices such as scanners. In some embodiments, the site is a feature size of about 1, 5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or about 1000 square nanometers, or any size in between any of the foregoing values.

It will be understood that several embodiments contemplate a site that is a feature in the picometer range. Accordingly, in some embodiments, the site is a feature of about 1, 5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or about 1000 square picometers, or any size in between any of the foregoing values.

In various embodiments, at least two polynucleotides are attached to a site. The embodiments of the present invention are not constrained to a particular maximum number of polynucleotides attached to a site. However, the maximum density of polynucleotides per unit area that can practically be resolved by an imaging device is a factor in the number of polynucleotides attached to a site.

With respect to some of the arrays described herein, the capture probes are coupled to an array surface. Such coupling can be via a direct attachment of the capture probe to the array surface. Direct attachment can include, but is not limited to, covalent attachment, non-covalent attachment, and adsorptive attachment. Alternatively, capture probes can be attached to the array surface via one or more intermediate molecules or particles. A probe can be attached to an array surface via the 3' end of the probe or via the 5' end of the probe. The attachment can block or inhibit enzymatic degradation of the probe. For example, attachment of a probe to a surface via the 3' end can prevent degradation of the probe by exonuclease III. Attachment of a probe to a surface via the 5' end can prevent degradation of the probe by lambda exonuclease or T7 exonuclease. Exemplary attachments are described, for example, in US Patent Application Publication No. 2006/0127930 A1, which is incorporated herein by reference and also in references listed below in regard to various arrays.

Depending on the deposition method, the capture probes can be distributed on the array surface in either a random or ordered distribution. For example, in some embodiments, capture probes are synthesized directly on the array surface such that the position of each capture probe is known. In such embodiments, the capture probes can be synthesized in any order that is desired. For example, capture probes may be grouped by functionality or binding affinity for a particular molecule. In other embodiments, the capture probes are synthesized then coupled to an array surface. In such embodiments, the capture probes can be coupled to specific areas of the array surface such that the specific areas of the array surface comprise a defined set of capture probes.

With respect to other arrays described herein, capture probes are not attached directly to the array, but rather, they are associated with the array through intermediate structures, such as linkers or particles. In such embodiments, a plurality of particles is distributed on the array. The plurality of particles can comprise particles that have one or more capture probes coupled thereto, as well as particles that do not have any capture probes coupled thereto. In some embodiments, all particles of the plurality of particles have one or more identical capture probes coupled thereto. In certain embodiments, where pluralities of particles are used, the capture probes coupled the particles are identical to each other such that all particles have the same identical capture probes coupled thereto. In other embodiments, where pluralities of particles are used, some or all of the capture probes coupled to the particles are different from each other such that some particles have capture probes coupled thereto that are different from the capture probes attached to other particles. In preferred embodiments, the particles are inanimate, non-living beads or microspheres. In further embodiments, the microspheres can be porous. The particles can be substantially non-compressible and non-deformable, for example, under the conditions used for fluidic manipulations, amplification or sequencing.

In some embodiments, the methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

In certain preferred embodiments, flow cells, flow chambers or other surfaces having one or more channels or pathways comprising one or more sites or locations in fluid communication with reagents that flow through the channels and/or pathways can be utilized in connection with any of the methods described herein. Flow cells and flow chambers are known in the art and designs can easily be adapted to fit the needs of the user. In preferred embodiments, the flow cell or flow chamber comprises a plurality of sites or locations that are spatially segregated sufficiently to permit resolution of signals produced at sites comprising polynucleotides that have been differentially processed. It will be appreciated that in most embodiments, spatial segregation need not be implemented by having a physical space between sites. For example, in some embodiments, spatial segregation is implemented by providing a virtual boundary between contiguous sites.

All of the embodiments described herein can be implemented with arrays that utilize particles and those that do not.

As with non-particle arrays, arrays that utilize particles can be constructed from a variety of substrates with a variety of design features.

In some embodiments, the particles are distributed on the array such that one or more particles end up in a depression present on the array. In some embodiments, the depressions are configured to hold a single particle. In other embodiments, the depressions are configured to hold thousands, or even millions, of particles.

The plurality of particles can be distributed on the array so that they are orderly or randomly distributed. In particular embodiments, an array can comprise particles carrying different functionalities that are distributed on an array comprising a patterned surface of sites, each capable of holding an individual particle. In some embodiments, one or more particles are present in wells of the array substrate.

Some of the arrays described herein include one or more patterned surfaces. In such embodiments, the patterned surface may comprise depressions, such as wells, grooves, channels or indentations. Depressions can be sized so as to accommodate as few as one particle or as many as several million particles. As discussed above, however, in many embodiments, particles are not used.

In further embodiments an array can comprise a composite array (array of subarrays) as described in U.S. Pat. No. 6,429,027 or U.S. Pat. No. 5,545,531, the disclosures of which are hereby incorporated expressly by reference in their entirety. Composite arrays can comprise a plurality of individual arrays on a surface of the array or distributed in depressions present on the array surface. The plurality of individual arrays on a surface of the array or distributed in depressions present on the array surface can be referred to as subarrays. For example, in a composite array, a single subarray can be present in each of a plurality of depressions present on the array. In other embodiments, multiple subarrays can be present in each depression of a plurality of depressions present on the array. Individual subarrays can be different from each other or can be the same or similar to other subarrays present on the array. Accordingly, in some embodiments, the surface of a composite array can comprise a plurality of different and/or a plurality of identical, or substantially identical, subarrays. Moreover, in some embodiments, the surface of an array comprising a plurality of subarrays can further comprise an inter-subarray surface. By "inter-subarray surface" or "inter-subarray spacing" is meant the portion of the surface of the array not occupied by subarrays. In some embodiments, "inter-subarray surface" refers to the area of array surface between a first subarray and an adjacent second subarray.

Subarrays can include some or all of the features of the arrays described herein. For example, subarrays can include depressions that are configured to contain one or more particles. Moreover, subarrays can further comprise their own subarrays. In some embodiments, subarrays can include individual or pluralities of flow cells or flow chambers.

Exemplary arrays that can be utilized in combination with the methods and compositions described herein include, without limitation, those described in U.S. Pat. No. 6,355,431; U.S. Pat. No. 6,327,410; U.S. Pat. No. 6,770,441; US Published Patent Application No. 2004/0185483; US Published Patent Application No. 2002/0102578 and PCT Publication No. WO 00/63437, each of which is incorporated herein by reference in its entirety. In some embodiments, beads can be located at sites or locations, such as wells, on a solid-phase support, whereby each site or location accommodates a single bead.

Any of a variety of other arrays known in the art or methods for fabricating such arrays can be used. Commercially available microarrays that can be used include, for example, an Affymetrix® GeneChip® microarray or other microarray synthesized in accordance with techniques sometimes referred to as VLSIPS™ (Very Large Scale Immobilized Polymer Synthesis) technologies as described, for example, in U.S. Pat. Nos. 5,324,633; 5,744,305; 5,451,683; 5,482,867; 5,491,074; 5,624,711; 5,795,716; 5,831,070; 5,856,101; 5,858,659; 5,874,219; 5,968,740; 5,974,164; 5,981,185; 5,981,956; 6,025,601; 6,033,860; 6,090,555; 6,136,269; 6,022,963; 6,083,697; 6,291,183; 6,309,831; 6,416,949; 6,428,752 and 6,482,591, each of which is hereby incorporated by reference in its entirety. A spotted microarray can also be used in a method of the invention. An exemplary spotted microarray is a CodeLink™ Array available from Amersham Biosciences. Another microarray that is useful in the invention is one that is manufactured using inkjet printing methods such as SurePrint™ Technology available from Agilent Technologies.

Arrays described herein can also have a variety of surfaces. In some embodiments, an array surface can comprise a fiber optic bundle. Arrays having planar surfaces or surfaces with one or more depressions, channels or grooves are particularly useful. In addition, some of the arrays have a non-porous surface. In some embodiments, the entire array is non-porous. In other embodiments, the array has at least one porous or semi-porous surface but is primarily non-nonporous.

Preferred materials for array substrates include, but are not limited to glass, silicon, plastic or non-reactive polymers. Arrays described herein can be rigid or flexible. In some embodiments, the array is rigid, whereas in other embodiments, the array is not rigid but comprises at least one rigid surface. Other arrays contemplated herein can comprise a flexible array substrate having a flexible support, such as that described in U.S. patent application Ser. No. 10/285,759, now U.S. Pat. No. 7,422,911, the disclosures of which are hereby incorporated expressly by reference in their entireties.

Computer Implemented Embodiments

In some embodiments, one or more steps can be carried out by a computer. In certain embodiments, a computer can be used to determine the composition of sequencing reagents in one or more delivery steps. As will be appreciated, the extension of a polynucleotide complementary to a target nucleic acid using the methods described herein can be determined by the sequence of the target nucleic acid and the composition of the sequencing reagents. In some embodiments, at least a portion of a target nucleic acid may be known. Determining the composition of sequencing reagents may advantageously reduce the number of cycles that are needed to reach a sequence of interest in a target nucleic acid. In one example where a target nucleic acid contains a homopolymeric region (e.g. poly-T stretch) before a sequence of interest, a sequencing reagent may contain nucleotide monomers (e.g. sequencing reagent will contain: A) that will not limit extension of the polynucleotide complementary to the target nucleic acid before reaching the sequence of interest. In some embodiments, determinations can be made before and/or during a sequencing run.

In other embodiments, low resolution sequence representations can be provided to a computer that is programmed to compare or otherwise linked to a system that contains one or more functional portions of executable code that can be used to compare sequence data representations to each other, determine an actual sequence of a target nucleic acid at single nucleotide resolution, identify samples from which a low resolution sequence representation was derived or the like. In some embodiments, a computer can be used to predict a low resolution sequence representation of a particular known sequence. In additional embodiments, a computer can be used to predict a particular known sequence from a low resolution sequence representation.

Example computer systems that are useful in the invention include, but are not limited to, personal computer systems, such as those based on Intel®, IBM®, or Motorola® microprocessors; or work stations such as a SPARC workstation or UNIX workstation. Useful systems include those using the Microsoft Windows, UNIX or LINUX operating system. The systems and methods described herein can also be implemented to run on client-server systems or wide-area networks such as the Internet.

A computer system useful in the invention can be configured to operate as either a client or server and can include one or more processors which are coupled to a random access memory (RAM). Implementation of embodiments of the present invention is not limited to any particular environment or device configuration. The embodiments of the present invention may be implemented in any type of computer system or processing environment capable of supporting the methodologies which are set forth herein. In particular embodiments, algorithms can be written in MATLAB, C or C++, or other computer languages known in the art.

In some embodiments described herein, a computer can be used to store one or more of the representations and the actual sequence. In some embodiments, the computer can be programmed, or otherwise instructed, to transmit one or more of the representations, the actual sequence or other relevant information to a user, another computer, a database or a network. In additional embodiments, the computer can also be programmed, or otherwise instructed, to receive relevant information from a user, another computer, a database or a network. Such information can include data, such as signals or images, obtained from a sequencing method, one or more reference sequences, characteristics of an organism of interest or the like.

Applications

Methods described herein are a useful tool in obtaining the molecular signature of a sequence, such as a DNA sequence. The sequence information that can be obtained using the methods described herein can be used in applications involved in genotyping, expression profiling, capturing alternative splicing, genome mapping, amplicon sequencing, methylation detection and metagenomics.

In one example, low resolution sequence representations can provide a signature for different nucleic acids in a sample. Accordingly, the actual sequence of a target nucleic acid need not be determined at single-nucleotide resolution and, instead, a low resolution sequence representation of the nucleic acid can be used. In some embodiments, the low resolution sequence representations comprise one or more positions where single nucleotide assignments cannot be made. In other embodiments, the low resolution representations comprise one or more regions where no nucleotide assignment or a completely ambiguous nucleotide assignment is made interspersed by regions where at least one position is assigned with single base resolution. In some embodiments, these regions contain multiple consecutive positions (high resolution sequence islands) that are assigned with single base resolution. In some embodiments, the high resolution sequence island may contain one or more areas of sequence ambiguity, however, high resolution sequence islands are often preferred.

In numerous embodiments, a low resolution sequence representation can be used to determine the presence or absence of a target nucleic acid in a particular sample or to quantify the amount of the target nucleic acid. Exemplary applications include, but are not limited to, expression analysis, identification of organisms, or evaluation of structure for chromosomes, expressed RNAs or other nucleic acids.

In particular embodiments, low resolution sequence representations for one or more target mRNA molecules can be used to determine expression levels in one or more samples of interest. So long as the low resolution sequence representations are sufficiently indicative of the mRNA, the actual sequence need not be known at single nucleotide resolution. For example, if a low resolution sequence representation distinguishes a target mRNA from all other mRNA species expressed in a target sample and in a reference sample, then comparison of the low resolution sequence representations from both samples can be used to determine relative expression levels. Target nucleic acids used in expression methods can be obtained from any of a variety of different samples including, for example, cells, tissues or biological fluids from organisms such as those set forth above. Presence or absence, or even quantities of target nucleic acids can be determined for samples that have been treated with different chemical agents, physical manipulations, environmental conditions or the like. Alternatively or additionally, samples can be from organisms that are experiencing any of a variety of diseases, conditions, developmental states or the like. Typically, a reference sample and target sample will differ in regard to one or more of the above factors (for example, treatment, conditions, species origin, or cell type).

In particular embodiments, low resolution sequence representations for target nucleic acids obtained from a particular organism can be used to characterize or identify the organism. For example, a pathogenic organism can be identified in an environmental sample or in a clinical sample from an individual based on at least one low resolution sequence representation for a target nucleic acid from the sample. So long as the one or more low resolution sequence representations are sufficiently indicative of the organism, the actual sequence need not be known at single nucleotide resolution. For example, if a low resolution sequence representation distinguishes a pathogenic bacterial strain from other bacteria, then comparison of the low resolution sequence representations from the sample of interest to low resolution sequence representations from reference samples or from a database can be used to detect presence or absence of the pathogenic bacterial strain.

In another example, a low resolution sequence representation of the 16S rRNA gene can be used to characterize and/or identify an organism. The 16S RNA gene is highly conserved across species and contains highly conserved sequences that may be interspersed with variable sequences that may be species-specific. In some embodiments, a low resolution sequence representation of a 16S rRNA gene may identify a particular organism through the pattern of uniform and variable regions that may be obtained at low resolution. In other embodiments, the composition of particular sequencing reagents can be determined to obtain sequence information at low resolution in highly conserved regions of the 16S rRNA gene, and to obtain sequence information at a higher resolution in variable regions of the 16S rRNA gene.

The determination of particular compositions for sequencing reagents can be made during the sequencing run. In one embodiment, a low resolution sequence representation of a highly conserved region can be recognized and the composition of sequencing reagents adjusted so that the number of limited extension flow steps for a polynucleotide complementary to the target nucleic acid to be extended through the highly conserved region can be minimized. For example, to ensure that limited extension of a polynucleotide continues in a highly conserved region, specific nucleotide monomers may be included in a sequencing reagent, alternatively, specific nucleotide monomers comprising reversibly terminating moieties can be absent from a sequencing reagent. As sequence information is obtained, the transition from the highly conserved region to the variable region can be recognized and the composition of sequencing reagents can be adjusted to obtain sequence information at a higher resolution. For example, sequencing reagents in flow steps for limited extension of the polynucleotide complementary to the target nucleic acid may be adjusted so that extension of the polynucleotide in such steps is reduced. In addition, sequencing reagents in flow steps for reading at least one base incorporated into a polynucleotide complementary to a target nucleic acid can be adjusted to obtain sequence information at single nucleotide resolution. For example, the number of differently-labeled types of nucleotide monomers comprising reversibly terminating moieties can be increased in such reagents.

In more embodiments, the structure of a chromosome, RNA or other nucleic acid can be determined based on low resolution sequence representations. For example, if a low resolution sequence representation distinguishes a chromosomal region from other regions of a chromosome, then comparison of the low resolution sequence representations from a target sample and a reference sample for which the chromosome structure is known can be used to identify insertions, deletions or rearrangements in the target sample. Similarly, if a low resolution sequence representation distinguishes a target mRNA isoform (i.e. alternative splice product of a gene) from another mRNA isoform expression product of the same gene, then comparison of the low resolution sequence representations for both isoforms can be used to determine presence or absence of the target isoform. Target nucleic acids used to determine chromosome or RNA structure can be obtained from any of a variety of samples including, but not limited to those exemplified above.

In particular embodiments, low resolution sequence representations can be obtained for a plurality of target nucleic acids that are fragments of a larger nucleic acid such as a genome. In such embodiments, the sequence information for the individual fragments can be used to determine the actual sequence of the larger nucleic acid at single nucleotide resolution. For example, multiple low resolution sequence representations from each feature can be used to determine the actual sequence of each fragment target nucleic acid at single nucleotide resolution. The actual sequence of each fragment can then be used to determine the actual sequence of the larger sequence, for example, by alignment to a reference sequence or by de novo assembly methods. In an alternative embodiment, the low resolution sequence representations from different features can be used directly to determine the actual sequence of the larger sequence, for example, using pattern matching methods.

In more embodiments, low resolution sequence representation of a target nucleic acid can provide a scaffold on which to map other sequence representations of a target nucleic acid. In one example, a target nucleic acid is fragmented, universal priming sites are attached to the fragments, and the fragments are concatamerized. A low resolution sequence representation of the concatamerized target nucleic acid can be obtained using the methods described herein. In addition, multiple sequence representations may be obtained from the target nucleic acid using the multiple universal priming sites. The multiple sequence representations may be ordered and aligned using the low resolution sequence representations of the concatamerized target nucleic acid.

In certain embodiments, methylated cytosine residues may be identified in a target nucleic acid. For example, a target nucleic acid can be treated under conditions where cytosine residues are converted to uracil residues, but methylcytosine residues are protected, such as using bisulfite treatment of DNA. Exemplary methods are described in Olek A., *Nucleic Acids Res.* 24:5064-6, (1996) or Frommer et al., *Proc. Natl. Acad. Sci. USA* 89: 1827-1831 (1992). In some embodiments, a sequencing reagent for a flow step for limited extension may allow limited extension until a cytosine residue is reached by the polymerase in the target nucleic acid. For example, the sequencing reagent may contain a GTP comprising a reversibly terminating moiety or, alternatively, the sequencing reagent may contain no GTP. At least one nucleotide may then be identified in at least one subsequent flow step, for example, by using a nucleotide having a distinguishable label. Thus a low resolution sequence representation of methylated cytosines in a target nucleic acid can be obtained. Additionally or alternatively, a sequencing reagent for a flow step for limited extension may allow limited extension until a uracil residue is reached by the polymerase in the target nucleic acid. For example, the sequencing reagent may contain an ATP comprising a reversibly terminating moiety or, alternatively, the sequencing reagent may contain no ATP. At least one nucleotide may then be identified in at least one subsequent flow step, for example, by using a nucleotide having a distinguishable label. Thus a low resolution sequence representation of non-methylated cytosines in a target nucleic acid can be obtained.

In particular embodiments, a first low resolution sequence representation can be obtained from a target nucleic acid that has been treated under conditions wherein cytosine residues are converted to uracil residues and a second low resolution sequence representation can be obtained from a sample of the target nucleic acid that has not been treated in this way. The first low resolution sequence representation can be compared to the second low resolution sequence representation and differences in methylation status can be determined based on differences in the number of cytosines, uracils or both.

The position of methylated cytosines in a target sequence can be identified based on a three nucleotide sequence in a low resolution sequence representation. For example, the three nucleotide sequence can be represented as 5'-NCG-3'. In this example, N is one of A, C, T or G as determined based on the identity of the nucleotide that is incorporated at a position that follows a methylated cytosine during a sequencing run, and the presence of G is inferred from the knowledge that methylated cytosines are present in CpG islands. As illustrated by this example, inferred sequence information can increase the resolution of a sequence representation or otherwise improve the information content present in a sequence representation.

In more embodiments, methods described herein can be utilized to provide higher resolution sequence representations of a target nucleic acid. Such methods can include obtaining at least two different low resolution sequence representations of a target nucleic acid and combining the predicted representations. One example can include obtaining low resolution sequence representations where the sequential order in which a series of limited dark extension steps is varied between a first sequencing run and a second sequencing run. For example, a first sequencing run can include iterations of a series of four limited dark extension steps and at least one limited read extension step, where the limited dark extension steps reagents may contain $1^{st}$: A,C,G; $2^{nd}$: A,C,T; $3^{rd}$: A,G,T; $4^{th}$: T,C,G. The second sequencing run can include similar conditions as the first run, but the series of limited dark extension steps reagents may be $1^{st}$: A,C,T; $2^{nd}$: A,C,G; $3^{rd}$: A,G,T; $4^{th}$: T,C,G. The two low resolution sequence representations may be combined to provide a higher resolution sequence representation. Some such methods can include additional sequencing runs on the target nucleic acid with different permutations of the limited dark extension step reagents. As will be appreciated, a sequence representation having an even higher resolution can be obtained where the number of sequencing runs on a particular target nucleic acid is increased. For example, a sequence representation produced by combining three lower resolution sequence representations will typically have a higher resolution than a sequence representation produced by combining two lower resolution sequence representations. In some embodiments, a sequence representation produced by combining three lower resolution sequence representations can have single nucleotide resolution.

In more embodiments, a first and second sequencing run can produce different low resolution sequencing representations of a target nucleic acid by initiating extension of a polynucleotide complementary to a target nucleic acid at different positions in the target nucleic acid.

In more embodiments, methods described herein can be applied to pair-ended sequencing methods. See, for example, U.S. Patent Publication No. 20060292611 "Paired end sequencing" filed on Dec. 28, 2006, hereby incorporated by reference in its entirety. Pair-end sequencing methods can include preparing a target nucleic acid, and/or plurality of target nucleic acids by fragmenting larger nucleic acid molecules and flanking the nucleic acid fragments with adaptors to allow sequencing reactions to be primed from each end of the adaptor-flanked molecules.

In one embodiment, a sequencing run in a pair-ended sequencing method can include cycles that include limited dark extension steps or limited read extension steps. For example, a series of limited read extension steps can be performed at the two ends of a target nucleic acid, followed by a series of limited dark extension steps, followed by a series of limited read steps. In this example, a sequence representation can be obtained that includes determined regions for the two ends of the target nucleic acid, and the sequence representation between the two determined regions at each end of the sequence representation can include dark regions and at least one further determined region.

In an example, a sequencing run is performed in a paired-end sequencing methodology, where the sequencing run includes cycles of limited read extension steps and limited dark extension steps. In a first series of cycles that include limited read extension steps, at least 1, 5, 10, 20, 30, 40, 50, 60, 70, 80, 90, 100, 110, 120, 130, 140, 150, 160, 170, 180, 190, and 200 cycles are performed to obtain sequence information at each end of the target nucleic acid. In a series of subsequent cycles that include limited dark extension steps, at least 1, 5, 10, 20, 30, 40, 50, 60, 70, 80, 90, 100, 110, 120, 130, 140, 150, 160, 170, 180, 190, 200 cycles are performed. In a series of subsequent cycles that include limited read extension steps, at least 1, 5, 10, 20, 30, 40, 50, 60, 70, 80, 90, 100, 110, 120, 130, 140, 150, 160, 170, 180, 190, and 200 cycles are performed. In this example, a sequence representation having determined regions for the two ends of the target nucleic acid can be obtained. The sequence representation can further include at least one determined region and at least one dark region between the two determined regions for each end of the target nucleic acid.

In more embodiments, a sequence representation can be obtained by comparing a first low resolution sequence representation and a second low resolution sequence representation to determine a sequence representation having a higher resolution than either the first low resolution sequence representation or the second low resolution sequence representation. In such embodiments, low resolution sequence representations can include an ordered series of determined regions and dark regions. As will be appreciated, a determined region can include a portion of a sequence representation where the identity of a monomer at a particular position can be determined. In some embodiments, the identity of a monomer can be determined to be one or more nucleotide types. In some embodiments, a monomer can be at least one, but no more than three nucleotide types. In some embodiments, a monomer can be at least two, but no more than three nucleotide types. In some embodiments, a monomer can be three nucleotide types. A dark region within a sequence representation can include a portion of a sequence representation obtained using dark extension steps described herein. In some embodiments, the identity of the monomers in a dark region may be degenerate.

Barcode Sequences

Some embodiments of the present invention include methods and compositions relating to barcode sequences. As used herein, a "barcode sequence" can refer to a sequence representation of a target sequence. In some embodiments, the barcode sequence can be used to identify a target sequence. In one embodiment, a barcode generated by catenating the sequences produced by two or more limited extension steps. In some embodiments, a barcode sequence can include a low resolution representation of a target sequence. For example, a barcode sequence can include an ordered series of determined regions and at least one dark region. In some embodiments, at least a portion of the sequence of the dark region may be undetermined. In some embodiments, a barcode sequence can include an ordered series of determined regions and no dark regions. In still other embodiments, a bar code sequence can include an ordered series of determined regions, at least some of which are separated by a representation indicative of the distance between two determined regions. Barcode sequence representations can be obtained using the methods provided herein.

A target sequence can be identified from a barcode sequence by a variety of methods. For example, a target sequence can be identified by comparing at least a portion of at least one determined region of the barcode sequence to a target sequence. In another example, a target sequence can be identified using the interval between determined regions of a barcode sequence. For example, at least two consecutive determined regions may be mapped to a target sequence to obtain the approximate size of the interval between two determined regions. The size of the interval may be used to identify or assist in the identification of the target sequence. Such methods may be particularly advantageous in applications where the sequence of determined regions comprise repetitive sequences and/or the sequence of at least one determined region is present in the target sequence in multiple copies.

In some embodiments, at least a portion of a barcode sequence can be compared to a reference sequence or a plurality of reference sequences, such as those obtained from an electronic database or a biological database. In some embodiments, a reference sequence can include the sequence of a target sequence. In some embodiments, a reference sequence can include a sequence representation of the target sequence. For example, a reference sequence can include the predicted sequence representation of a target sequence, where the sequence representation of a target sequence is obtained using methods described herein.

In some embodiments, a barcode sequence is analyzed by comparing the barcode sequence to reference sequences, for example, reference nucleotide sequences. Sequences can be compared utilizing a variety of methods. Examples of methods include utilizing a heuristic algorithm, such as a Basic Local Alignment Search Tool (BLAST) algorithm, a BLAST-like Alignment Tool (BLAT) algorithm, or a FASTA algorithm. Examples of sequence analysis software that can be used with some of the methods and systems described herein include the GCG suite of programs (Wisconsin Package Version 9.0, Genetics Computer Group (GCG), Madison, Wis.), BLASTP, BLASTN, and BLASTX (Altschul et al., J. Mol. Biol. 215:403-410 (1990); BLAT (Kent, W James (2002). "BLAT—the BLAST-like alignment tool." Genome research 12 (4): 656-64); DNASTAR (DNASTAR, Inc. 1228 S. Park St. Madison, Wis. 53715 USA); and the FASTA program incorporating the Smith-Waterman algorithm (W. R. Pearson, Comput. Methods Genome Res., [Proc. Int. Symp.] (1994), Meeting Date 1992, 111-20. Editor(s): Suhai, Sandor. Publisher: Plenum, New York, N.Y.).

Some embodiments described herein include databases. Databases can be used in comparing the barcode sequence with a population of database sequences. Databases can contain a population of reference sequences. The population can include a variety of types of reference sequences, for example, nucleotide sequences, polypeptide sequences, or mixtures thereof.

Although some of the analyses of the barcode sequence are described in connection with database sequences, it will be appreciated that it is not necessary to compare the barcode sequence to a population of sequences in a database. In some embodiments, the barcode sequence can be compared to one or more reference sequences obtained from any source. For example, the barcode sequence can be compared to one or more sequences generated by sequencing nucleic acids from one or more reference organisms either prior to or in parallel with generating the barcode sequence data.

In some embodiments, a population of reference sequences can be indexed. In preferred embodiments, a database can be pre-indexed for use with the methods and compositions described herein. Indexing can improve the efficiency of accessing the sequences and/or attributes associated with such sequences in a database. An index can be created from a population of database sequences using one or more characteristics of each sequence. Such characteristics can be intrinsic or extrinsic to a database sequence. Intrinsic characteristics can include the primary structure of a sequence, and secondary structure of a sequence. The secondary structure of a polypeptide sequence or a nucleic acid sequence can be determined by methods well known in the art, such as methods using predictive algorithms. Extrinsic characteristics can include a variety of traits, for example, the source of a sequence, and the function of a sequence.

In one embodiment, a reference sequence can be indexed by particular characteristics using a hierarchical association between other reference sequences. A hierarchical association between reference sequences can be created for any characteristic of the reference sequences. For example, the primary structure of a reference sequence can be used to group a reference sequence according to sequence identity with other reference sequences into at least subgroups, groups, and supergroups.

In a preferred embodiment, a population of database sequences can be indexed according to the source of reference sequences using a hierarchical association between other reference sequences. In one embodiment, the source of a sequence can be characterized using phylogenetic traits that include the kingdom, phylum, class, order, family, genus, species, subspecies, and strain of an organism in which the sequence can be found.

The identity of the source of a target nucleic acid can be identified, or otherwise characterized, by one or a plurality of traits and such traits will vary with the application of the methods and systems described herein. In one embodiment, the source of a sequence can be identified by comparing the barcode sequence to reference sequences grouped by a hierarchal association. Exemplary hierarchal grouping can be made using phylogenetic traits that include, but are not limited to, the kingdom, phylum, class, order, family, genus, species, subspecies, and/or strain of an organism. In such embodiments, the identity of the source of a target nucleic acid can be identified by an association with any level of the hierarchal association. In other embodiments, a hierarchal association need not be used. In such embodiments, identification of the target nucleic acid can be made by comparing the sequence to one or more reference sequences that are ungrouped or placed in non-hierarchal groups.

Methods of Generating Overlapping Sequencing Reads
Overlapping Sequencing Reads from Different Sequencing Primers Several embodiments of the methods and compositions described herein involve producing a set of overlapping or adjacent sequencing reads and assembling those sequencing reads into a contiguous nucleotide sequence.

In some embodiments, nucleic acid of interest is fragmented and ligated to universal adaptors. Multiple copies of each fragment are made, for example, by amplification. The multiple copies derived from the same fragment are ligated to a common indexing tag, common amplification primers, such as P5 and P7, and different sequencing primer sites. Subsequently, the fragment copies are hybridized to an array for further amplification, such as by bridge PCR. Sequencing is initiated by adding a first distinct sequencing primer, which sequences the index tag and first few bases of the fragment. While this sequencing run proceeds with a head start, the second distinct sequencing primer is added to initiate a lagging sequencing run of the fragment. The process is continued in a temporally staggered fashion by sequentially adding distinct sequencing primers at some time apart. Consequently, overlapping sequencing reads of varying lengths are generated, which can be assembled into a contiguous nucleotide sequence of the fragment.

In such embodiments, sequencing of multiple copies of a fragment may be performed with or without spatial segregation. Use of distinct sequencing primers permits sequencing initiation of some but not all of the fragment copies. For example, the multiple copies of the fragments which are hybridized to different sequencing primer sites can be attached to the same site on an array and sequencing is performed by adding different sequencing primers to the site at different times.

In some embodiments, overlapping sequencing reads are generated as described above except sequencing is performed with limited extensions as shown in FIG. 12. Any of the methods for performing sequencing that include limited extensions as described herein can be employed to generate sets of overlapping or adjacent sequencing reads as described above. Such sequencing reads can be used to determine the contiguous sequence of a nucleic acid fragment or portion thereof.

Overlapping Sequencing Reads from the Same Sequencing Primers

Other methods for generating overlapping sequencing reads include ligating multiple copies of a nucleic acid fragment to the same sequencing primer site and a common index tag. In preferred embodiments, different fragments are ligated to the same sequencing primer site but are distinguishable by their different ligated index tags. As a result, different fragments or copies thereof can be pooled and distributed among spatially segregated sites or locations on an array, for example by hybridizing the pooled fragments to separate or individual lanes of a flow cell.

In some embodiments, sequencing is performed by adding the common sequencing primer to each spatially segregated site or location and then performing a number of limited extensions according to one or more of the methods described herein during sequencing at each site. In some embodiments, the number of limited extensions performed at each site varies. In some embodiments, the number of limited extensions to be performed at each site is based on the estimated number of extensions required to generate a set of overlapping or adjacent sequencing reads as exemplified in FIG. 13. As shown in FIG. 13, the number of limited extensions is increased at each site so as to generate a set of overlapping sequencing reads. Consequently, overlapping sequencing reads of varying lengths are generated for the different fragments, which can be distinguished by their unique index tags, and assembled into a contiguous nucleotide sequence of the fragments.

In some embodiments, methods of generating overlapping sequences are performed by adding the common sequencing primer to each spatially segregated site or location at the same time or substantially the same time and a different number of limited extensions occur in a plurality of the spatially segregated sites or locations such that overlapping sequencing reads can be obtained. In other embodiments, the common sequencing primer is provided at different times and/or different sequencing primers are used.

It will be appreciated that, in some embodiments where the polynucleotides are not associated at the same site, index tags can be utilized to identify the identical or related fragments or target nucleic acids. In some embodiments, oligonucleotide index tags may be added in conjunction with adaptors. In other embodiments, the oligonucleotide index tags are not added in conjunction with the adaptors, but rather, are added separately or in conjunction with a primer, primer binding site or other component. In other embodiments, no index tag is used, but rather, a pair-end read is performed. The read from the first end comprises a portion of the sequence of interest and the read from the other (second) end is utilized as a tag to identify the fragment from which the first read originated.

EXAMPLES

Example 1

Limited Dark Extension with Three Nucleotide Monomers

This example illustrates a method of sequencing that comprises a cycle that includes: (1) a limited dark extension step with three nucleotide monomers only, and (2) two limited read extension steps with nucleotide monomers comprising labels and reversibly terminating moieties.

A single limited dark extension step is performed. The limited dark extension sequencing reagent (first sequencing reagent) including the nucleotide monomers, A, C, G, is delivered to a target nucleic acid in the presence of DNA polymerase. A polynucleotide strand complementary to the target nucleic acid may incorporate the A, C, and G nucleotide monomers. The first sequencing reagent is removed.

Two limited read steps are performed. The limited read extension sequencing reagent (second sequencing reagent) including the nucleotide monomers, $A^T$, $C^T$, $G^T$, $T^T$ is delivered to the target nucleic acid in the presence of DNA polymerase (superscript "T" represents a reversibly terminating moiety). The second sequencing reagent is removed. The incorporation of a particular type of nucleotide monomer into the polynucleotide complementary to the target nucleic acid is detected. The reversibly terminating moiety of the incorporated nucleotide is removed. The limited read extension step is repeated. The limited dark extension step and limited read extension steps are repeated for a second, third and forth cycle.

Table 1 shows an example target nucleic acid, "GGATCA-CAGGCGGAAAC" (SEQ ID NO:01), and sequence information that may be derived from four cycles, wherein each cycle comprises a single limited dark extension step followed by two limited read extension steps, and wherein a first sequencing reagent includes A, C, G, and a second sequencing reagent includes labeled $A^T$, $C^T$, $G^T$, $T^T$. "X" represents an unknown number and/or type of incorporated nucleotides. In the 3$^{rd}$ cycle shown in Table 1, the limited dark extension step does not extend the polynucleotide complementary to the target nucleic acid. Here, "X" of "G-X-T" represents no limited dark step extension before the subsequent limited read step.

TABLE 1

| | Target nucleic acid | | | | | | | | | | | | | | | | |
|---|---|---|---|---|---|---|---|---|---|---|---|---|---|---|---|---|---|
| | G | G | A | T | C | A | C | A | G | G | C | G | G | A | A | A | C |
| 1$^{st}$ cycle | X | | T | A | | | | | | | | | | | | | |
| 2$^{nd}$ cycle | X | | T | A | X | T | G | | | | | | | | | | |
| 3$^{rd}$ cycle | X | | T | A | X | T | G-X-T | C | | | | | | | | | |

TABLE 1-continued

| | Target nucleic acid | | | | | | | | | | | | | | | |
|---|---|---|---|---|---|---|---|---|---|---|---|---|---|---|---|---|
| | G | G | A | T | C | A | C | A | G | G | C | G | A | A | A | C |
| 4th cycle | X | T | A | X | T | G-X-T | C | | X | | | | T | T | | |
| Sequence | X | T | A | X | T | G-X-T | C | | X | | | | T | T | | |

Example 2

Limited Dark Extension with Reversibly Terminating Nucleotide Monomers

This example illustrates a method of sequencing that comprises a cycle that includes: (1) a limited dark extension step with a nucleotide monomer comprising a reversible terminating moiety, and (2) one limited read extension step with nucleotide monomers comprising labels and reversibly terminating moieties.

A single limited dark extension step is performed. The limited dark extension sequencing reagent (first sequencing reagent) including the nucleotide monomers, A, C, G, $T^T$ is delivered to a target nucleic acid in the presence of DNA polymerase. A polynucleotide strand complementary to the target nucleic acid may incorporate the A, C, G, and $T^T$ nucleotide monomers. The first sequencing reagent is removed. The reversible terminating moiety of an incorporated nucleotide is removed.

A limited read step is performed. The limited read extension sequencing reagent (second sequencing reagent) including the nucleotide monomers, $A^T$, $C^T$, $G^T$, $T^T$ is delivered to the target nucleic acid in the presence of DNA polymerase (superscript "T" represents a reversibly terminating moiety). The second sequencing reagent is removed. The incorporation of a particular type of nucleotide monomer into the polynucleotide complementary to the target nucleic acid is detected. The reversibly terminating moiety of the incorporated nucleotide is removed. The limited dark extension step and limited read extension step are repeated.

Table 2 shows an example target nucleic acid (SEQ ID NO:01) and sequence information that can be derived from four cycles, wherein each cycle comprises a single limited dark extension step followed by a single limited read extension step, and wherein a first sequencing reagent includes A, C, G, and $T^T$, and a second sequencing reagent includes labeled $A^T$, $C^T$, $G^T$, $T^T$. "X" represents an unknown number and/or type of incorporated nucleotides. In the 3rd cycle shown in Table 2, the limited dark extension step does not extend the polynucleotide complementary to the target nucleic acid. Here, "X" of "G-X-T" represents no limited dark step extension before the subsequent limited read step.

Example 3

Limited Dark Extension with Reversibly Terminating Oligonucleotides

This example illustrates a method of sequencing that includes a cycle that includes: (1) a limited dark extension step where an oligonucleotide is ligated to a polynucleotide complementary to at least a portion of a target nucleic acid, and (2) two limited read extension steps with nucleotide monomers comprising labels and reversibly terminating moieties.

A single limited dark extension step is performed. The limited dark extension sequencing reagent (first sequencing reagent) including a plurality of degenerate oligonucleotide comprising reversibly terminating moieties is delivered to a target nucleic acid in the presence of DNA ligase. An oligonucleotide is ligated to a polynucleotide complementary to the target nucleic acid, such that the polynucleotide complementary to the target nucleic acid is extended. The first sequencing reagent is removed. The reversible terminating moiety of the incorporated oligonucleotide is removed.

Two limited read steps are performed. The limited read extension sequencing reagent (second sequencing reagent) including the nucleotide monomers, $A^T$, $C^T$, $G^T$, $T^T$ is delivered to the target nucleic acid in the presence of DNA polymerase (superscript "T" represents a reversibly terminating moiety). The second sequencing reagent is removed. The incorporation of a particular type of nucleotide monomer into the polynucleotide complementary to the target nucleic acid is detected. The reversibly terminating moiety of the incorporated nucleotide is removed. The limited read extension step is repeated. The limited dark extension step and limited read extension steps are repeated.

Table 3 shows an example target nucleic acid (SEQ ID NO:01) and sequence information that can be derived from three cycles, wherein each cycle comprises a single limited dark extension step followed by two limited read extension steps, and wherein a first sequencing reagent includes a plurality of degenerate 4-mers, and a second sequencing reagent includes labeled $A^T$, $C^T$, $G^T$, $T^T$. "X" represents an unknown type of nucleotide.

TABLE 2

| | Target nucleic acid | | | | | | | | | | | | | | | |
|---|---|---|---|---|---|---|---|---|---|---|---|---|---|---|---|---|
| | G | G | A | T | C | A | C | A | G | G | C | G | A | A | A | C |
| 1st cycle | X | T | A | | | | | | | | | | | | | |
| 2nd cycle | X | T | A | X | T | G | | | | | | | | | | |
| 3rd cycle | X | T | A | X | T | G-X-T | C | | | | | | | | | |
| 4th cycle | X | T | A | X | T | G-X-T | C | | X | | | | T | T | | |
| Sequence | X | T | A | X | T | G-X-T | C | | X | | | | T | T | | |

TABLE 3

| | | | | | | | | | | | | | | | | | |
|---|---|---|---|---|---|---|---|---|---|---|---|---|---|---|---|---|---|
| | | | | | Target nucleic acid | | | | | | | | | | | | |
| | G | G | A | T | C | A | C | A | G | G | C | G | G | A | A | A | C |
| 1st cycle | X | X | X | X | G | | | | | | | | | | | | |
| 2nd cycle | X | X | X | X | G | X | X | X | X | C | | | | | | | |
| 3rd cycle | X | X | X | X | G | X | X | X | X | C | X | X | X | X | T | | |
| Sequence | X | X | X | X | G | X | X | X | X | C | X | X | X | X | T | | |

Example 4

Series of Limited Read Extension Steps; Limited Dark Extension Steps with Three Nucleotide Monomers Only This example illustrates a method of sequencing that comprises a cycle including: (1) a limited dark extension step with three nucleotide monomers only, and (2) a series of four limited read extension steps, each read step with one labeled nucleotide monomer.

A single limited dark extension step is performed. The limited dark extension sequencing reagent (first sequencing reagent) including the nucleotide monomers, A, C, G, is delivered to a target nucleic acid in the presence of DNA polymerase. A polynucleotide strand complementary to the target nucleic acid may incorporate the A, C, and G nucleotide monomers. The first sequencing reagent is removed.

In a first limited read extension step, the limited read extension reagent (second sequencing reagent) including the labeled nucleotide monomer 'A' is delivered to a target nucleic acid in the presence of DNA polymerase. The incorporation of 'A' is determined. The second sequencing reagent is removed. The limited read extension step is repeated for each nucleotide, substituting 'A' with either 'C', 'G' or 'T' in turn. The limited dark extension step and limited read extension steps are repeated.

Table 4 shows an example target nucleic acid (SEQ ID NO:01) and the sequence information that can be derived from three cycles, wherein each cycle comprises a single limited dark extension step followed by a series of four limited read extension steps, and wherein a first sequencing reagent includes C, G and T, and a series of second sequencing reagents are added in the order A, C, G, and T. As will be appreciated, the sequence representation obtained can be different where a different order of second sequencing reagents is used. "X" represents an unknown number and/or type of incorporated nucleotides.

TABLE 4

| | | | | | | | | | | | | | | | | | |
|---|---|---|---|---|---|---|---|---|---|---|---|---|---|---|---|---|---|
| | | | | | Target nucleic acid | | | | | | | | | | | | |
| | G | G | A | T | C | A | C | A | G | T | C | C | G | T | A | A | A |
| 1st cycle | X | X | X | A | G | T | | | | | | | | | | | |
| 2nd cycle | X | X | X | A | G | T | X | X | X | A | G | G | | | | | |
| 3rd cycle | X | X | X | A | G | T | X | X | X | A | G | G | X | A | T | T | T |
| Sequence | X | X | X | A | G | T | X | X | X | A | G | G | X | A | T | T | T |

Example 5

Series of Limited Read Extension Steps; Limited Dark Extension Steps with Nucleotide Monomer with Reversibly Terminating Moiety This example illustrates a method of sequencing that comprises a cycle including: (1) a limited dark extension step with a nucleotide monomer comprising a reversible terminating moiety, and (2) four series of limited read extension steps, each read step with one labeled nucleotide monomer.

A single limited dark extension step is performed. The limited dark extension sequencing reagent (first sequencing reagent) including the nucleotide monomers, $A^T$, C, G, and T is delivered to a target nucleic acid in the presence of DNA polymerase (superscript "T" represents a reversibly terminating moiety). A polynucleotide strand complementary to the target nucleic acid may incorporate the $A^T$, C, G, and T nucleotide monomers. The first sequencing reagent is removed. The reversible terminating moiety of an incorporated nucleotide is removed.

In a first limited read extension step, the limited read extension reagent (second sequencing reagent) including the labeled nucleotide monomer 'A' is delivered to a target nucleic acid in the presence of DNA polymerase. The incorporation of 'A' is determined. The second sequencing reagent is removed. The limited read extension step is repeated for each nucleotide, substituting 'A' with either 'C', 'G' or 'T' in turn. The limited dark extension step and limited read extension steps are repeated.

Table 5 shows an example target nucleic acid (SEQ ID NO:01) and the sequence information that can be derived from three cycles, wherein each cycle comprises a single limited dark extension step followed by a series of four limited read extension steps, where a first sequencing reagent includes $A^T$, C, and G, and T, and a series of second sequencing reagents are added in the order A, C, G, and T. "X" represents an unknown number and/or type of incorporated nucleotides.

TABLE 5

| | | | | | | | Target nucleic acid | | | | | | | | | | |
|---|---|---|---|---|---|---|---|---|---|---|---|---|---|---|---|---|---|
| | G | G | A | T | C | A | C | A | G | T | C | C | G | T | A | A | A |
| 1st cycle | X | | A | G | T | | | | | | | | | | | | |
| 2nd cycle | X | | A | G | T | | X | | A | G | G | | | | | | |
| 3rd cycle | X | | A | G | T | | X | | A | G | G | X | A | T | T | T | |
| Sequence | X | | A | G | T | | X | | A | G | G | X | A | T | T | T | |

Example 6

Limited Dark Extension Step Repeated

This example illustrates a method of sequencing that includes a cycle including (1) a series of two limited dark extension steps with three nucleotide monomers only; and (2) a series of two limited read extension steps with nucleotide monomers comprising labels and reversibly terminating moieties.

A first limited dark extension step is performed. The first limited dark extension sequencing reagent including the nucleotide monomers, A, C, G, is delivered to a target nucleic acid in the presence of DNA polymerase. A polynucleotide strand complementary to the target nucleic acid may incorporate the A, C, and G nucleotide monomers. The limited dark extension sequencing reagent is removed. The limited dark extension step is repeated with the second limited dark extension reagent containing A, C, and T.

Two limited read steps are performed. The limited read extension sequencing reagent (second sequencing reagent) including the nucleotide monomers, $A^T$, $C^T$, $G^T$, $T^T$ is delivered to the target nucleic acid in the presence of DNA polymerase (superscript "T" represents a reversibly terminating moiety). The limited read extension sequencing reagent is removed. The incorporation of a particular type of nucleotide monomer into the polynucleotide complementary to the target nucleic acid is detected. The reversibly terminating moiety of the incorporated nucleotide is removed. The limited read extension step is repeated. The limited dark extension step and limited read extension steps are repeated.

Table 6 shows an example target nucleic acid (SEQ ID NO:01) and sequence information that can be derived from three cycles, wherein each cycle comprises two limited dark extension steps followed by two limited read extension steps, and wherein a first limited dark extension step reagent includes A, C, and G, and a second limited dark extension step reagent includes A, C, and T. "X" represents an unknown number and/or type of incorporated nucleotides.

acids and a reference to map obtained sequences. Simulated sequencing runs included alternate intervals of sequencing by synthesis (SBS) cycles and limited dark extension steps. The generic setup of the methodology was as follows:

$X_1$ cycles SBS→$Y_1$ cycles of dark extension→$X_2$ cycles of SBS→$Y_2$ cycles of dark extension . . . $X_n$ cycles SBS→$Y_n$ cycles of dark extension In the above-described methodology $X_n$ cycles refers to extension steps and $Y_n$ cycles of dark extension refers to the number of extensions performed using a nucleotide monomer mixture comprising A, G, C and $T^T$. A total of five intervals of SBS cycles were performed ($X_5$). In the limited dark steps, simulated sequence extension terminated at 'T.' Sequencing was simulated as error-free and a threshold of at least 100 SBS cycles was used. In a sequencing run, the first interval ($X_1$) included twenty-five SBS cycles to provide an anchor for subsequent alignment to the *Arabidopsis* genome.

Alignment of Sequences Obtained in Simulated Sequencing Runs

A first simulated sequencing run was performed where each SBS interval included twenty-five cycles, and each limited dark extension step interval included five cycles. The sequences obtained were aligned to the *Arabidopsis* genome. FIG. 1A shows the percentage of sequences that mapped to specific locations in the *Arabidopsis* genome with no ambiguity, where sequences were obtained from: (1) the first interval of twenty-five SBS cycles (anchor only); or (2) all intervals of SBS cycles (all SBS).

Figure 1B:
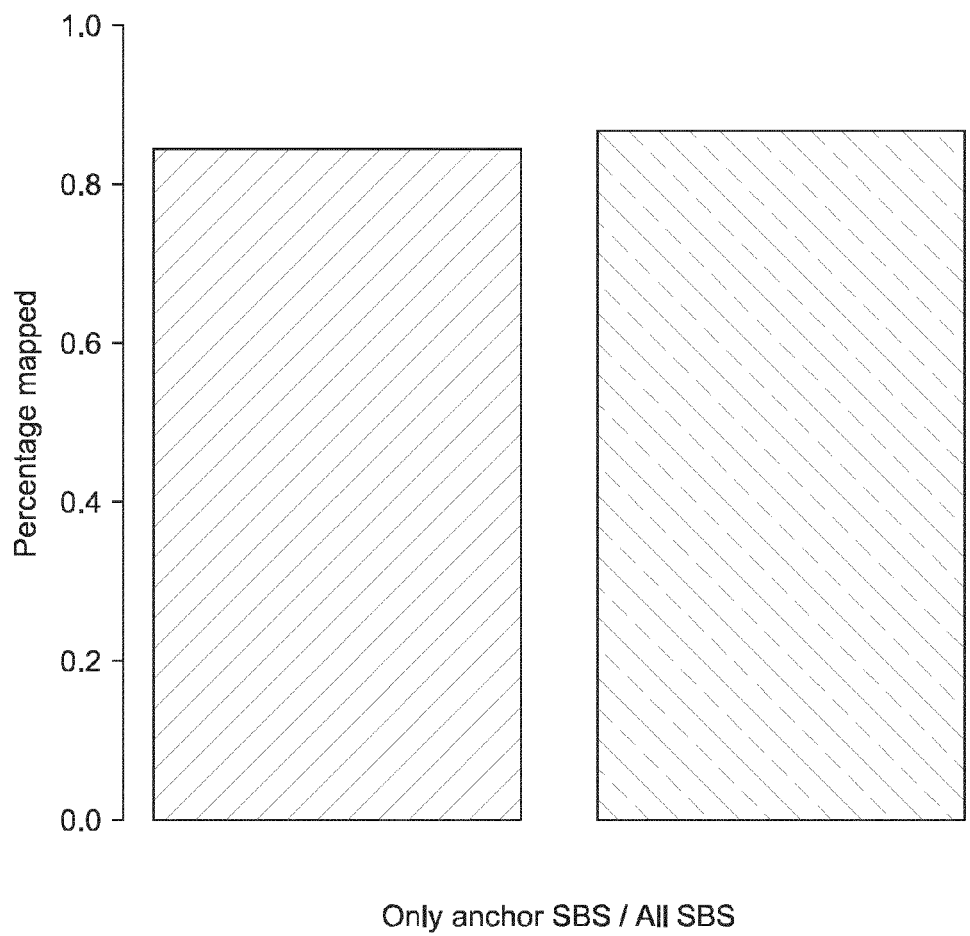
FIG. 1B shows the percentage of sequences that mapped to specific locations in the *Arabidopsis* genome with no ambiguity, where sequences were obtained from: (1) the first interval of twenty-five SBS cycles (anchor only); or (2) all intervals of SBS cycles. Y-axis shows 100% as 1.0.

A second simulated sequencing run was performed where the first SBS interval included twenty-five cycles, each subsequent SBS interval included five cycles, and each limited dark step interval included twenty cycles. The sequences obtained were aligned to the *Arabidopsis* genome. FIG. 1B shows the percentage of sequences that mapped to specific locations in the *Arabidopsis* genome with no ambiguity, where sequences were obtained from: (1) the first interval of twenty-five SBS cycles (anchor only); or (2) all intervals of SBS cycles. In this second simulation, the percentage of sequences that align to specific locations is still similar to the

TABLE 6

| | | | | | | | | | | | Target nucleic acid | | | | | | | | | | | | | |
|---|---|---|---|---|---|---|---|---|---|---|---|---|---|---|---|---|---|---|---|---|---|---|---|---|
| | G | G | T | A | C | G | T | A | T | C | A | C | C | G | G | C | G | G | A | T | A | G | C | A |
| 1st cycle | X | | | | G | C | | | | | | | | | | | | | | | | | | |
| 2nd cycle | X | | | | G | C | | X | | | G | T | | | | | | | | | | | | |
| 3rd cycle | X | | | | G | C | | X | | | G | T | | | | | X | | | | | | G | T |
| Sequence | X | | | | G | C | | X | | | G | T | | | | | X | | | | | | G | T |

Example 7

Computer-Simulations

Computer simulations were performed using the *Arabidopsis* genome (115,409,949 bp) as a source for target nucleic results shown in FIG. 1A, however, the sequence representations that are obtained are longer than the first simulation.

Extension of Polynucleotides During Simulated Limited Dark Extension Steps

Figure 2A:
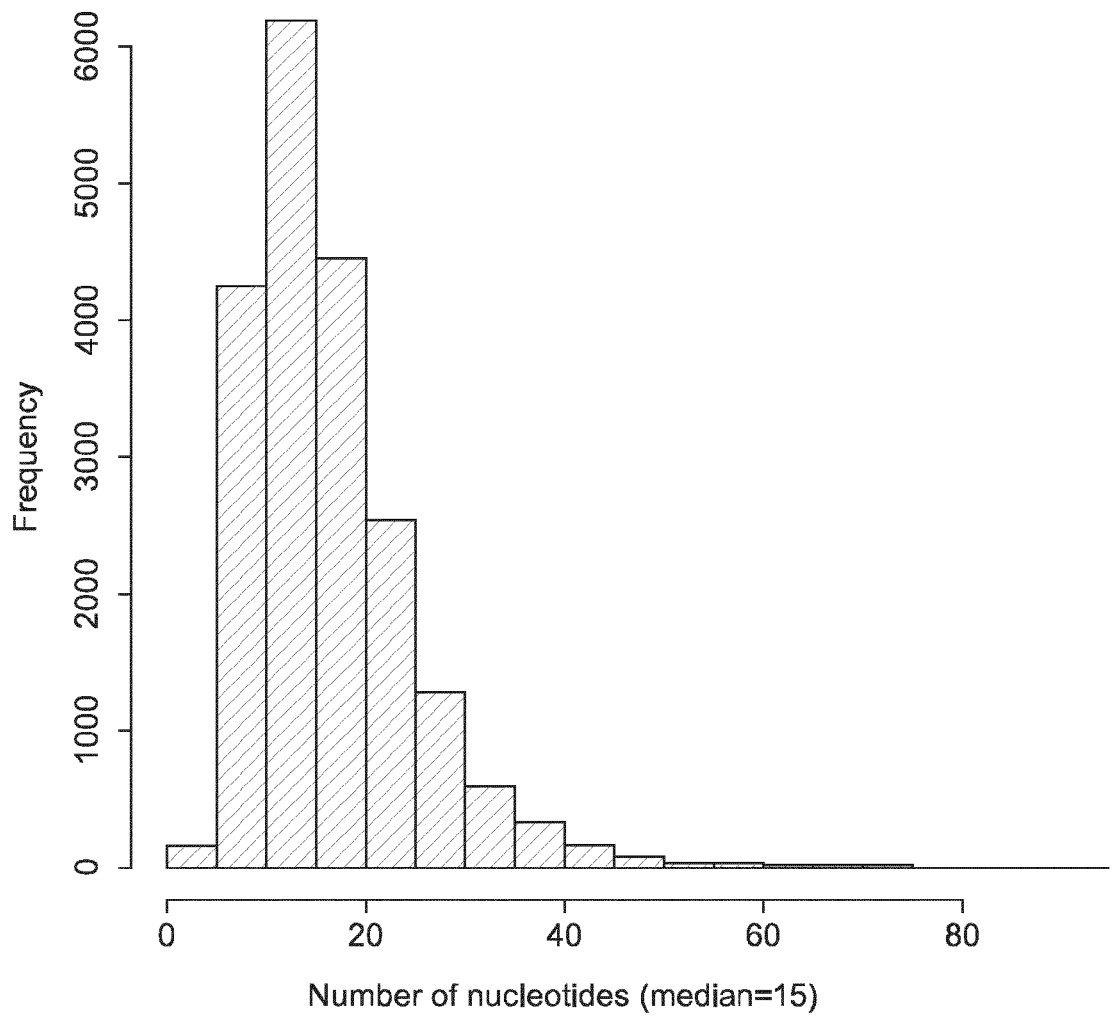
FIG. 2A shows a graph of the number of nucleotides extended during simulated limited dark extension steps of 5 cycles.
Figure 2B:
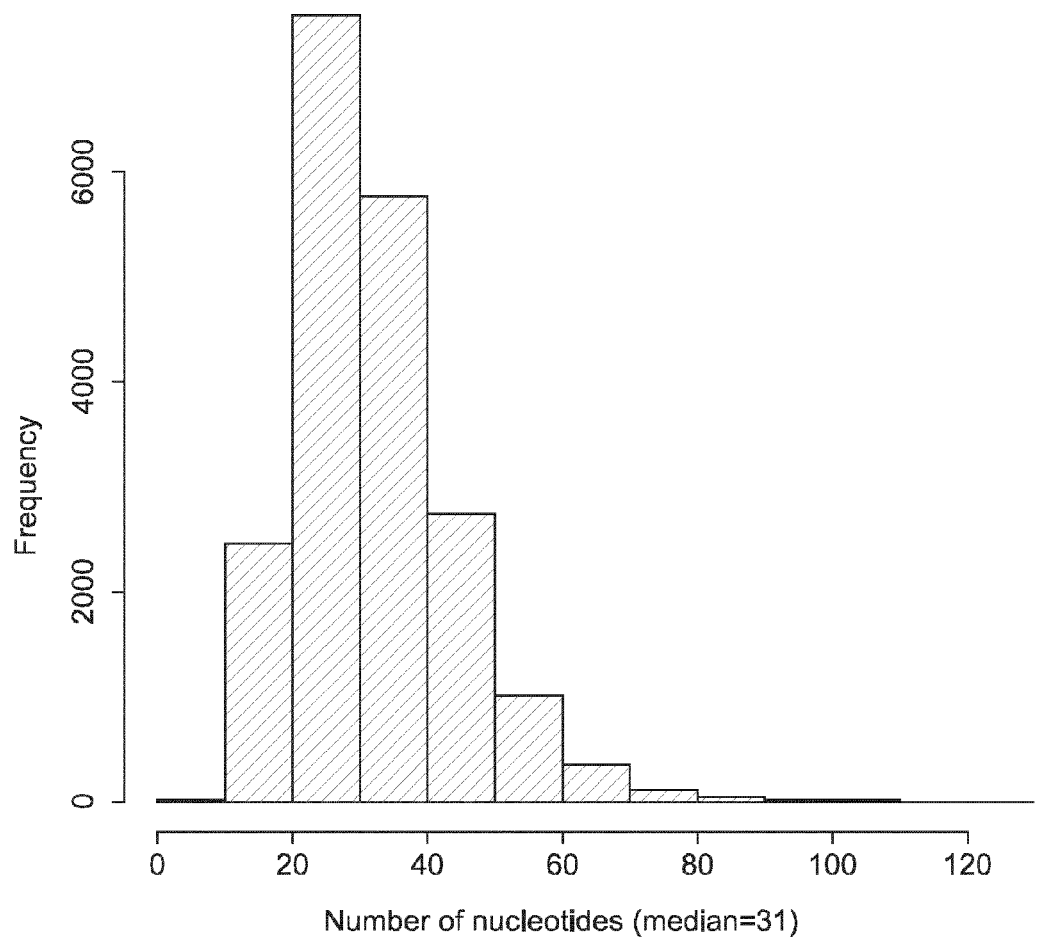
FIG. 2B shows a graph of the number of nucleotides extended during simulated limited dark extension steps of 10 cycles.
Figure 2C:
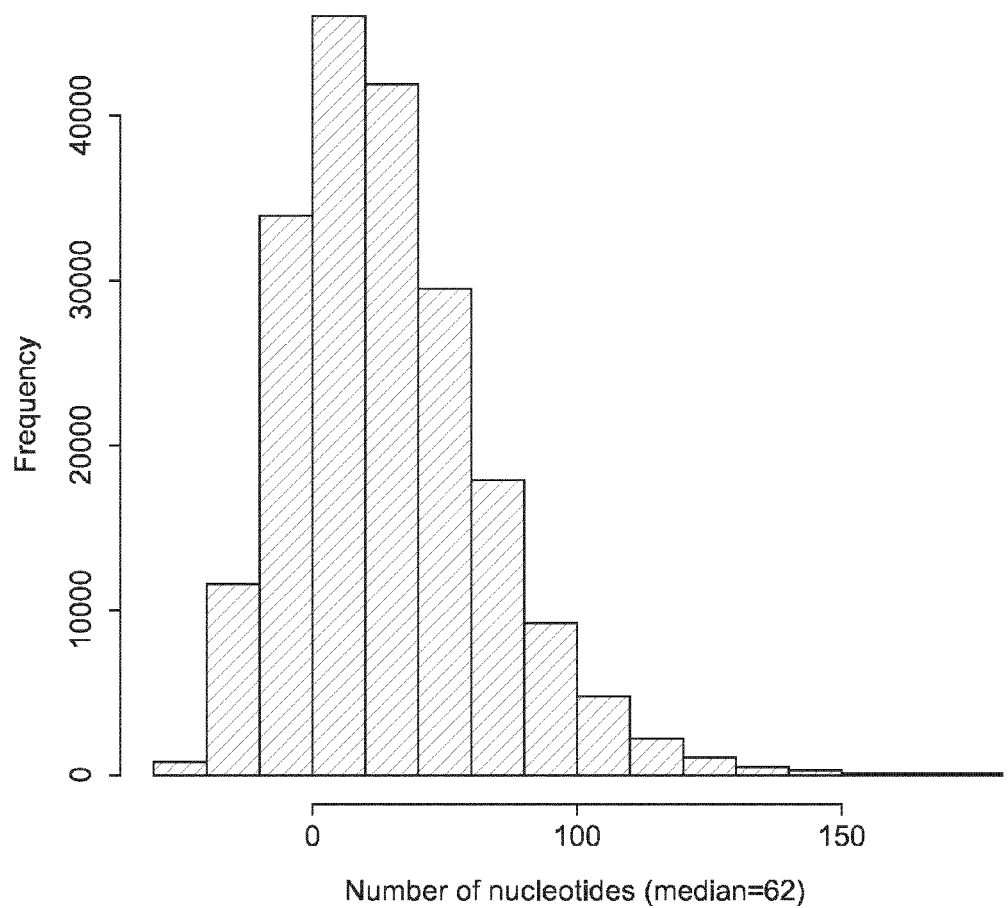
FIG. 2C shows a graph of the number of nucleotides extended during simulated limited dark extension steps of 20 cycles.

Simulated sequencing runs were performed that included limited dark extension steps of 5, 10, or 20 cycles. The number of nucleotides extended in each interval of limited dark extension steps was recorded. FIGS. 2A, 2B, and 2C show the number of nucleotides extended during intervals where the number of limited dark extension step cycles was 5, 10, or, 20, respectively. For simulated sequencing runs that included 5, 10, or 20 limited dark extension step cycles in an interval, the median number of polynucleotides extended were 15, 31, and 62, respectively.

Total Extension of Polynucleotides in Simulated Sequencing Runs

Figure 3A:
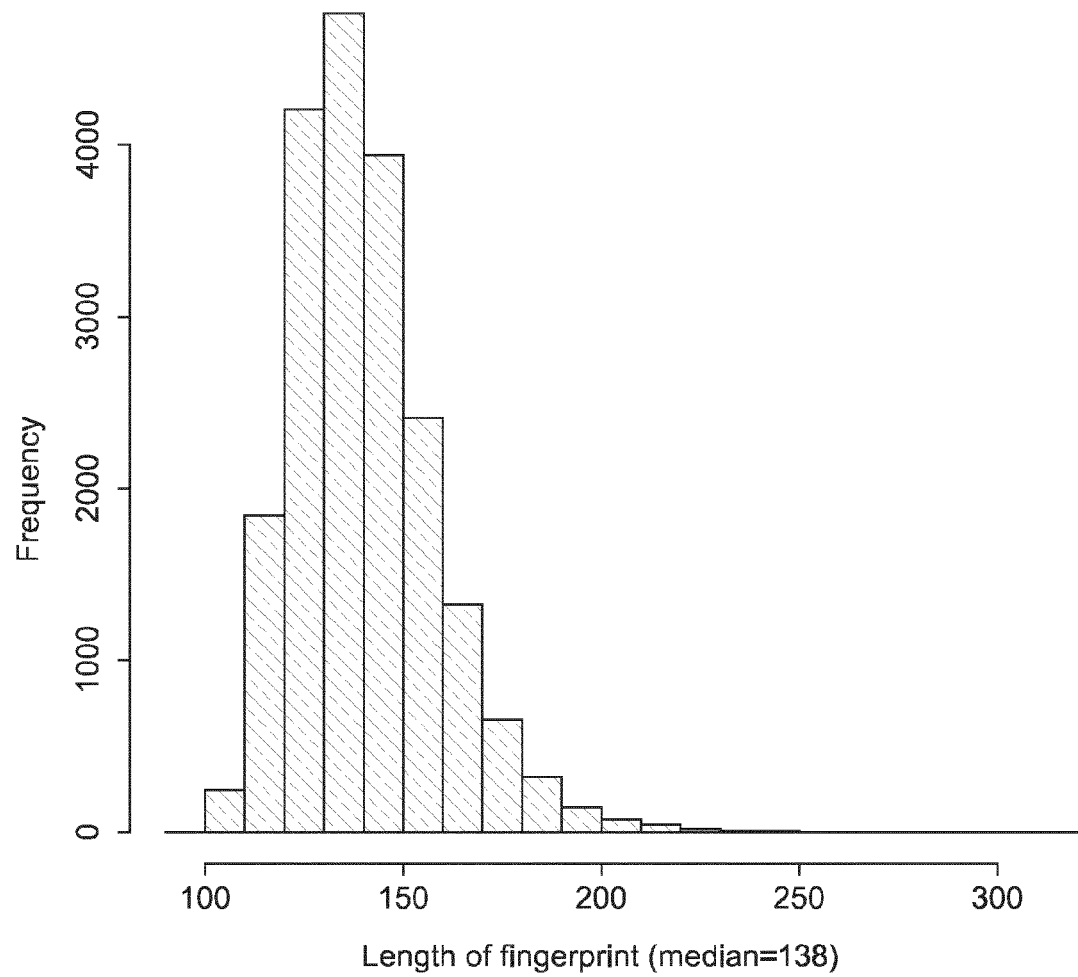
FIG. 3A show a graph of the total number of nucleotides extended in simulated sequencing runs that include intervals of 5 cycles of limited dark extension step.
Figure 3B:
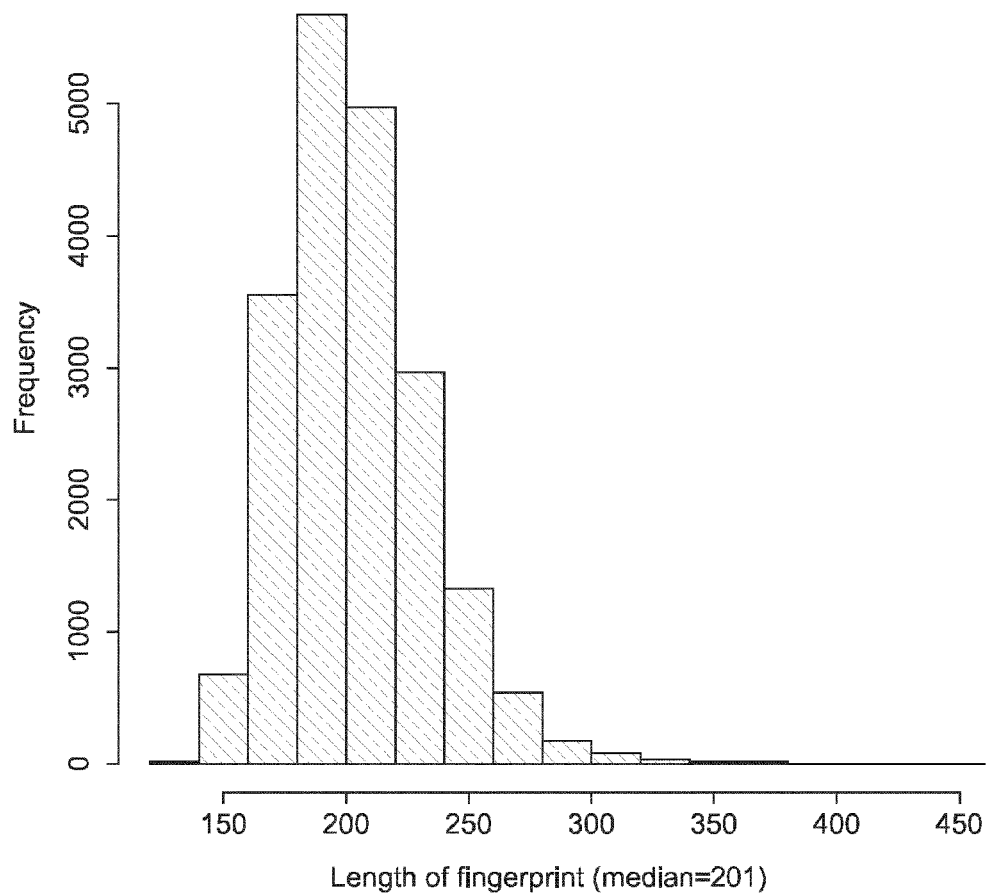
FIG. 3B show a graph of the total number of nucleotides extended in simulated sequencing runs that include intervals of 10 cycles of limited dark extension step.
Figure 3C:
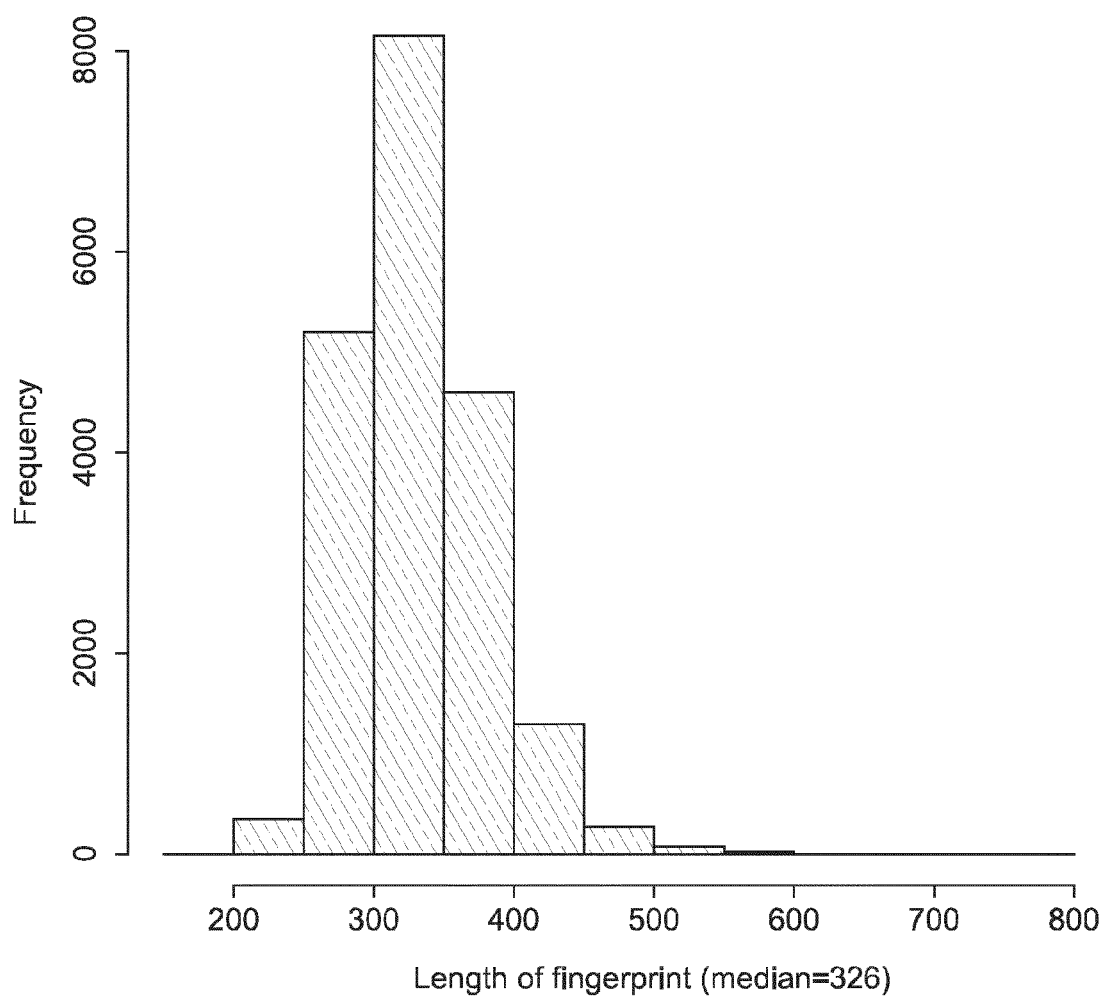
FIG. 3C show a graph of the total number of nucleotides extended in simulated sequencing runs that include intervals of 20 cycles of limited dark extension step.

Simulated sequencing runs were performed where each SBS interval included twenty-five cycles, and each limited dark extension step interval included 5, 10, or cycles. The total number of nucleotides extended in each sequencing run was recorded. FIGS. 3A, 3B, and 3C show the total number of nucleotides extended where the number of limited dark extension step cycles in each run was 5, 10, or, 20, respectively. For simulated sequencing runs that included 5, 10, or 20 limited dark extension step cycles in an interval, the median number of polynucleotides extended were 138, 201, and 326, respectively.

Example 8

High Resolution Fingerprints from Low Resolution Sequence Representations

A high resolution sequence representation is obtained by combining a series of low resolution sequence representations obtained from four sequencing runs on a target nucleic acid. Each sequencing run includes a series of four limited dark extension steps and a limited read extension step, where each limited dark extension step includes a different limited dark extension step reagent. For example, reagent 1 (R1)=A,C,G; reagent 2 (R2)=A,C,T; reagent 3 (R3)=A,G,T; and reagent 4 (R4)=T,C,G. The sequential order in which the limited dark extension steps are performed is different for each sequencing run.

In a first sequencing run, four limited dark extension steps are performed using dark extension step reagents in the order R1-R2-R3-R4, followed by a limited read extension step. The four extension limited dark extension steps and limited read extension step are repeated and a first low resolution sequence representation is obtained.

In a second sequencing run, four limited dark extension steps are performed using dark extension step reagents in the order R2-R3-R4-R1, followed by a limited read extension step. The four extension limited dark extension steps and limited read extension step are repeated and a second low resolution sequence representation is obtained.

In a third sequencing run, four limited dark extension steps are performed using dark extension step reagents in the order R3-R4-R1-R2, followed by a limited read extension step. The four extension limited dark extension steps and limited read extension step are repeated and a third low resolution sequence representation is obtained.

In a fourth sequencing run, four limited dark extension steps are performed using dark extension step reagents in the order R4-R1-R2-R3, followed by a limited read extension step. The four extension limited dark extension steps and limited read extension step are repeated and a fourth low resolution sequence representation is obtained.

The four low resolution sequence representations are combined to produce a higher resolution sequence representation of the target nucleic acid.

It will be appreciated that a high resolution representation can also be produced by performing less than four sequencing runs. For example, a complete high resolution sequencing representation can be produced by performing only the first three sequencing runs indicated above. In such cases, the sequencing error rate may be higher than if four sequencing runs had been performed.

Example 9

Fast Forward Sequencing Using Three Nucleotide Additions

A library of PhiX174 (PhiX) ~300 bp genome fragments was used as a source for target nucleic acids. A sequencing run included a first round of fourteen sequencing by synthesis (SBS) cycles, eight rounds of dark extension, and a second round of fourteen SBS cycles. In each round of dark extension, a series of four limited dark extension steps were performed, where each limited dark extension step included a different limited dark extension step reagent. For example, reagent 1 (R1)=A,C,G; reagent 2 (R2)=A,C,T; reagent 3 (R3)=A,G,T; and reagent 4 (R4)=T,C,G. Accordingly, each round of dark extension included the serial addition and removal of R1, R2, R3, and R4.

Figure 4:
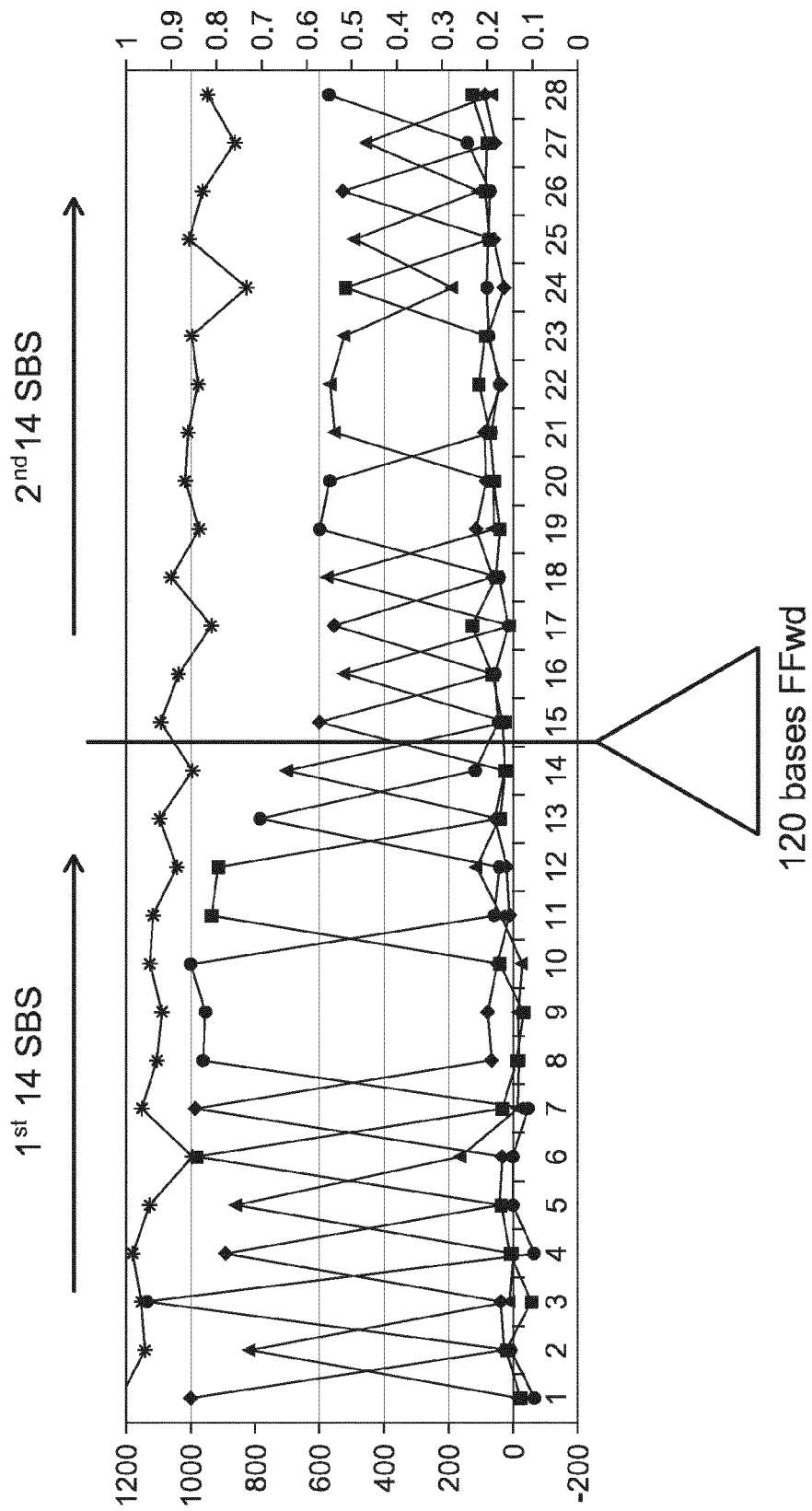
FIG. 4 shows a graph of nucleotide-calls in a sequence run. Left y-axis corresponds to signal intensity for each nucleotide-call, the right y-axis corresponds to the chastity of the nucleotide-call. Chastity relates to the relative intensity of a peak nucleotide-call compared to the intensity of other nucleotide-calls. Chastity is represented in the uppermost line (*). 'A' nucleotide-call (♦); 'C' nucleotide-call (■); 'G' nucleotide-call (•); and 'T' nucleotide-call (▲). Obtained sequences from the first and second rounds of SBS cycles mapped to sequences on the target nucleic acid interspersed by 120 nucleotides.
Figure 5:
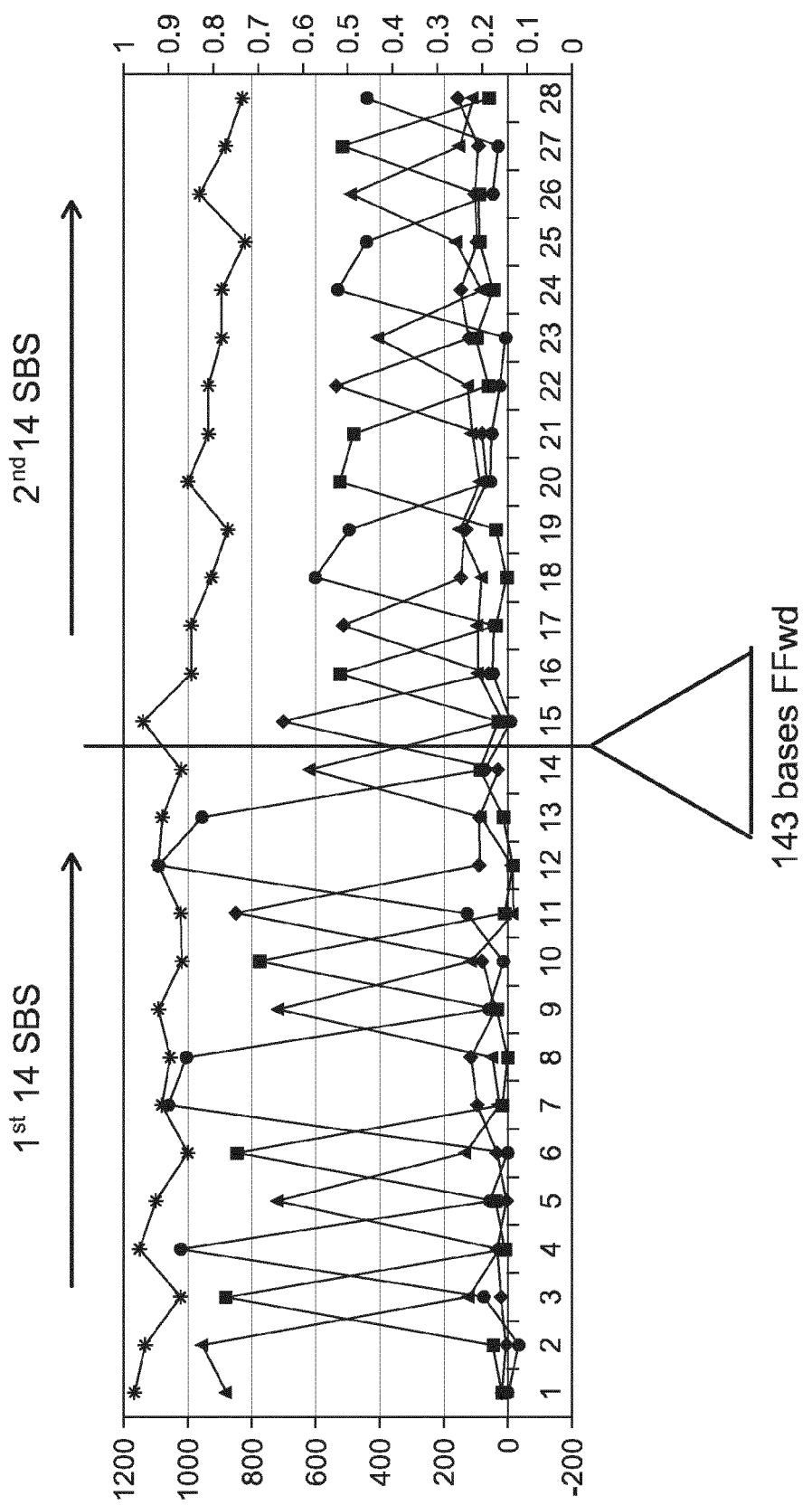
FIG. 5 shows a graph of nucleotide-calls in a sequence run. Left y-axis corresponds to signal intensity for each nucleotide-call, the right y-axis corresponds to the chastity of the nucleotide-call. Chastity relates to the relative intensity of a peak nucleotide-call compared to the intensity of other nucleotide-calls. Chastity is represented in the uppermost line (*). 'A' nucleotide-call (♦); 'C' nucleotide-call (■); 'G' nucleotide-call (•); and 'T' nucleotide-call (▲). Obtained sequences from the first and second rounds of SBS cycles mapped to sequences on the target nucleic acid interspersed by 143 nucleotides.

The sequences produced by the above-described method were mapped to the nucleotide sequence of the PhiX library. In an example sequence representation, sequences obtained in the first and second rounds of SBS cycles mapped to sequences of the PhiX library interspersed by 120 consecutive dark extension nucleotides (FIG. 4). In another example sequence representation, sequences obtained in the first and second rounds of SBS cycles mapped to sequences of the PhiX library interspersed by 143 consecutive dark extension nucleotides (FIG. 5).

In a series of sequencing runs, sequences obtain in first and second SBS cycles mapped to sequences of the PhiX library interspersed by an average of 143 consecutive nucleotides.

Analysis of Sequencing Data

Sequencing data was analyzed by mapping sequence representations from SBS cycles for each sequencing run to the PhiX genome. Analysis of the results produced performance metrics that included: (1) accuracy for combined SBS and dark extension performance (% cluster passing filter (PF)); (2) efficiency of dark extension steps terminating at predicted termination positions (% perfect hits of total hits); and (3) accuracy of the system (% perfect hits of clusters PF).

Predicted Lengths of Consecutive Nucleotides Advanced in Dark Extension

Figure 6:
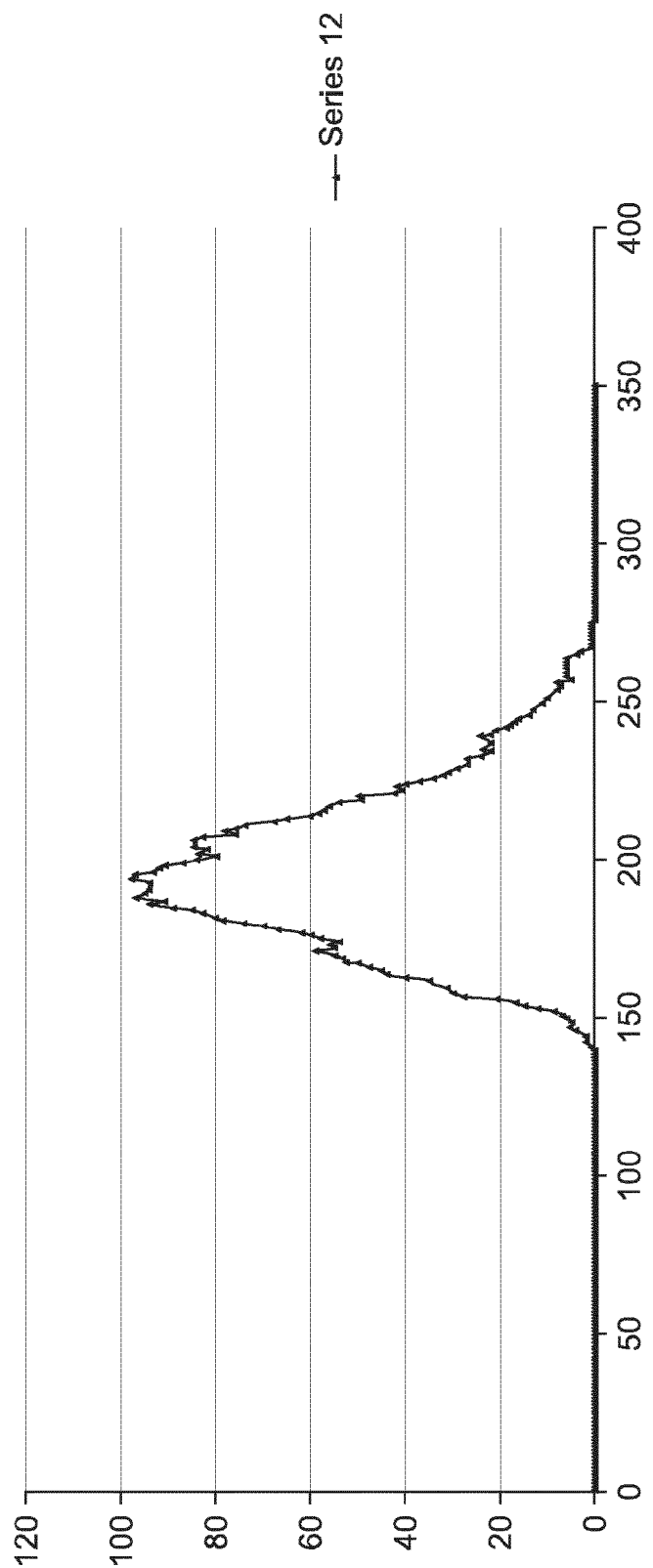
FIG. 6 shows a graph of the predicted number of consecutive nucleotides advanced in twelve rounds of dark extension (x-axis) vs. number of in silico sequencing runs (y-axis). Chastity is represented in the uppermost line (*). 'A' nucleotide-call (♦); 'C' nucleotide-call (■); 'G' nucleotide-call (•); and 'T' nucleotide-call (▲).

In an in silico experiment, the number of consecutive nucleotides advanced in a sequencing run comprising twelve rounds of dark extension was predicted using the PhiX genome. Each round of dark extension was assumed to include a series of four limited dark extension steps, where each limited dark extension step included a different limited dark extension step reagent. The number of consecutive nucleotides advanced in a round of dark extension was calculated from each nucleotide position in the PhiX genome. In other words, a set of in silico sequencing runs was performed, where each sequencing run started from a different nucleotide of the PhiX genome. FIG. 6 shows a graph of the predicted number of consecutive nucleotides advanced in twelve rounds of dark extension (x-axis) vs. number of in silico sequencing runs (y-axis).

Example 10

Barcode Sequencing

The following example illustrates an application for identifying specific organisms. A mock community of target nucleic acids was generated. The mock community comprised a mixture of nucleic acids amplified from the V3 region of the 16S rRNA gene for various microorganisms. Table 7 shows nucleotide sequences of the V3 region of the 16S rRNA gene sequence for various organisms.

Sequence representations for target sequences from Table 7 were predicted in silico for a sequencing run that include dark extension. The sequencing run included six cycles, each cycle including: six limited read steps, followed by a round of dark extension. In each round of dark extension, a series of four limited dark extension steps were performed, where each limited dark extension step included a different limited dark extension step reagent, in which reagent 1 (R1)=A,C,G; reagent 2 (R2)=A,C,T; reagent 3 (R3)=CGT; and reagent 4 (R4)=AGT. The sequencing run is summarized as follows: $1^{st}$ SBS cycle (6 limited read steps)→$1^{st}$ dark extension round (4 limited extension steps)→$2^{nd}$ SBS cycle (6 limited read steps)→$2^{nd}$ dark extension round (4 limited extension steps)→$3^{rd}$ SBS cycle (6 limited read steps)→$3^{rd}$ dark extension round (4 limited extension steps)→$4^{th}$ SBS cycle (6 limited read steps)→$4^{th}$ dark extension round (4 limited extension steps)→$5^{th}$ SBS cycle (6 limited read steps)→$5^{th}$ dark extension round (4 limited extension steps)→$6^{th}$ SBS cycle (6 limited read steps)→$6^{th}$ dark extension round (4 limited extension steps).

It will be appreciated that in some embodiments, the final dark extension is not performed. In other embodiments, the first sequencing step may be a dark extension rather than a read step.

The predicted sequence representations are shown in Table 8. In this embodiment, the sequence representations are barcodes that were produced by concatenating the sequence information obtained from each of the read steps. It will be appreciated that other barcode representations could be used, such as those described previously herein.

TABLE 7

| Organism | Target Sequence (SEQ ID NO.) |
|---|---|
| Acinetobacter baumanii | (SEQ ID NO.: 02)<br>TGGGGAATATTGGACAATGGGGGGAACCCTGATCCAGCCATGCCGCGT<br>GTGTGAAGAAGGCCTTATGGTTGTAAAGCACTTTAAGCGAGGAGGAGGC<br>TTACCTGGTTAATACCCAGGATAAGTGGACGTTACTCGCAGAATAAGCAC<br>CGGCTAACTCT |
| Actinomyces odontolyticus | (SEQ ID NO.: 03)<br>TGGGGAATATTGCACAATGGGCGCAAGCCTGATGCAGCGACGCCGCGT<br>GAGGGATGGAGGCCTTCGGGTTGTGAACCTCTTTCGCCAGTGAAGCAG<br>GCCCGCCTCTTTTGTGGGTGGGTTGACGGTAGCTGGATAAGAAGCGCC<br>GGCTAACTACGTGCCAGCAGCCGCGGTAA |
| Baciluus cereus | (SEQ ID NO.: 04)<br>TAGGGAATCTTCCGCAATGGACGAAAGTCTGACGGAGCAACGCCGCGTG<br>AGTGATGAAGGCTTTCGGGTCGTAAAACTCTGTTGTTAGGGAAGAACAA<br>GTGCTAGTTGAATAAGCTGGCACCTTGACGGTACCTAACCAGAAAGCCA<br>CGGCTAACTAC |
| Bacteroides vulgatus 1 | (SEQ ID NO.: 05)<br>TGAGGAATATTGGTCAATGGGCGAGAGCCTGAACCAGCCAAGTAGCGTG<br>AAGGATGACTGCCCTATGGGTTGTAAACTTCTTTTATAAAGGAATAAAGT<br>CGGGTATGCATACCCGTTTGCATGTACTTTATGAATAAGGATCGGCTAAC<br>TCC |
| Bacteroides vulgatus 2 | (SEQ ID NO.: 06)<br>TGAGGAATATTGGTCAATGGGCGCAGGCCTGAACCAGCCAAGTAGCGTG<br>AAGGATGACTGCCCTATGGGTTGTAAACTTCTTTTATAAAGGAATAAAGT<br>CGGGTATGGATACCCGTTTGCATGTACTTTATGAATAAGGATCGGCTAAC<br>TCC |
| Bacteroides vulgatus 3 | (SEQ ID NO.: 07)<br>TGAGGAATATTGGTCAATGGGCGAGAGCCTGAACCAGCCAAGTAGCGTG<br>AAGGATGACTGCCCTATGGGTGTAAACTTCTTTTATAAAGGAATAAAGT<br>CGGGTATGGATACCCGTTTGCATGTACTTTATGAATAAGGATCGGCTAAC<br>TCC |
| Clostridium biijerincki | (SEQ ID NO.: 08)<br>TGGGGAATATTGCACAATGGGGGAAACCCTGATGCAGCAACGCCGCGT<br>GAGTGATGACGGTCTTCGGATTGTAAAGCTCTGTCTTCAGGGACGATAAT<br>GACGGTACCTGAGGAGGAAGCCACGGCTAACTAC |
| Deinococcus radiourans | (SEQ ID NO.: 09)<br>TTAGGAATCTTCCACAATGGGCGCAAGCCTGATGGAGCGACGCCGCGTG<br>AGGGATGAAGGTTTTCGGATCGTAAACCTCTGAATCTGGGACGAAAGAG<br>CCTTAGGGCAGATGACGGTACCAGAGTAATAGCACCGGCTAACTCC |
| Escherichia coli | (SEQ ID NO.: 10)<br>TGGGGAATATTGCACAATGGGCGCAAGCCTGATGCAGCCATGCCGCGT<br>GTATGAAGAAGGCCTTCGGGTTGTAAAGTACTTTCAGCGGGGAGGAAGG<br>GAGTAAAGTTAATACCTTTGCTCATTGACGTTACCCGCAGAAGAAGCACC<br>GGCTAACTCC |
| Enterococcus faecalis | (SEQ ID NO.: 11)<br>TAGGGAATCTTCGGCAATGGACGAAAGTCTGACCGAGCAACGCCGCGTG<br>AGTGAAGAAGGTTTTCGGATCGTAAAACTCTGTTGTTAGAGAAGAACAAG |

TABLE 7-continued

| Organism | Target Sequence (SEQ ID NO.) |
|---|---|
| | GACGTTAGTAACTGAACGTCCCCTGACGGTATCTAACCAGAAAGCCACG<br>GCTAACTAC |
| Helicobacter pylori | (SEQ ID NO.: 12)<br>TAGGGAATATTGCTCAATGGGGGAAACCCTGAAGCAGCAACGCCGCGTG<br>GAGGATGAAGGTTTTAGGATTGTAAACTCCTTTTGTTAGAGAAGATAATG<br>ACTAACGAATAAGCACCGGCTAACTCCGTGCCAGCAGCCGCGGTAA |
| Lactobacillus gasseri | (SEQ ID NO.: 13)<br>TAGGGAATCTTCCACAATGGACGCAAGTCTGATGGAGCAACGCCGCGTG<br>AGTGAAGAAGGGTTTCGGCTCGTAAAGCTCTGTTGGTAGTGAAGAAAGA<br>TAGAGGTAGTAACTGGCCTTTATTTGACGGTAATTACTTAGAAAGTCACG<br>GCTAACTAC |
| Listeria monocytogenes | (SEQ ID NO.: 14)<br>TAGGGAATCTTCCGCAATGGACGAAAGTCTGACGGAGCAACGCCGCGTG<br>TATGAAGAAGGTTTTCGGATCGTAAAGTACTGTTGTTAGAGAAGAACAAG<br>GATAAGAGTAACTGCTTGTCCCTTGACGGTATCTAACCAGAAAGCCACG<br>GCTAACTAC |
| Methanobrevibacter smithii 1 | (SEQ ID NO.: 15)<br>GCGCGAAACCTCCGCAATGTGAGAAATCGCGACGGGGGGGATCCCAAG<br>TGCCATTCTTAACGGGATGGCTTTTCATTAGTGTAAAGAGCTTTTGGAATA<br>AGAGCTGGGCAAGACCGGTGCCAGCCGCCGCGGTAAGTGCCAGCCGC<br>CGCGGTAA |
| Methanobrevibacter smithii 2 | (SEQ ID NO.: 16)<br>GCGCGAAACCTCCGCAATGTGAGAAATCGCGACGGGGGATCCCAAGT<br>GCCATTCTTAACGGGATGGCTTTTCATTAGTGTAAAGAGCTTTTGGAATA<br>AGAGCTGGGCAAGACCGGTGCCAGCCGGCCGCGGTAAGTGCCAGCCG<br>CCGCGGTA |
| Neisseria meningitidis | (SEQ ID NO.: 17)<br>TGGGGAATTTTGGACAATGGGCGCAAGCCTGATCCAGCCATGCCGCGTG<br>TCTGAAGAAGGCCTTCGGGTTGTAAAGGACTTTTGTCAGGGAAGAAAAG<br>GCTGTTGCTAATATCAGCGGCTGATGACGGTACCTGAAGAATAAGCACC<br>GGCTAACTAC |
| Propionibacterium acnes | (SEQ ID NO.: 18)<br>TGGGGAATATTGCACAATGGGCGGAAGCCTGATGCAGCAACGCCGCGT<br>GCGGGATGACGGCCTTCGGGTTGTAAACCGCTTTCGCCTGTGACGAAGC<br>GTGAGTGACGGTAATGGGTAAAGAAGCACCGGCTAACTAC |
| Pseudomonas aeruginosa | (SEQ ID NO.: 19)<br>TGGGGAATATTGGACAATGGGCGAAAGCCTGATCCAGCCATGCCGCGTG<br>TGTGAAGAAGGTCTTCGGATTGTAAAGCACTTTAAGTTGGGAGGAAGGG<br>CAGTAAGTTAATACCTTGCTGTTTTGACGTTACCAACAGAATAAGCACCG<br>GCTAACTTC |
| Rhodobacter sphaeroides | (SEQ ID NO.: 20)<br>TGGGGAATCTTAGACAATGGGCGCAAGCCTGATCTAGCCATGCCGCGTG<br>ATCGATGAAGGCCTTAGGGTTGTAAAGATCTTTCAGGTGGGAAGATAATG<br>ACGGTACCACCAGAAGAAGCCCCGGCTAACTCC |
| Staphylococcus aureus | (SEQ ID NO.: 21)<br>TAGGGAATCTTCCGCAATGGGCGAAAGCCTGACGGAGCAACGCCGCGT<br>GAGTGATGAAGGTCTTCGGATCGTAAAACTCTGTTATTAGGGAAGAACAT<br>ATGTGTAAGTAACTGTGCACATCTTGACGGTACCTAATCAGAAAGCCACG<br>GCTAACTAC |
| Staphylococcus epidermidis 1 | (SEQ ID NO.: 22)<br>TAGGGAATCTTCCGCAATGGGCGAAAGCTTGACGGAGCAACGCCGCGT<br>GAGTGATGAAGGTCTTCGGATCGTAAAACTCTGTTATTAGGGAAGAACAA<br>ATGTGTAAGTAACTATGCACGTCTTGACGGTACCTAATCAGAAAGCCACG<br>GCTAACTAC |
| Staphylococcus epidermidis 2 | (SEQ ID NO.: 23)<br>TAGGGAATCTTCCGCAATGGGCGAAAGCCTGACGGAGCAACGCCGCGT<br>GAGTGATGAAGGTCTTCGGATCGTAAAACTCTGTTATTAGGGAAGAACAA<br>ATGTGTAAGTAACTATGCACGTCTTGACGGTACCTAATCAGAAAGCCACG<br>GCTAACTAC |
| Streptococcus agalactiae | (SEQ ID NO.: 24)<br>TAGGGAATCTTCGGCAATGGACGGAAGTCTGACCGAGCAACGCCGCGT<br>GAGTGAAGAAGGTTTTCGGATCGTAAAGCTCTGTTGTTAGAGAAGAACGT<br>TGGTAGGAGTGGAAAATCTACCAAGTGACGGTAACTAACCAGAAAGGGA<br>CGGCTAACTAC |

TABLE 7-continued

| Organism | Target Sequence (SEQ ID NO.) |
|---|---|
| Streptococcus mutans | (SEQ ID NO.: 25)<br>TAGGGAATCTTCGGCAATGGACGAAAGTCTGACCGAGCAACGCCGCGTG<br>AGTGAAGAAGGTTTTCGGATCGTAAAGCTCTGTTGTAAGTCAAGAACGTG<br>TGTGAGAGTGGAAAGTTCACACAGTGACGGTAGCTTACCAGAAAGGGAC<br>GGCTAACTAC |
| Streptococcus pneumoniae | (SEQ ID NO.: 26)<br>TAGGGAATCTTCGGCAATGGACGGAAGTCTGACCGAGCAACGCCGCGT<br>GAGTGAAGAAGGTTTTCGGATCGTAAAGCTCTGTTGTAAGAGAAGAACG<br>AGTGTGAGAGTGGAAAGTTCACACTGTGACGGTATCTTACCAGAAAGGG<br>ACGGCTAACTAC |

TABLE 8

| Organism | Predicted Sequence (SEQ ID NO) |
|---|---|
| Methano-brevibacter smithii | (SEQ ID NO.: 27)<br>GCGCGACGCGACCTTAACCTTTTGCTGGGCCAGCCG |
| Streptococcus mutans | (SEQ ID NO.: 28)<br>TAGGGACGAAAGCCGAGCCGGATCCAAGAACACACA |
| Enterococcus faecalis | (SEQ ID NO.: 29)<br>TAGGGACGAAAGCCGAGCCGGATCCAAGGACTGAAC |
| Listeria monocytogenes | (SEQ ID NO.: 30)<br>TAGGGACGAAAGCGGAGCCGGATCCTGTTGCAAGGA |
| Staphylococcus epidermidis | (SEQ ID NO.: 31)<br>TAGGGACGAAAGCGGAGCCTTCGGCTCTGTCAAATG |
| Staphylococcus aureus | (SEQ ID NO.: 32)<br>TAGGGACGAAAGCGGAGCCTTCGGCTCTGTCATATG |
| Baciluus cereus | (SEQ ID NO.: 33)<br>TAGGGACGAAAGCGGAGCCTTTCGCTCTGTCAAGTG |
| Lactobacillus gasseri | (SEQ ID NO.: 34)<br>TAGGGACGCAAGCAACGCCGGCTCCTGGCCCGGTAA |
| Streptococcus pneumoniae | (SEQ ID NO.: 35)<br>TAGGGACGGAAGCCGAGCCGGATCCGAGTGCACACT |
| Streptococcus agalactiae | (SEQ ID NO.: 36)<br>TAGGGACGGAAGCCGAGCCGGATCCGTTGGCTACCA |
| Helicobacter pylori | (SEQ ID NO.: 37)<br>TAGGGACCCTGACTCCTTCGGTATCACCGGCAGCCG |
| Bacteroides vulgatus | (SEQ ID NO.: 38)<br>TGAGGACGAGAGCCAGCCCTGCCCCTTCTTCGGGTA |
| Propionibacterium acnes | (SEQ ID NO.: 39)<br>TGGGGACAATGGCAGCAACGGCCTCCGCTTCGAAGC |
| Clostridium beijerincki | (SEQ ID NO.: 40)<br>TGGGGACAATGGCAGCAACGGTCTCTCTGTCGATAA |
| Escherichia coli | (SEQ ID NO.: 41)<br>TGGGGACAATGGCAGCCACCTTCGCTTTCACCTTTG |
| Actinomyces odontolyticus | (SEQ ID NO.: 42)<br>TGGGGACAATGGCAGCGACCTTCGCCTCTTCAAGCC |
| Acinetobacter baumanii | (SEQ ID NO.: 43)<br>TGGGGACAATGGCCAGCCCCTTATCACTTTCCTAGA |
| Neisseria meningitidis | (SEQ ID NO.: 44)<br>TGGGGACAATGGCCAGCCCCTTCGCTTTTGCTGTTG |
| Pseudomonas aeruginosa | (SEQ ID NO.: 45)<br>TGGGGACAATGGCCAGCCCTTCGGCACTTTCAGTAA |
| Rhodobacter sphaeroides | (SEQ ID NO.: 46)<br>TGGGGACAATGGCTAGCCCGATGACTTTCACGGTAC |
| Deinococcus radiourans | (SEQ ID NO.: 47)<br>TTAGGACCTGATCGGATCCTGGGACGGTACCCGGCT |

Identifying Organisms In Vitro

A sequencing run was performed as described above in vitro using target nucleic acids that included nucleotide sequences of the V3 region of the 16S rRNA gene sequence for the various organisms listed in Table 7. The obtained sequence representation from each sequencing run was used to identify particular organisms from the predicted sequences listed in Table 8. Table 9 shows sequence representation obtained from each round of six SBS cycles of the sequencing run, and organism identified from the sequence representation.

TABLE 9

| SBS cycle sequences | PF | Sequence representation (concatamerized SBS cycle sequences) | Identified organism |
|---|---|---|---|
| TAGGGA<br>CGGAAG<br>CCGAGC<br>CGGATC<br>CGAGTG<br>CACACT | 1 | TAGGGACGGAAGCCGAGCCGGATCCGAGTGCACACT<br>(SEQ ID NO: 35) | Streptococcus pneumoniae |
| TGGGGA<br>CAATGG<br>CCAGCC<br>CCTTAT | 0 | TGGGGACAATGGCCAGCCCCTTATCACTTTCCTAGA<br>(SEQ ID NO: 43) | Acinetobacter baumanii |

TABLE 9-continued

| SBS cycle sequences PF | Sequence representation (concatamerized SBS cycle sequences) | Identified organism |
|---|---|---|
| CACTTT CCTAGA | | |
| CCGCGG CACCAC CCGTTT CTCTTT CCGTTT CCTTCC | 0 CCGCGGCACCACCCGTTTCTCTTTCCGTTTCCTTCC (SEQ ID NO: 48) | Unidentified |
| TGGGGA CAATGG CCAGCC CCTTCG CTTTTG CTGTTG | 1 TGGGGACAATGGCCAGCCCCTTCGCTTTTGCTGTTG (SEQ ID NO: 44) | Neisseria meningitidis |
| TGGGGA CAATGG CAGCAA CGGTCT CTCTGT CGATAA | 1 TGGGGACAATGGCAGCAACGGTCTCTCTGTCGATAA (SEQ ID NO: 40) | Clostridium beijerincki |
| TTAGGA CCTGAT CGGATC CTGGGA CGGTAC CCGGCT | 0 TTAGGACCTGATCGGATCCTGGGACGGTACCCGGCT (SEQ ID NO: 47) | Deinococcus radiourans |
| TAGGGA CGAAAG CGGAGC CTTCGG CTCTGT CATATG | 1 TAGGGACGAAAGCGGAGCCTTCGGCTCTGTCATATG (SEQ ID NO: 32) | Staphylococcus aureus |

Figure 7:
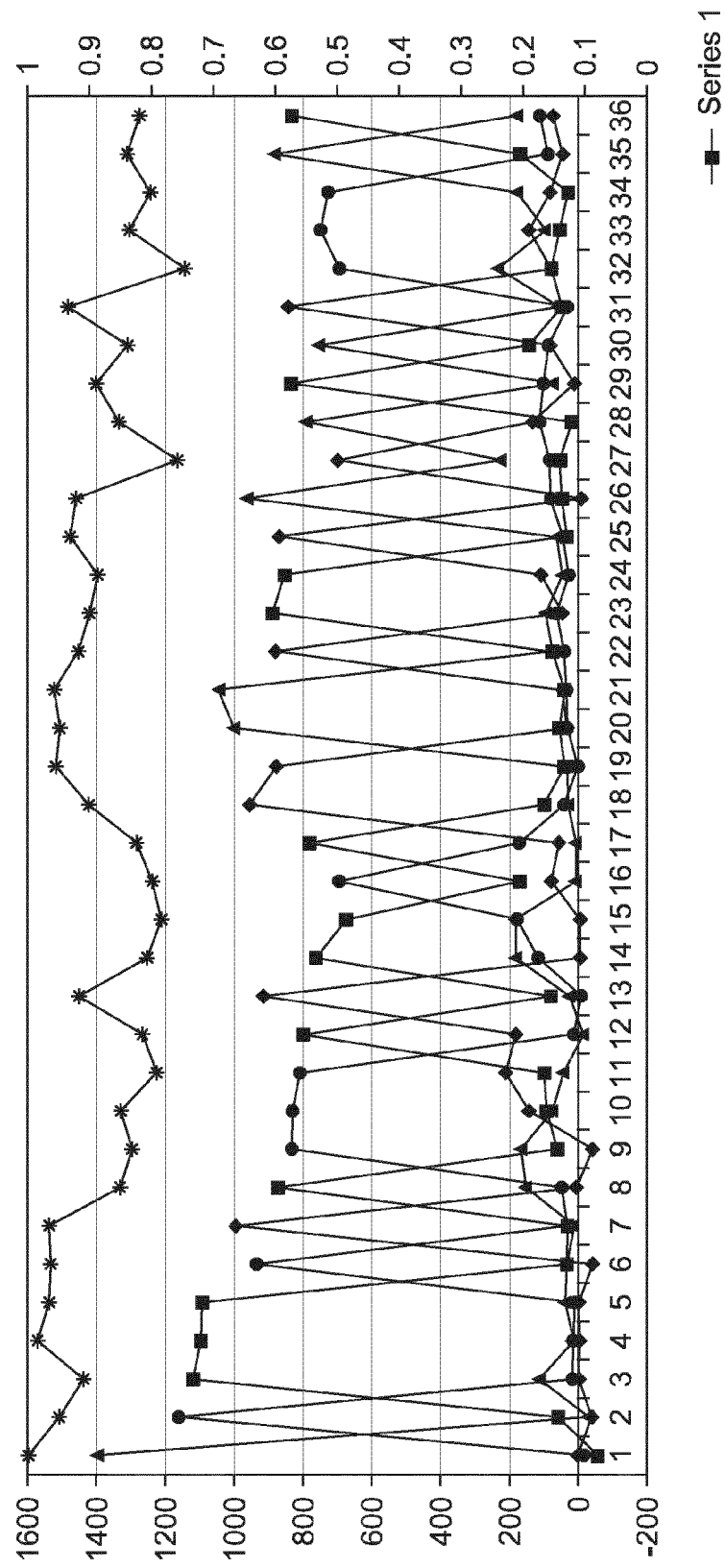
FIG. 7 shows a graph of nucleotide-calls in a sequencing run. The sequencing run included six cycles, each cycle including: six limited read steps, followed by a round of dark extension. The sequence representation identified sequences associated with *S. epidermidis*. Chastity is represented in the uppermost line (*). 'A' nucleotide-call (♦); 'C' nucleotide-call (■); 'G' nucleotide-call (•); and 'T' nucleotide-call (▲).
Figure 8:
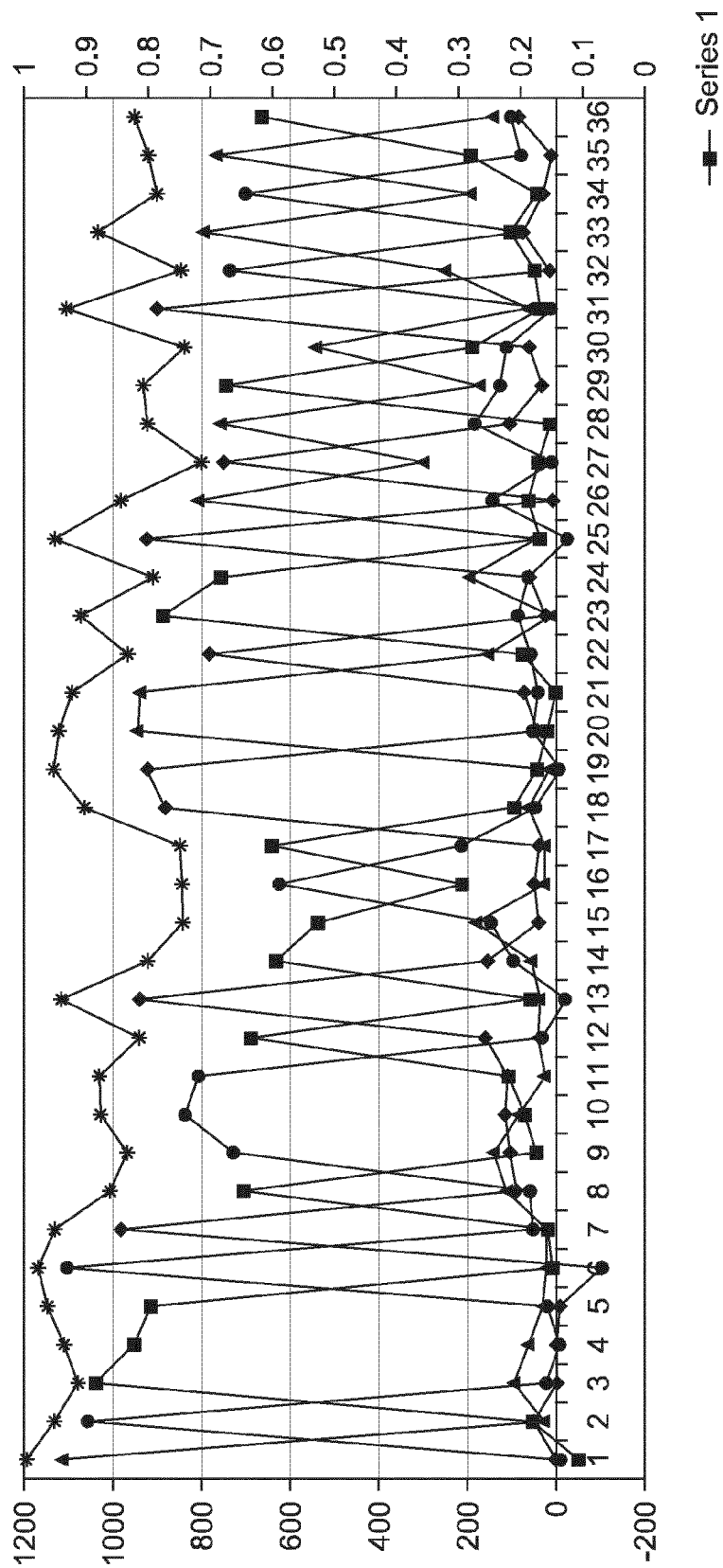
FIG. 8 shows a graph of nucleotide-calls in a sequencing run. The sequencing run included six cycles, each cycle including: six limited read steps, followed by a round of dark extension. The sequence representation identified sequences associated with *S. aureus*. Chastity is represented in the uppermost line (*). 'A' nucleotide-call (♦); 'C' nucleotide-call (■); 'G' nucleotide-call (•); and 'T' nucleotide-call (▲).
Figure 9:
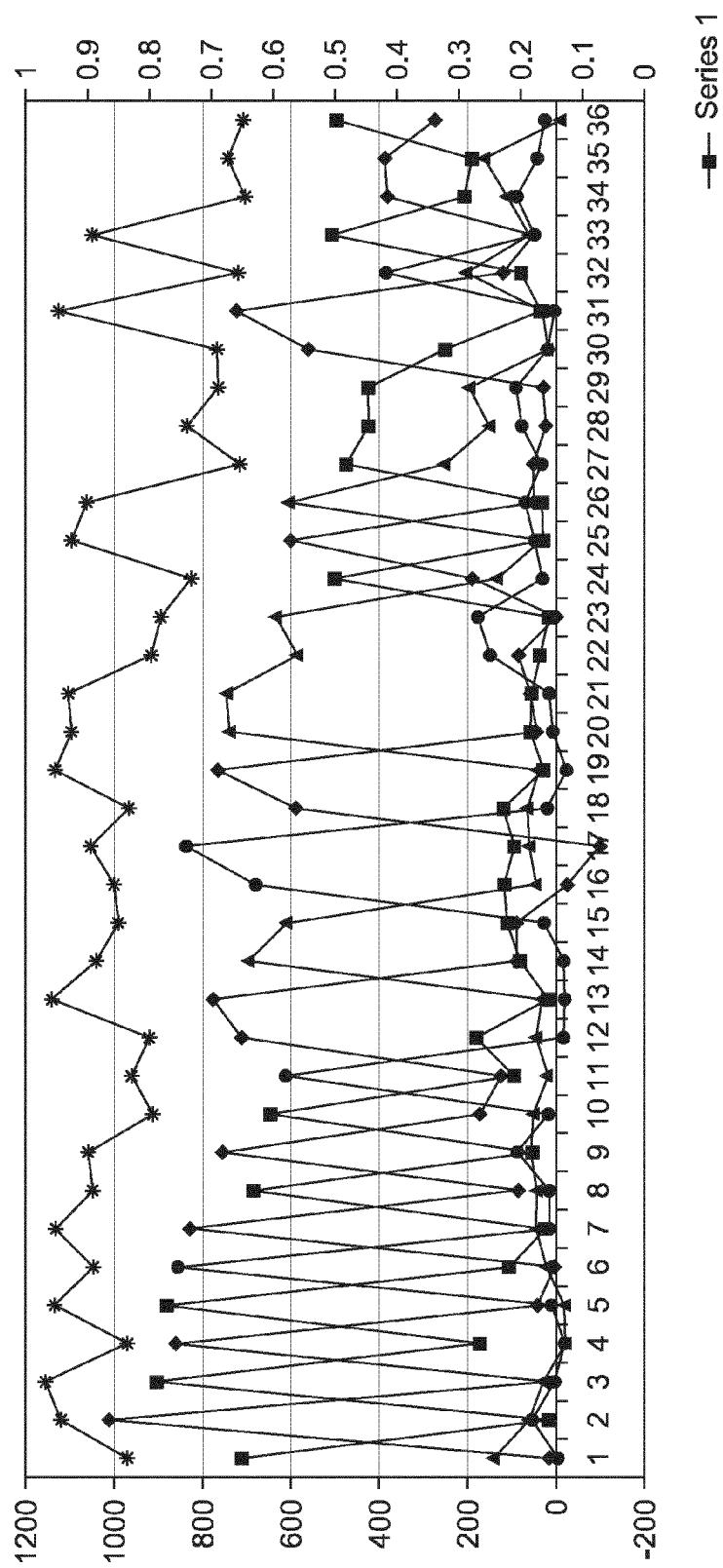
FIG. 9 shows a graph of nucleotide-calls in a sequencing run. The sequencing run included six cycles, each cycle including: six limited read steps, followed by a round of dark extension. The sequence representation identified sequences associated with *M. smithii*.

FIGS. 7, 8, and 9 show graphs of nucleotide-calls in a sequencing run that identified sequences associated with *S. epidermidis*, *S. aureus*, and *M. smithii*, respectively. In FIG. 8, at least the nucleotide-call 33 distinguished the sequence representation obtained for *S. aureus* from the sequence representations obtained from *S. epidermidis*, and *M. smithii*. In FIG. 9, at least the nucleotide-call 32 distinguished the sequence representation obtained from *M. smithii* from the sequence representation obtained from *S. epidermidis*, and *S. aureus*.

Consecutive Nucleotides Advanced in Rounds of Dark Extension

Figure 10:
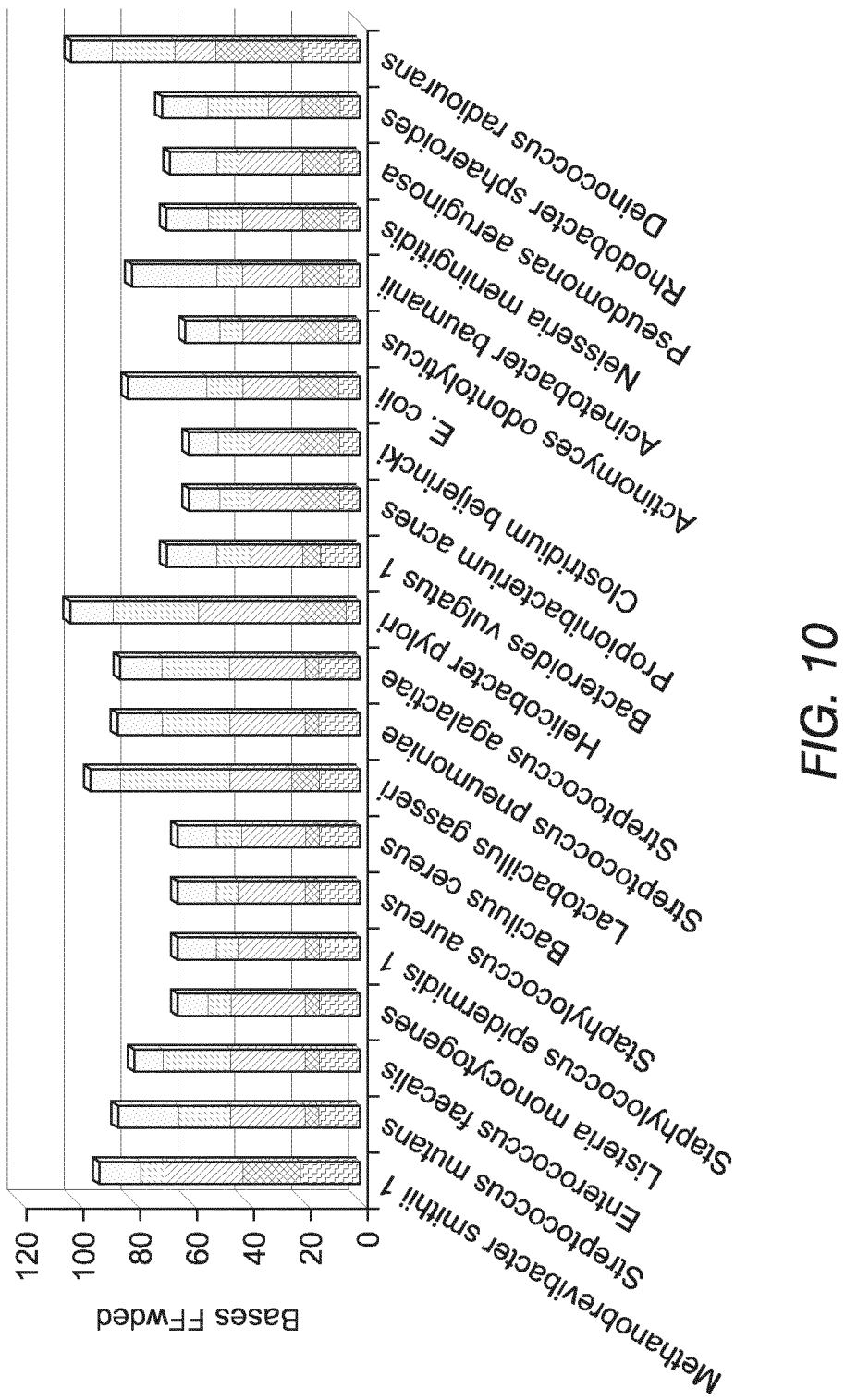
FIG. 10 shows a graph of the total number of nucleotides advanced in rounds of dark extension in a sequencing run for sequence representations identified to particular organisms.

Sequences obtained in each round of SBS cycles were mapped to the genome of each organism. The lengths of consecutive nucleotides between mapped sequences were measured to give the number of consecutive nucleotides advanced in a round of dark extension. FIG. 10 shows a graph of the number of consecutive nucleotides advanced in each round of dark extension in each sequencing run for each organism. Typically, total number of nucleotides advanced in the dark extension rounds was greater than 62 nucleotides, and less than 102 nucleotides.

Single Tile Analysis—Equal Loading

Target nucleic acids for each organism in the mock community were loaded onto a substrate in approximately equal amounts. Sequencing runs with the target nucleic acids were performed on the substrate in parallel. Sequence representations were obtained, and the sequence representation was associated with a predicted sequence representation from a particular organism. Table 10 shows the number of sequence representations obtained for various organisms in the parallel sequencing runs, and the percentage of sequence representations that identified each organism.

TABLE 10

| Organism | Actual No. of reads | Actual % | Theoretical % |
|---|---|---|---|
| Acinetobacter baumanii | 10695 | 13.69 | 4.7 |
| Bacteroides vulgatus 1 | 9962 | 12.75 | 4.7 |
| Deinococcus radiourans | 8922 | 11.42 | 4.7 |
| Staphylococcus epidermidis 1 | 6282 | 8.04 | 4.7 |
| Clostridium beijerincki | 5631 | 7.21 | 4.7 |
| Streptococcus pneumoniae | 5196 | 6.65 | 4.7 |
| Staphylococcus aureus | 4713 | 6.03 | 4.7 |
| Neisseria meningitidis | 4291 | 5.49 | 4.7 |
| Propionibacterium acnes | 4121 | 5.27 | 4.7 |
| Streptococcus mutans | 3754 | 4.80 | 4.7 |
| Listeria monocytogenes | 3677 | 4.71 | 4.7 |
| Actinomyces odontolyticus | 2873 | 3.68 | 4.7 |
| Escherichia coli | 2078 | 2.66 | 4.7 |
| Helicobacter pylori | 1976 | 2.53 | 4.7 |
| Enterococcus faecalis | 1395 | 1.79 | 4.7 |
| Baciluus cereus | 1207 | 1.54 | 4.7 |
| Rhodobacter sphaeroides | 599 | 0.77 | 4.7 |
| Pseudomonas aeruginosa | 480 | 0.61 | 4.7 |
| Streptococcus agalactiae | 218 | 0.28 | 4.7 |
| Lactobacillus gasseri | 49 | 0.06 | 4.7 |
| Methanobrevibacter smithii 1 | 28 | 0.04 | 4.7 |
| | 78147 (Total) | 100 (Total) | |

Single Tile Analysis—Staggered Loading

Figure 11:
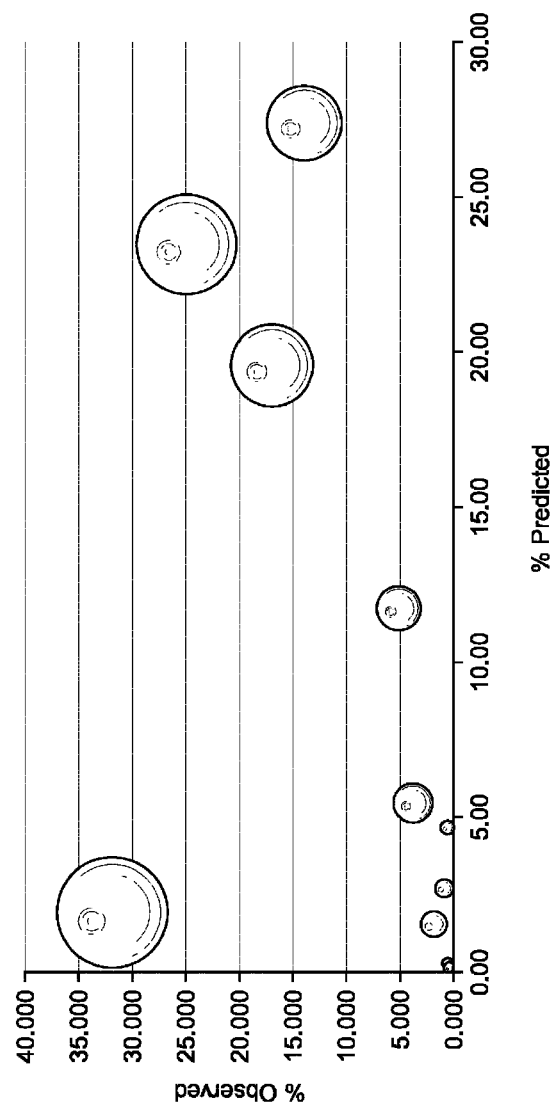
FIG. 11 shows a graph for predicted percentage of sequence representations that identify an organism vs. observed percentage of sequence representations that identify an organism.

Target sequences for each organism in the mock community were loaded on to a substrate in unequal amounts. Sequencing runs with the target nucleic acids were performed on the substrate in parallel. Sequence representations were obtained, and the sequence representation was associated with a predicted sequence representation from a particular organism. Table 11 shows the number of sequence representations obtained for various organisms in the parallel sequencing runs (No. Matches), the percentage of sequence representations that identified each organism (% of total), the relative number of cells for each organism loaded on to the substrate (Theoretical No. of cells), the number of copies of different V3 sequences present in the genome (No. copies), the theoretical number of copies. The predicted percentage of sequence representations that identify an organism (theoretical % by copies) was calculated, and compared with the observed percentage of sequence representations that identify an organism. FIG. 11 shows a graph for predicted percentage of sequence representations that identify an organism vs. observed percentage of sequence representations that identify an organism.

Example 11

Figure 12A:
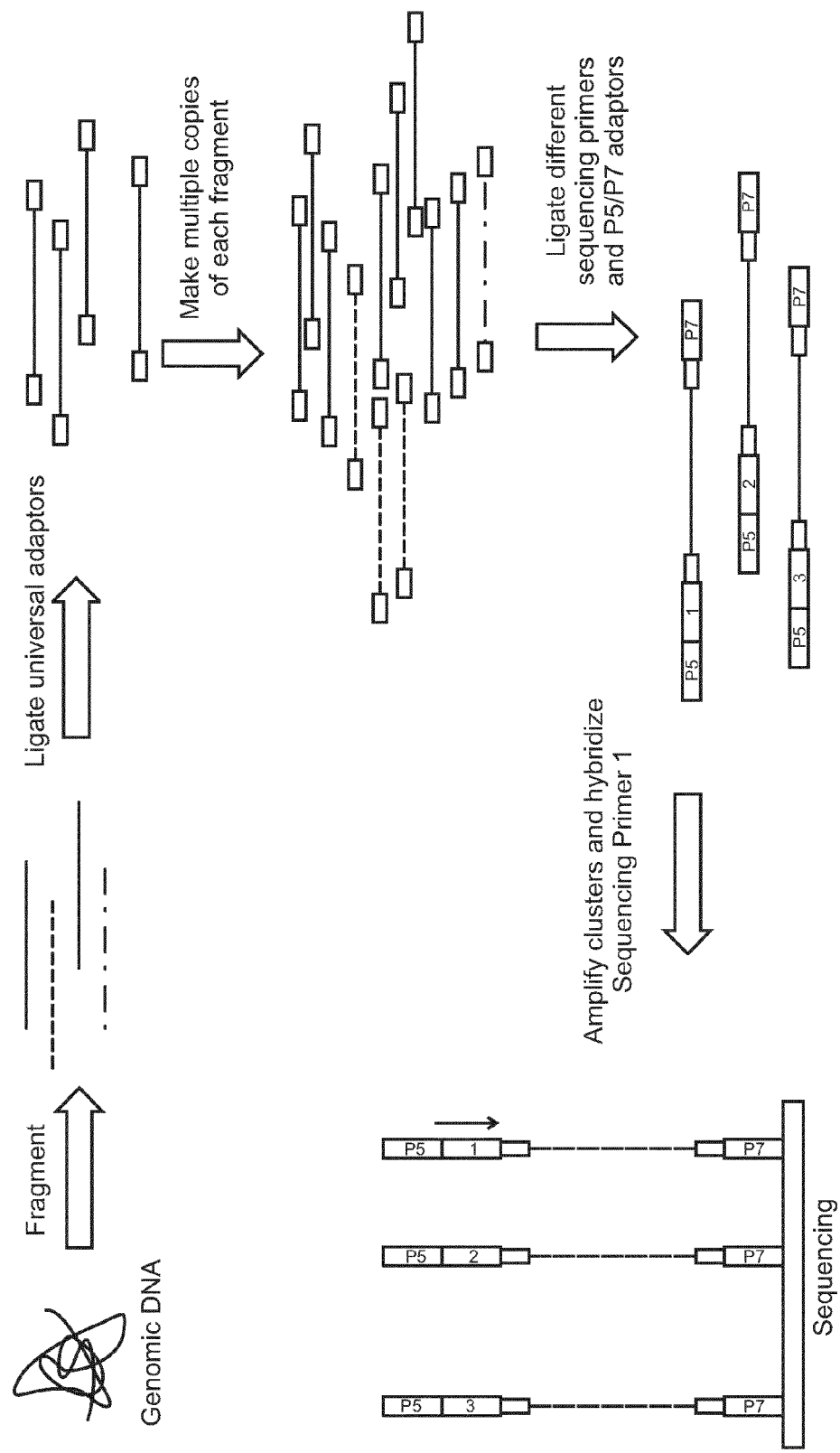
FIG. 12A is a schematic illustration showing preparation of genomic DNA for generating overlapping sequencing reads using fast forwarding.
Figure 12B:
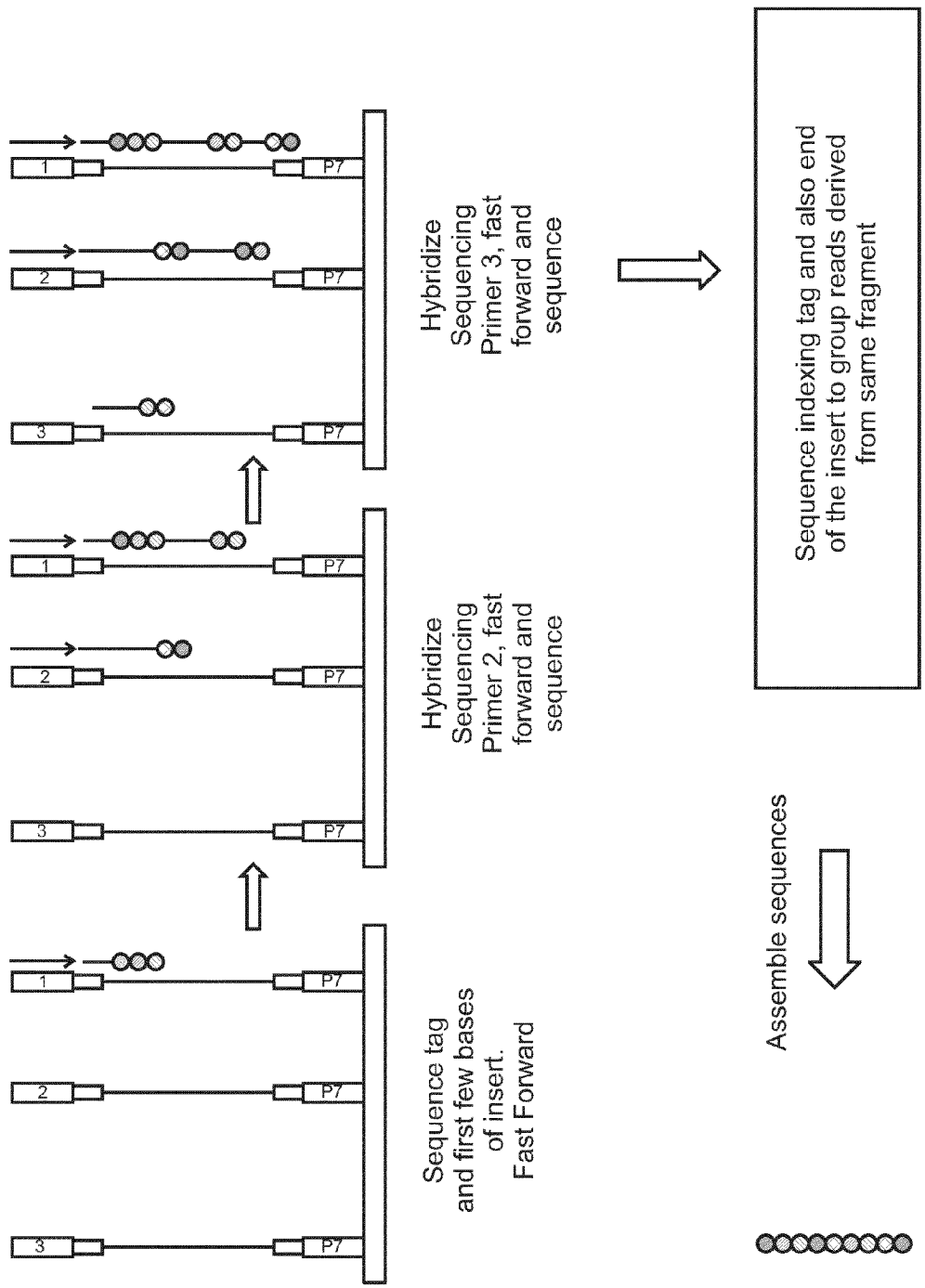
FIG. 12B is a schematic illustration of the fast forwarding sequencing method and assembly of overlapping sequence reads into a contiguous nucleotide sequence of a nucleic acid of interest.

Generating Overlapping Sequences by Fast Forwarding with Different Sequencing Primers As shown in FIG. 12A, genomic DNA is fragmented and ligated to universal adaptors. Multiple copies of each fragment are generated by amplification and ligated to different sequencing primer sites (e.g., Seq 1, Seq 2, or Seq 3), a common index tag, and common amplification primers 95 on one end and P7 on the other end. The fragments are hybridized to a site on a flow cell and bridge amplified. As shown in FIG. 12B, sequencing is commenced by adding primer Seq 1, fast forwarding and then sequencing for a desired lead time; adding primer Seq 2, fast forwarding and then sequencing while continuing the fast forwarding and sequencing initiated from primer Seq 1; and adding primer Seq 3, fast forwarding and then sequencing while continuing the fast forwarding and sequencing initiated from primers Seq 1 and Seq 2. As a result of the temporally staggered addition of Seq 1, Seq 2, and Seq 3, overlapping sequence reads of varying lengths are gener-

TABLE 11

| Organism | No. Matches | % of Total | Theoretical No. of cells | No. Copies | Theoretical No. by Copies | Theoretical % by Copies | Actual % by Seq | Actual/ Theoretical |
|---|---|---|---|---|---|---|---|---|
| *Staphylococcus aureus* | 27711 | 31.776 | 0.1 | 5 | 0.5 | 1.96 | 31.776 | 16.22 |
| *Staphylococcus epidermidis* 1 | 21652 | 24.829 | 1 | 6 | 6 | 23.51 | 24.829 | 1.06 |
| *Streptococcus mutans* | 14689 | 16.844 | 1 | 5 | 5 | 19.59 | 16.844 | 0.86 |
| *E. coli* | 12108 | 13.884 | 1 | 7 | 7 | 27.43 | 13.884 | 0.51 |
| *Rhodobacter sphaeroides* | 4361 | 5.001 | 1 | 3 | 3 | 11.76 | 5.001 | 0.43 |
| *Clostridium beijerincki* | 3223 | 3.696 | 0.1 | 14 | 1.4 | 5.49 | 3.696 | 0.67 |
| *Pseudomonas aeruginosa* | 1458 | 1.672 | 0.1 | 4 | 0.4 | 1.57 | 1.672 | 1.07 |
| *Streptococcus agalactiae* | 663 | 0.760 | 0.1 | 7 | 0.7 | 2.74 | 0.760 | 0.28 |
| *Baciluus cereus* | 370 | 0.424 | 0.1 | 12 | 1.2 | 4.70 | 0.424 | 0.09 |
| *Acinetobacter baumanii* | 304 | 0.349 | 0.01 | 7 | 0.07 | 0.27 | 0.349 | 1.27 |
| *Propionibacterium acnes* | 253 | 0.290 | 0.01 | 3 | 0.03 | 0.12 | 0.290 | 2.47 |
| *Neisseria meningitidis* | 202 | 0.232 | 0.01 | 4 | 0.04 | 0.16 | 0.232 | 1.48 |
| *Methanobrevibacter smithii* 1 | 76 | 0.087 | 0.01 | 2 | 0.02 | 0.08 | 0.087 | 1.11 |
| *Listeria monocytogenes* | 62 | 0.071 | 0.01 | 6 | 0.06 | 0.24 | 0.071 | 0.30 |
| *Bacteroides vulgatus* 1 | 26 | 0.030 | 0.001 | 7 | 0.007 | 0.03 | 0.030 | 1.09 |
| *Helicobacter pylori* | 21 | 0.024 | 0.01 | 2 | 0.02 | 0.08 | 0.024 | 0.31 |
| *Actinomyces odontolyticus* | 11 | 0.013 | 0.001 | 3 | 0.003 | 0.01 | 0.013 | 1.07 |
| *Streptococcus pneumoniae* | 9 | 0.0010 | 0.001 | 4 | 0.004 | 0.02 | 0.010 | 0.66 |
| *Enterococcus faecalis* | 4 | 0.005 | 0.001 | 4 | 0.004 | 0.02 | 0.005 | 0.29 |
| *Lactobacillus gasseri* | 2 | 0.002 | 0.01 | 6 | 0.06 | 0.24 | 0.002 | 0.01 |
| *Deinococcus radiourans* | 1 | 0.001 | 0.001 | 3 | 0.003 | 0.01 | 0.001 | 0.10 |

Example 12

Spatially Segregated Generation of Overlapping Sequences Using the Same Sequencing Primers Added at Different Times As shown in FIG. 13, different P7 and P5 adaptor-flanked amplicon inserts are ligated to the same sequencing primer sites for reading both the amplicon insert and a tag unique to each amplicon. The different amplicons are then pooled and distributed among eight spatially segregated lanes of a flow cell. Sequencing primer is sequentially added to each lane of the flow cell at different times, beginning with Lane 8 and ending with Lane 1, and all lanes are sequenced with fast forwarding during each sequential addition of the sequencing primer. As a result, an increasing number fast forward sequencing cycles will occur moving from Lane 1 to Lane 8, thereby generating overlapping sequence reads for the different amplicons. The progression of fast forwarding across the lanes provides the order of the amplicon read and the amplicon is identified by the tag read.

Example 13

Spatially Segregated Generation of Overlapping Sequences Using the Same Sequencing Primers Added at the Same Time As shown in FIG. 13, different P7 and P5 adaptor-flanked amplicon inserts are ligated to the same sequencing primer sites for reading both the amplicon insert and a tag unique to each amplicon. The different amplicons are then pooled and distributed among eight spatially segregated lanes of a flow cell. Sequencing primer is added to each lane of the flow cell at the same time and the lanes are subjected to an increasing number of fast forward sequencing cycles across the lanes moving from Lane 1 to Lane 8, thereby generating overlapping sequence reads for the different amplicons. The progression of fast forwarding across the lanes provides the order of the amplicon read and the amplicon is identified by the tag read.

The above description discloses several methods and systems of the present invention. This invention is susceptible to modifications in the methods and materials, as well as alterations in the fabrication methods and equipment. Such modifications will become apparent to those skilled in the art from a consideration of this disclosure or practice of the invention disclosed herein. For example, the invention has been exemplified using nucleic acids but can be applied to other polymers as well. Consequently, it is not intended that this invention be limited to the specific embodiments disclosed herein, but that it cover all modifications and alternatives coming within the true scope and spirit of the invention.

All references cited herein including, but not limited to, published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

What is claimed is:

1. A method of generating overlapping sequencing reads, said method comprising:
   providing a substrate having a surface, said surface comprising a site having a plurality of polynucleotides attached thereto; and
   performing sequencing runs on said plurality of polynucleotides, said sequencing runs being initiated at different times such that said sequencing runs proceed for different durations, thereby generating a set of overlapping sequencing reads, wherein performing a sequencing run comprises:
   (a) providing a first sequencing reagent to a target nucleic acid in the presence of a polymerase, said first sequencing reagent comprising one or more nucleotide monomers, wherein said one or more nucleotide monomers pair with no more than three nucleotide types in said target, thereby forming a polynucleotide complementary to at least a portion of said target; and
   (b1) providing a second sequencing reagent to said target nucleic acid, said second sequencing reagent comprising at least one nucleotide monomer, said at least one nucleotide monomer of said second sequencing reagent comprising a reversibly terminating moiety, wherein said second sequencing reagent is provided subsequent to providing said first sequencing reagent, whereby sequence information for at least a portion of said target nucleic acid is obtained; or
   (b2) providing a second sequencing reagent to said target nucleic acid, said second sequencing reagent comprising at least one nucleotide monomer, wherein said at least one nucleotide monomer pairs with no more than three nucleotide types in said target, wherein said second sequencing reagent is provided subsequent to providing said first sequencing reagent, and wherein a signal that indicates the incorporation of said at least one nucleotide monomer into the polynucleotide is generated, whereby sequence information for at least a portion of said target nucleic acid is obtained.

2. The method of claim 1, further comprising the step of assembling sequencing reads from said set of overlapping sequencing reads so as to obtain a contiguous nucleotide sequence of a nucleic acid of interest.

3. The method of claim 1, wherein providing said substrate comprises hybridizing a plurality of template nucleic acids to a plurality of capture probes attached to said site and extending said capture probes, thereby producing a plurality of polynucleotides at said site.

4. The method of claim 3, wherein each template nucleic acid comprises an adaptor that is complementary to a capture probe attached to said site.

5. The method of claim 4, wherein performing a sequencing run comprises extending a sequencing primer, thereby producing extended strands.

6. The method of claim 1, wherein said plurality of polynucleotides comprises copies of the same fragment of a nucleic acid of interest.

7. The method of claim 6, wherein said copies comprise oligonucleotide adaptors at each end.

8. The method of claim 6, wherein each copy comprises a different sequencing primer site.

9. The method of claim 8, wherein performing a sequencing run comprises providing sequencing primers that are complementary to said different sequencing primer sites.

10. The method of claim 6, wherein said copies further comprise an index tag, wherein copies having the same index tag are copies of the same fragment of the nucleic acid of interest.

11. The method of claim 10, wherein said index tag identifies sequencing reads derived from the same fragment of the nucleic acid of interest.

12. The method of claim 6, wherein said plurality of polynucleotides further comprises copies of different fragments of the nucleic acid of interest.

13. The method of claim 12, wherein said copies of different fragments comprise different index tags.

14. The method of claim 13, wherein said copies of different fragments are identified by the sequence of said different index tags.

15. A method of generating overlapping sequencing reads, said method comprising:
providing a substrate having a surface, said surface comprising a first site and a second site, said first and second sites having a plurality of polynucleotides attached thereto and said first and second sites being spatially segregated from each other; and
performing a sequencing run on said plurality of polynucleotides so as to produce an extended strand at said first and second spatially segregated sites, wherein the length of said extended strand produced at said first site is different from the length of said extended strand produced at said second site, thereby generating a set of overlapping sequencing reads, wherein performing a sequencing run comprises:
(a) providing a first sequencing reagent to a target nucleic acid in the presence of a polymerase, said first sequencing reagent comprising one or more nucleotide monomers, wherein said one or more nucleotide monomers pair with no more than three nucleotide types in said target, thereby forming a polynucleotide complementary to at least a portion of said target; and
(b1) providing a second sequencing reagent to said target nucleic acid, said second sequencing reagent comprising at least one nucleotide monomer, said at least one nucleotide monomer of said second sequencing reagent comprising a reversibly terminating moiety, wherein said second sequencing reagent is provided subsequent to providing said first sequencing reagent, whereby sequence information for at least a portion of said target nucleic acid is obtained; or
(b2) providing a second sequencing reagent to said target nucleic acid, said second sequencing reagent comprising at least one nucleotide monomer, wherein said at least one nucleotide monomer pairs with no more than three nucleotide types in said target, wherein said second sequencing reagent is provided subsequent to providing said first sequencing reagent, and wherein a signal that indicates the incorporation of said at least one nucleotide monomer into the polynucleotide is generated, whereby sequence information for at least a portion of said target nucleic acid is obtained.

16. The method of claim 1, wherein the substrate comprises a flow chamber.

17. The method of claim 1, wherein the surface is planar.

18. The method of claim 1, wherein the surface is patterned.

19. The method of claim 1, wherein the surface comprises a channel in a flow chamber.

20. The method of claim 1, wherein said site comprises a well.

21. The method of claim 1, wherein said site comprises a bead in a well.

22. The method of claim 1, wherein the one or more nucleotide monomers of the first sequencing reagent pair with at least two different nucleotide types in said target.

23. The method of claim 1, wherein the one or more nucleotide monomers of the second sequencing reagent pair with at least two different nucleotide types in said target.

24. The method of claim 1, wherein the first sequencing regent includes at least two different nucleotide monomers.

25. The method of claim 1, wherein the one or more nucleotide monomers of the first sequencing reagent lack a reversibly terminating moiety.

26. The method of claim 1, further comprising the step of removing the unincorporated second sequencing reagent from the substrate.

27. The method of claim 1, further comprising the step of removing the reversibly terminating moiety from the second sequencing reagent.

28. The method of claim 27, wherein the unincorporated first sequencing reagent is removed prior to removing the reversibly terminating moiety from the second sequencing reagent.

29. The method of claim 1, further comprising repeating step (a) at least once prior to repeating step (b).

30. The method of claim 1, further comprising detecting incorporation of the at least one nucleotide monomer of the second sequencing reagent into said polynucleotide.

* * * * *

SEQUENCE LISTING

```
<160> NUMBER OF SEQ ID NOS: 48

<210> SEQ ID NO 1
<211> LENGTH: 17
<212> TYPE: DNA
<213> ORGANISM: Artificial Sequence
<220> FEATURE:
<223> OTHER INFORMATION: random example sequence

<400> SEQUENCE: 1
ggatcacagg cggaaac                                              17

<210> SEQ ID NO 2
<211> LENGTH: 158
<212> TYPE: DNA
<213> ORGANISM: Acinetobacter baumanii

<400> SEQUENCE: 2
tggggaatat tggacaatgg ggggaaccct gatccagcca tgccgcgtgt gtgaagaagg    60
ccttatggtt gtaaagcact ttaagcgagg aggaggctta cctggttaat acccaggata   120
agtggacgtt actcgcagaa taagcaccgg ctaactct                           158

<210> SEQ ID NO 3
<211> LENGTH: 173
<212> TYPE: DNA
<213> ORGANISM: Actinomyces odontolyticus
```

```
<400> SEQUENCE: 3
tggggaatat tgcacaatgg gcgcaagcct gatgcagcga cgccgcgtga gggatggagg      60
ccttcgggtt gtgaacctct ttcgccagtg aagcaggccc gcctcttttg tgggtgggtt     120
gacggtagct ggataagaag cgccggctaa ctacgtgcca gcagccgcgg taa            173

<210> SEQ ID NO 4
<211> LENGTH: 158
<212> TYPE: DNA
<213> ORGANISM: Baciluus cereus

<400> SEQUENCE: 4
tagggaatct tccgcaatgg acgaaagtct gacggagcaa cgccgcgtga gtgatgaagg      60
ctttcgggtc gtaaaactct gttgttaggg aagaacaagt gctagttgaa taagctggca    120
ccttgacggt acctaaccag aaagccacgg ctaactac                             158

<210> SEQ ID NO 5
<211> LENGTH: 152
<212> TYPE: DNA
<213> ORGANISM: Bacteroides vulgatus

<400> SEQUENCE: 5
tgaggaatat tggtcaatgg gcgagagcct gaaccagcca agtagcgtga aggatgactg      60
ccctatgggt tgtaaacttc ttttataaag gaataaagtc gggtatgcat accgtttgc     120 atgtacttta tgaataagga tcggctaact cc                                   152

<210> SEQ ID NO 6
<211> LENGTH: 152
<212> TYPE: DNA
<213> ORGANISM: Bacteroides vulgatus

<400> SEQUENCE: 6
tgaggaatat tggtcaatgg gcgcaggcct gaaccagcca agtagcgtga aggatgactg      60
ccctatgggt tgtaaacttc ttttataaag gaataaagtc gggtatggat accgtttgc     120 atgtacttta tgaataagga tcggctaact cc                                   152

<210> SEQ ID NO 7
<211> LENGTH: 152
<212> TYPE: DNA
<213> ORGANISM: Bacteroides vulgatus

<400> SEQUENCE: 7
tgaggaatat tggtcaatgg gcgagagcct gaaccagcca agtagcgtga aggatgactg      60
ccctatgggt tgtaaacttc ttttataaag gaataaagtc gggtatggat accgtttgc     120 atgtacttta tgaataagga tcggctaact cc                                   152

<210> SEQ ID NO 8
<211> LENGTH: 132
<212> TYPE: DNA
<213> ORGANISM: Clostridium biijerincki

<400> SEQUENCE: 8
tggggaatat tgcacaatgg gggaaaccct gatgcagcaa cgccgcgtga gtgatgacgg      60
tcttcggatt gtaaagctct gtcttcaggg acgataatga cggtacctga ggaggaagcc    120
acggctaact ac                                                         132

<210> SEQ ID NO 9
```

```
<211> LENGTH: 144
<212> TYPE: DNA
<213> ORGANISM: Deinococcus radiourans

<400> SEQUENCE: 9
ttaggaatct tccacaatgg gcgcaagcct gatggagcga cgccgcgtga gggatgaagg      60
ttttcggatc gtaaacctct gaatctggga cgaaagagcc ttagggcaga tgacggtacc    120
agagtaatag caccggctaa ctcc                                            144

<210> SEQ ID NO 10
<211> LENGTH: 157
<212> TYPE: DNA
<213> ORGANISM: Escherichia coli

<400> SEQUENCE: 10
tggggaatat tgcacaatgg gcgcaagcct gatgcagcca tgccgcgtgt atgaagaagg     60
ccttcgggtt gtaaagtact ttcagcgggg aggaagggag taaagttaat acctttgctc   120
attgacgtta cccgcagaag aagcaccggc taactcc                             157

<210> SEQ ID NO 11
<211> LENGTH: 157
<212> TYPE: DNA
<213> ORGANISM: Enterococcus faecalis

<400> SEQUENCE: 11
tagggaatct tcggcaatgg acgaaagtct gaccgagcaa cgccgcgtga gtgaagaagg     60
ttttcggatc gtaaaactct gttgttagag aagaacaagg acgttagtaa ctgaacgtcc   120
cctgacggta tctaaccaga aagccacggc taactac                             157

<210> SEQ ID NO 12
<211> LENGTH: 145
<212> TYPE: DNA
<213> ORGANISM: Helicobacter pylori

<400> SEQUENCE: 12
tagggaatat tgctcaatgg gggaaaccct gaagcagcaa cgccgcgtgg aggatgaagg     60
ttttaggatt gtaaactcct tttgttagag aagataatga ctaacgaata agcaccggct   120
aactccgtgc cagcagccgc ggtaa                                          145

<210> SEQ ID NO 13
<211> LENGTH: 157
<212> TYPE: DNA
<213> ORGANISM: Lactobacillus gasseri

<400> SEQUENCE: 13
tagggaatct tccacaatgg acgcaagtct gatggagcaa cgccgcgtga gtgaagaagg     60
gtttcggctc gtaaagctct gttggtagtg aagaaagata gaggtagtaa ctggccttta   120
tttgacggta attacttaga aagtcacggc taactac                             157

<210> SEQ ID NO 14
<211> LENGTH: 157
<212> TYPE: DNA
<213> ORGANISM: Listeria monocytogenes

<400> SEQUENCE: 14
tagggaatct tccgcaatgg acgaaagtct gacggagcaa cgccgcgtgt atgaagaagg     60
ttttcggatc gtaaagtact gttgttagag aagaacaagg ataagagtaa ctgcttgtcc   120
```

```
cttgacggta tctaaccaga aagccacggc taactac                              157
```

<210> SEQ ID NO 15
<211> LENGTH: 154
<212> TYPE: DNA
<213> ORGANISM: Methanobrevibacter smithii

<400> SEQUENCE: 15

```
gcgcgaaacc tccgcaatgt gagaaatcgc gacgggggg atcccaagtg ccattcttaa     60
cgggatggct tttcattagt gtaaagagct tttggaataa gagctgggca agaccggtgc   120
cagccgccgc ggtaagtgcc agccgccgcg gtaa                               154
```

<210> SEQ ID NO 16
<211> LENGTH: 153
<212> TYPE: DNA
<213> ORGANISM: Methanobrevibacter smithii

<400> SEQUENCE: 16

```
gcgcgaaacc tccgcaatgt gagaaatcgc gacgggggga tcccaagtgc cattcttaac     60
gggatggctt tcattagtg taaagagctt ttggaataag agctgggcaa gaccggtgcc   120
agccggccgc ggtaagtgcc agccgccgcg gta                                153
```

<210> SEQ ID NO 17
<211> LENGTH: 157
<212> TYPE: DNA
<213> ORGANISM: Neisseria meningitidis

<400> SEQUENCE: 17

```
tggggaattt tggacaatgg gcgcaagcct gatccagcca tgccgcgtgt ctgaagaagg     60
ccttcgggtt gtaaaggact tttgtcaggg aagaaaaggc tgttgctaat atcagcggct   120
gatgacggta cctgaagaat aagcaccggc taactac                             157
```

<210> SEQ ID NO 18
<211> LENGTH: 137
<212> TYPE: DNA
<213> ORGANISM: Propionibacterium acnes

<400> SEQUENCE: 18

```
tggggaatat tgcacaatgg gcggaagcct gatgcagcaa cgccgcgtgc gggatgacgg     60
ccttcgggtt gtaaaccgct ttcgcctgtg acgaagcgtg agtgacggta atgggtaaag   120
aagcaccggc taactac                                                   137
```

<210> SEQ ID NO 19
<211> LENGTH: 157
<212> TYPE: DNA
<213> ORGANISM: Pseudomonas aeruginosa

<400> SEQUENCE: 19

```
tggggaatat tggacaatgg gcgaaagcct gatccagcca tgccgcgtgt gtgaagaagg     60
tcttcggatt gtaaagcact ttaagttggg aggaagggca gtaagttaat accttgctgt   120
tttgacgtta ccaacagaat aagcaccggc taacttc                             157
```

<210> SEQ ID NO 20
<211> LENGTH: 132
<212> TYPE: DNA
<213> ORGANISM: Rhodobacter sphaeroides

<400> SEQUENCE: 20

```
tggggaatct tagacaatgg gcgcaagcct gatctagcca tgccgcgtga tcgatgaagg        60
ccttagggtt gtaaagatct ttcaggtggg aagataatga cggtaccacc agaagaagcc       120
ccggctaact cc                                                           132

<210> SEQ ID NO 21
<211> LENGTH: 157
<212> TYPE: DNA
<213> ORGANISM: Staphylococcus aureus

<400> SEQUENCE: 21
tagggaatct tccgcaatgg gcgaaagcct gacggagcaa cgccgcgtga gtgatgaagg        60
tcttcggatc gtaaaactct gttattaggg aagaacatat gtgtaagtaa ctgtgcacat      120
cttgacggta cctaatcaga aagccacggc taactac                                157

<210> SEQ ID NO 22
<211> LENGTH: 157
<212> TYPE: DNA
<213> ORGANISM: Staphylococcus epidermidis

<400> SEQUENCE: 22
tagggaatct tccgcaatgg gcgaaagctt gacggagcaa cgccgcgtga gtgatgaagg        60
tcttcggatc gtaaaactct gttattaggg aagaacaaat gtgtaagtaa ctatgcacgt      120
cttgacggta cctaatcaga aagccacggc taactac                                157

<210> SEQ ID NO 23
<211> LENGTH: 157
<212> TYPE: DNA
<213> ORGANISM: Staphylococcus epidermidis

<400> SEQUENCE: 23
tagggaatct tccgcaatgg gcgaaagcct gacggagcaa cgccgcgtga gtgatgaagg        60
tcttcggatc gtaaaactct gttattaggg aagaacaaat gtgtaagtaa ctatgcacgt      120
cttgacggta cctaatcaga aagccacggc taactac                                157

<210> SEQ ID NO 24
<211> LENGTH: 158
<212> TYPE: DNA
<213> ORGANISM: Streptococcus agalactiae

<400> SEQUENCE: 24
tagggaatct tcggcaatgg acggaagtct gaccgagcaa cgccgcgtga gtgaagaagg        60
ttttcggatc gtaaagctct gttgttagag aagaacgttg gtaggagtgg aaaatctacc      120
aagtgacggt aactaaccag aaagggacgg ctaactac                               158

<210> SEQ ID NO 25
<211> LENGTH: 158
<212> TYPE: DNA
<213> ORGANISM: Streptococcus mutans

<400> SEQUENCE: 25
tagggaatct tcggcaatgg acgaaagtct gaccgagcaa cgccgcgtga gtgaagaagg        60
ttttcggatc gtaaagctct gttgtaagtc aagaacgtgt gtgagagtgg aaagttcaca      120
cagtgacggt agcttaccag aaagggacgg ctaactac                               158

<210> SEQ ID NO 26
<211> LENGTH: 158
<212> TYPE: DNA
```

-continued

<213> ORGANISM: Streptococcus pneumoniae

<400> SEQUENCE: 26
tagggaatct tcggcaatgg acggaagtct gaccgagcaa cgccgcgtga gtgaagaagg    60
ttttcggatc gtaaagctct gttgtaagag aagaacgagt gtgagagtgg aaagttcaca   120
ctgtgacggt atcttaccag aaagggacgg ctaactac                           158

<210> SEQ ID NO 27
<211> LENGTH: 36
<212> TYPE: DNA
<213> ORGANISM: Artificial Sequence
<220> FEATURE:
<223> OTHER INFORMATION: Predicted Concatamerized Sequences

<400> SEQUENCE: 27
gcgcgacgcg accttaacct tttgctgggc cagccg                              36

<210> SEQ ID NO 28
<211> LENGTH: 36
<212> TYPE: DNA
<213> ORGANISM: Artificial Sequence
<220> FEATURE:
<223> OTHER INFORMATION: Predicted Concatamerized Sequences

<400> SEQUENCE: 28
tagggacgaa agccgagccg gatccaagaa cacaca                              36

<210> SEQ ID NO 29
<211> LENGTH: 36
<212> TYPE: DNA
<213> ORGANISM: Artificial Sequence
<220> FEATURE:
<223> OTHER INFORMATION: Predicted Concatamerized Sequences

<400> SEQUENCE: 29
tagggacgaa agccgagccg gatccaagga ctgaac                              36

<210> SEQ ID NO 30
<211> LENGTH: 36
<212> TYPE: DNA
<213> ORGANISM: Artificial Sequence
<220> FEATURE:
<223> OTHER INFORMATION: Predicted Concatamerized Sequences

<400> SEQUENCE: 30
tagggacgaa agcggagccg gatcctgttg caagga                              36

<210> SEQ ID NO 31
<211> LENGTH: 36
<212> TYPE: DNA
<213> ORGANISM: Artificial Sequence
<220> FEATURE:
<223> OTHER INFORMATION: Predicted Concatamerized Sequences

<400> SEQUENCE: 31
tagggacgaa agcggagcct tcggctctgt caaatg                              36

<210> SEQ ID NO 32
<211> LENGTH: 36
<212> TYPE: DNA
<213> ORGANISM: Artificial Sequence
<220> FEATURE:
<223> OTHER INFORMATION: Predicted Concatamerized Sequences

<400> SEQUENCE: 32

-continued

```
tagggacgaa agcggagcct tcggctctgt catatg                              36

<210> SEQ ID NO 33
<211> LENGTH: 36
<212> TYPE: DNA
<213> ORGANISM: Artificial Sequence
<220> FEATURE:
<223> OTHER INFORMATION: Predicted Concatamerized Sequences

<400> SEQUENCE: 33
tagggacgaa agcggagcct ttcgctctgt caagtg                              36

<210> SEQ ID NO 34
<211> LENGTH: 36
<212> TYPE: DNA
<213> ORGANISM: Artificial Sequence
<220> FEATURE:
<223> OTHER INFORMATION: Predicted Concatamerized Sequences

<400> SEQUENCE: 34
tagggacgca agcaacgccg gctcctggcc cggtaa                              36

<210> SEQ ID NO 35
<211> LENGTH: 36
<212> TYPE: DNA
<213> ORGANISM: Artificial Sequence
<220> FEATURE:
<223> OTHER INFORMATION: Predicted Concatamerized Sequences

<400> SEQUENCE: 35
tagggacgga agccgagccg gatccgagtg cacact                              36

<210> SEQ ID NO 36
<211> LENGTH: 36
<212> TYPE: DNA
<213> ORGANISM: Artificial Sequence
<220> FEATURE:
<223> OTHER INFORMATION: Predicted Concatamerized Sequences

<400> SEQUENCE: 36
tagggacgga agccgagccg gatccgttgg ctacca                              36

<210> SEQ ID NO 37
<211> LENGTH: 36
<212> TYPE: DNA
<213> ORGANISM: Artificial Sequence
<220> FEATURE:
<223> OTHER INFORMATION: Predicted Concatamerized Sequences

<400> SEQUENCE: 37
tagggaccct gactccttcg gtatcaccgg cagccg                              36

<210> SEQ ID NO 38
<211> LENGTH: 36
<212> TYPE: DNA
<213> ORGANISM: Artificial Sequence
<220> FEATURE:
<223> OTHER INFORMATION: Predicted Concatamerized Sequences

<400> SEQUENCE: 38
tgaggacgag agccagccct gccccttctt cgggta                              36

<210> SEQ ID NO 39
<211> LENGTH: 36
<212> TYPE: DNA
<213> ORGANISM: Artificial Sequence
<220> FEATURE:
```

<223> OTHER INFORMATION: Predicted Concatamerized Sequences

<400> SEQUENCE: 39
tggggacaat ggcagcaacg gcctccgctt cgaagc    36

<210> SEQ ID NO 40
<211> LENGTH: 36
<212> TYPE: DNA
<213> ORGANISM: Artificial Sequence
<220> FEATURE:
<223> OTHER INFORMATION: Predicted Concatamerized Sequences

<400> SEQUENCE: 40
tggggacaat ggcagcaacg gtctctctgt cgataa    36

<210> SEQ ID NO 41
<211> LENGTH: 36
<212> TYPE: DNA
<213> ORGANISM: Artificial Sequence
<220> FEATURE:
<223> OTHER INFORMATION: Predicted Concatamerized Sequences

<400> SEQUENCE: 41
tggggacaat ggcagccacc ttcgctttca cctttg    36

<210> SEQ ID NO 42
<211> LENGTH: 36
<212> TYPE: DNA
<213> ORGANISM: Artificial Sequence
<220> FEATURE:
<223> OTHER INFORMATION: Predicted Concatamerized Sequences

<400> SEQUENCE: 42
tggggacaat ggcagcgacc ttcgcctctt caagcc    36

<210> SEQ ID NO 43
<211> LENGTH: 36
<212> TYPE: DNA
<213> ORGANISM: Artificial Sequence
<220> FEATURE:
<223> OTHER INFORMATION: Predicted Concatamerized Sequences

<400> SEQUENCE: 43
tggggacaat ggccagcccc ttatcactttt cctaga    36

<210> SEQ ID NO 44
<211> LENGTH: 36
<212> TYPE: DNA
<213> ORGANISM: Artificial Sequence
<220> FEATURE:
<223> OTHER INFORMATION: Predicted Concatamerized Sequences

<400> SEQUENCE: 44
tggggacaat ggccagcccc ttcgcttttg ctgttg    36

<210> SEQ ID NO 45
<211> LENGTH: 36
<212> TYPE: DNA
<213> ORGANISM: Artificial Sequence
<220> FEATURE:
<223> OTHER INFORMATION: Predicted Concatamerized Sequences

<400> SEQUENCE: 45
tggggacaat ggccagccct tcggcactttt cagtaa    36

<210> SEQ ID NO 46

-continued

```
<211> LENGTH: 36
<212> TYPE: DNA
<213> ORGANISM: Artificial Sequence
<220> FEATURE:
<223> OTHER INFORMATION: Predicted Concatamerized Sequences

<400> SEQUENCE: 46
tggggacaat ggctagcccg atgactttca cggtac                                 36

<210> SEQ ID NO 47
<211> LENGTH: 36
<212> TYPE: DNA
<213> ORGANISM: Artificial Sequence
<220> FEATURE:
<223> OTHER INFORMATION: Predicted Concatamerized Sequences

<400> SEQUENCE: 47
ttaggacctg atcggatcct gggacggtac ccggct                                 36

<210> SEQ ID NO 48
<211> LENGTH: 36
<212> TYPE: DNA
<213> ORGANISM: Artificial Sequence
<220> FEATURE:
<223> OTHER INFORMATION: Predicted Concatamerized Sequences

<400> SEQUENCE: 48
ccgcggcacc acccgtttct ctttccgttt ccttcc                                 36
```